US012778795B1

(12) United States Patent
Guyer et al.

(10) Patent No.: US 12,778,795 B1
(45) Date of Patent: Nov. 3, 2026

(54) ICE CONTAINER ASSEMBLY WITH IMPINGEMENT-DRIVEN CIRCULATION FOR COLD WATER IMMERSION THERAPY

(71) Applicant: Brrr Tech, LLC, Johns Creek, GA (US)

(72) Inventors: Eric Paul Guyer, Johns Creek, GA (US); Stephen Guyer, Hancock, IA (US); Neil Ferrier, Greenville, SC (US)

(73) Assignee: Brrr Tech, LLC, Johns Creek, GA (US)

( * ) Notice: Subject to any disclaimer, the term of this patent is extended or adjusted under 35 U.S.C. 154(b) by 0 days.

(21) Appl. No.: 19/572,951

(22) Filed: Mar. 20, 2026

Related U.S. Application Data

(63) Continuation-in-part of application No. 19/317,563, filed on Sep. 3, 2025, now Pat. No. 12,605,274.

(51) Int. Cl.

| | |
|---|---|
| ***F25D 3/08*** | (2006.01) |
| ***A61F 7/00*** | (2006.01) |
| ***F25D 17/02*** | (2006.01) |

(52) U.S. Cl.
CPC .............. *A61F 7/0053* (2013.01); *F25D 3/08* (2013.01); *F25D 17/02* (2013.01)

(58) Field of Classification Search
CPC .................. A61F 7/0053; A61F 7/0085; A61F 2007/0063; A61F 2007/0086; A61F 2007/0095
See application file for complete search history.

(56) References Cited

U.S. PATENT DOCUMENTS

| | | | | |
|---|---|---|---|---|
| 2023/0165708 A1* | 6/2023 | Laycox | A61F 7/0053 | 607/104 |
| 2023/0320930 A1* | 10/2023 | Hearn | A61H 33/6005 | 607/85 |
| 2024/0374473 A1* | 11/2024 | Rostoker | A61H 33/0087 | |
| 2024/0382377 A1* | 11/2024 | Ponton | A61H 33/0095 | |
| 2024/0393038 A1* | 11/2024 | Mudd | E03C 1/0408 | |

* cited by examiner

*Primary Examiner* — Tigist S Demie
(74) *Attorney, Agent, or Firm* — H. Brock Kolls

(57) ABSTRACT

The present invention relates to cold water immersion therapy systems and, more particularly, to an ice container assembly configured to rapidly chill treatment water within a tub. The ice container assembly includes an ice container configured to hold treatment ice and a lid defining internal fluid channels and impingement ports. An agitator module including a pump draws treatment water from the tub and delivers the treatment water toward the treatment ice to chill the treatment water before returning it to the tub to form a recirculating treatment water loop. Removable or permanent internal structures, within the ice container, including one or more fins and/or conductive inserts, accelerate treatment ice formation prior to use. The system is configured to promote release and upward movement of the treatment ice during melting, increasing the exposed treatment ice surface area, which improves treatment water chilling efficiency.

20 Claims, 36 Drawing Sheets

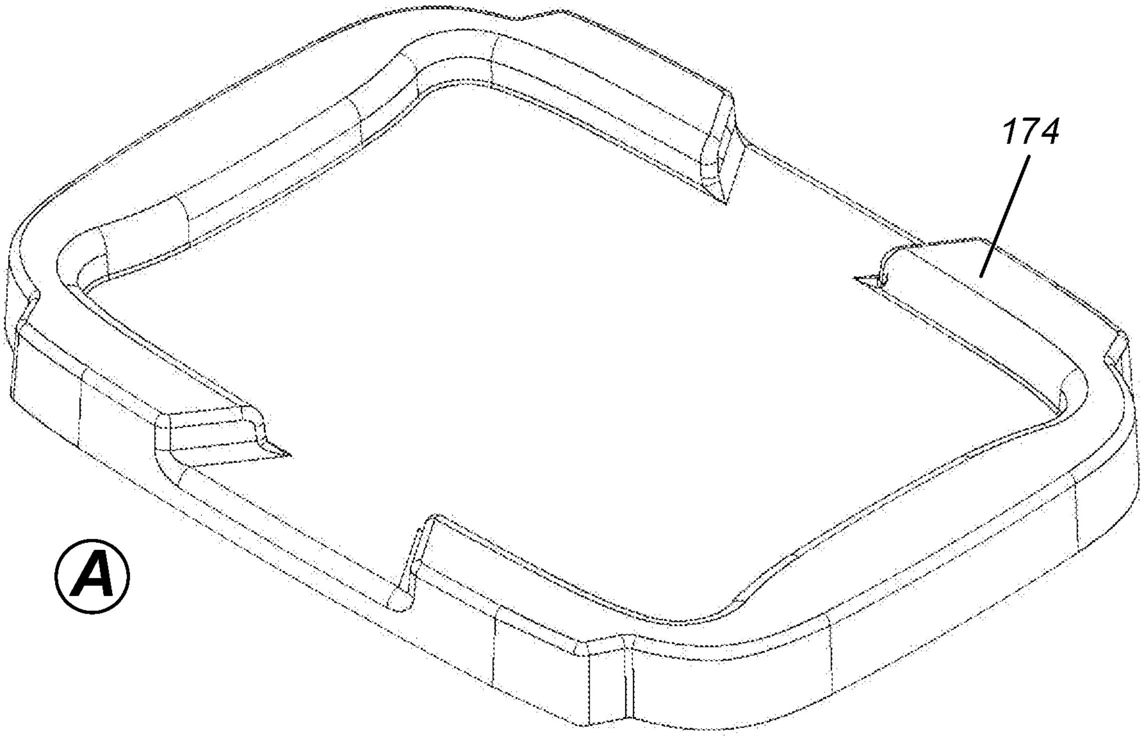
*Fig. 12F*
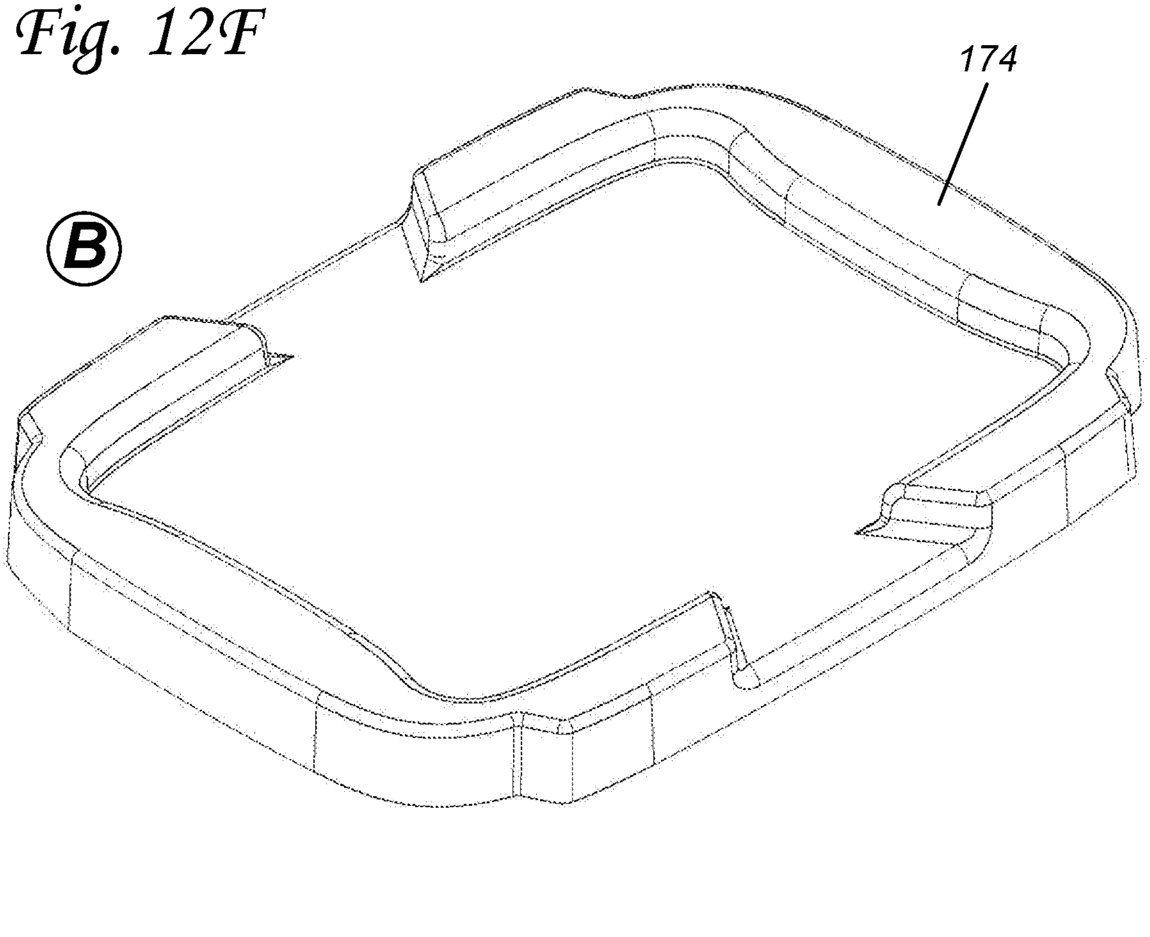

Fig. 15
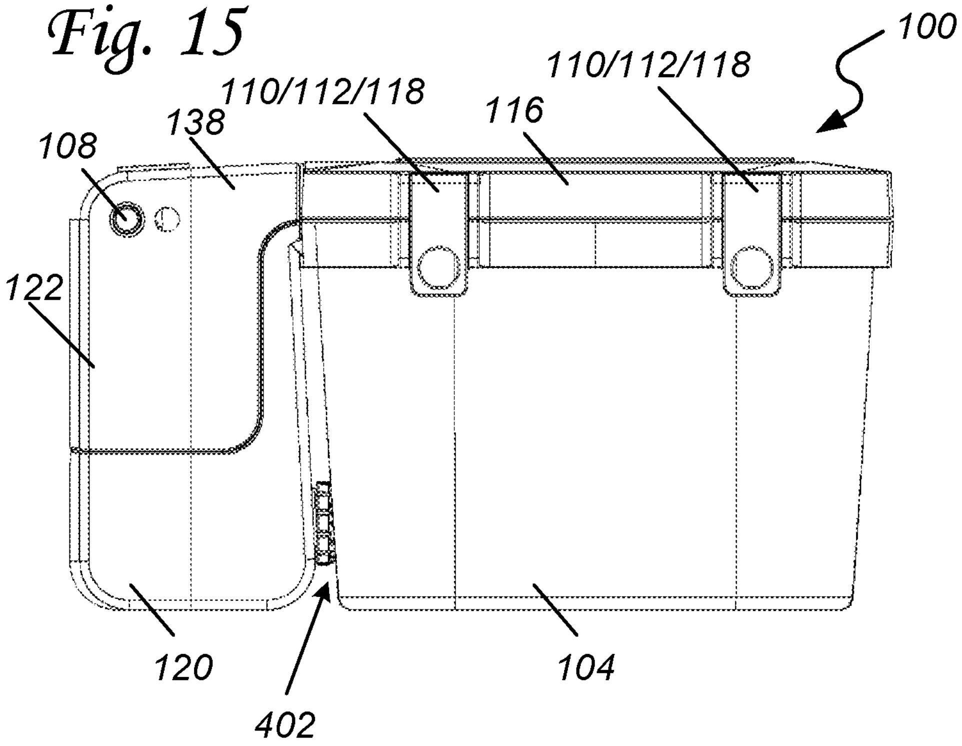
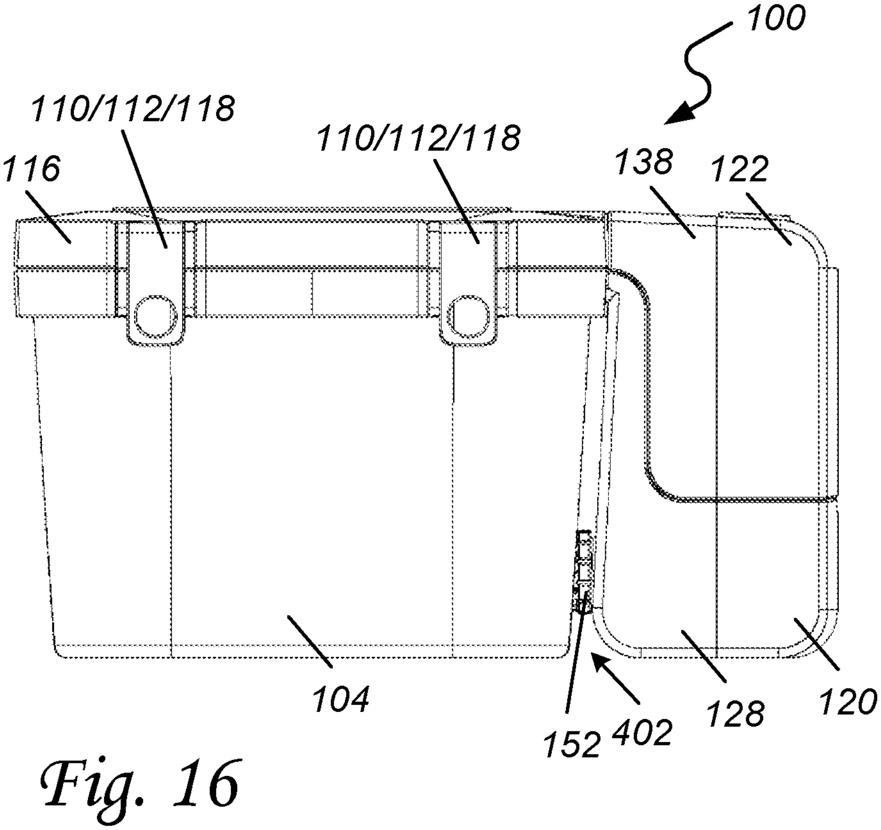
Fig. 16

ICE CONTAINER ASSEMBLY WITH IMPINGEMENT-DRIVEN CIRCULATION FOR COLD WATER IMMERSION THERAPY

CROSS-REFERENCE TO RELATED APPLICATIONS

This application contains subject matter that is related to the subject matter of the following co-pending applications. The below-listed applications are hereby incorporated herein by reference in their entirety:

This U.S. non-provisional application is a continuation in part of a U.S. non-provisional application Ser. No. 19/317,563, inventor Eric Paul Guyer et al., entitled "MODULAR SYSTEM FOR COLD WATER EXPOSURE THERAPY USING DIRECTED ICE IMPINGEMENT", filed Sep. 3, 2025;

which is a continuation in part of a U.S. non-provisional application Ser. No. 19/233,911, inventor Eric Paul Guyer et al., entitled "MODULAR COLD THERAPY SYSTEM WITH DIRECTED WATER CIRCULATION AND ICE GEOMETRY ENHANCEMENTS", filed Jun. 10, 2025, now U.S. Pat. No. 12,496,214;

which claims the benefit of a U.S. provisional application, Ser. No. 63/680,435, inventor Eric Paul Guyer, entitled "Pod or Barrels for Cold Exposure", filed Aug. 7, 2024, and a U.S. provisional application, Ser. No. 63/659,383, inventor Eric Guyer et al., entitled "Method and Apparatus for Smart, Efficient Water Therapies", filed Jun. 13, 2024.

TECHNICAL FIELD OF THE INVENTION

This invention relates to cold water exposure and immersion therapy technologies, and particularly to ice container assemblies configured to chill treatment water within a tub while a user is immersed in the treatment water. The invention further relates to ice container assemblies incorporating internal fluid channels, impingement ports, and internal ice-release structures that cooperate with circulating treatment water to enhance heat transfer efficiency. More specifically, the invention relates to ice container assemblies that accelerate the formation of treatment ice prior to use and promote controlled release and increased exposed ice surface area during use, thereby improving chilling performance in immersion-based cold water therapy systems.

BACKGROUND OF THE INVENTION

Before our invention, individuals seeking cold exposure therapy were limited to makeshift or inflexible solutions that lacked precision, usability, and scalability. Many prior approaches relied on rudimentary containers, such as bathtubs, horse troughs, or modified ice chests, filled with ice and water. These setups lacked any means of actively circulating the water, resulting in highly stratified temperatures and inefficient thermal exchange. Users would often experience uneven cooling, with warmer zones forming around the body and colder areas pooling near the ice, diminishing the overall effectiveness of the therapy.

In addition, prior approaches required constant manual intervention. Users needed to monitor water temperature, replenish ice during sessions, and determine session duration without real-time feedback or guidance. This absence of integrated control systems meant therapy results were inconsistent, with no ability to repeat or personalize the experience over time. Furthermore, because these systems typically lacked modular or sealed components, they were cumbersome to clean, awkward to transport, and prone to leaking or mechanical failure after repeated use.

Another significant limitation of earlier approaches was their inability to adapt to different user needs or environments. Whether in a residential, athletic, or clinical setting, there was no portable, self-contained option that allowed users to tailor the intensity or duration of cold therapy based on physiological cues such as heart rate or skin temperature. Nor did these approaches support integration with mobile devices or wearable technology, which increasingly form the core of modern wellness and performance ecosystems.

Safety was also a concern. Prior systems did not incorporate filtration, temperature monitoring, or flow control, and as a result, the water quality and exposure conditions were largely uncontrolled. This could introduce hygiene risks in shared-use environments or lead to overexposure and user discomfort.

The present invention addresses these and other shortcomings by providing a purpose-built, modular, and intelligent system for cold exposure therapy. For these reasons and shortcomings, as well as other reasons and shortcomings, there is a long-felt need that gives rise to the present invention.

SUMMARY OF THE INVENTION

The shortcomings of the prior art are overcome, and additional advantages are provided through the provision of an ice container assembly configured for use in cold water immersion therapy. In exemplary embodiments, the ice container assembly is configured to be positioned within a tub containing treatment water and to cooperate with circulating treatment water while a user is immersed in the treatment water.

The ice container assembly includes an ice container defining an interior volume configured to hold treatment ice, and a lid coupled to the ice container. The lid defines one or more internal fluid channels that supply treatment water to a plurality of impingement ports directed toward the treatment ice. An agitator module coupled to the lid includes a pump configured to draw treatment water from the tub and deliver the treatment water through a connecting enclosure to the internal fluid channels.

The connecting enclosure defines a streamlined internal flow path extending generally along a vertical axis and transitioning through one or more angular bends into the internal fluid channels, thereby preserving flow momentum prior to discharge. During operation, treatment water is directed toward the treatment ice to chill the treatment water, after which the chilled treatment water returns to the tub to form a recirculating treatment water loop.

Additional shortcomings of the prior art are overcome, and additional advantages are provided through the provision of an ice container assembly configured for use in cold water immersion therapy in which treatment water within a tub directly contacts a user during operation. In exemplary embodiments, the ice container assembly is positioned within the tub and defines an interior volume configured to hold treatment ice.

The ice container assembly includes a lid coupled to the ice container, with the lid defining one or more internal fluid channels that supply treatment water to a plurality of impingement ports. During use, treatment water is drawn from the tub and delivered through the internal fluid channels and impingement ports toward the treatment ice. The discharged treatment water contacts the treatment ice to chill the treatment water before returning to the tub to form a recirculating treatment water loop that continues to contact the immersed user.

Release of the treatment ice from the ice container increases the exposed surface area of the treatment ice, thereby promoting faster chilling of the treatment water within the tub during an immersion therapy session.

Additional shortcomings of the prior art are overcome, and additional advantages are provided through the provision of an ice container assembly configured for use in cold water immersion therapy and optimized for both preparation and use phases of a therapy session. In exemplary embodiments, the ice container assembly is configured to be positioned within a tub containing treatment water and defines an interior volume configured to hold treatment ice.

The ice container assembly includes a lid coupled to the ice container, with the lid defining one or more internal fluid channels that supply treatment water to a plurality of impingement ports. One or more conductive inserts are positioned within the interior volume of the ice container and are configured to accelerate the formation of the treatment ice during freezing prior to use. During operation, treatment water is drawn from the tub and delivered through the internal fluid channels and impingement ports toward the treatment ice. The discharged treatment water contacts the treatment ice to chill the treatment water before returning to the tub to form a recirculating treatment water loop.

The conductive inserts further cooperate with circulating treatment water to permit detachment and upward movement of the treatment ice during use, increasing exposed ice surface area and enhancing chilling efficiency within the immersion therapy environment.

BRIEF DESCRIPTION OF THE FIGURES

The subject matter, which is regarded as the invention, is particularly pointed out and distinctly claimed in the claims at the conclusion of the specification. The foregoing and other objects, features, and advantages of the invention are apparent from the following detailed description taken in conjunction with the accompanying drawings in which:

FIGS. 12F-12K illustrates one example of a stacking lid for use on the ice container while the treatment ice is being formed;

FIG. 15 illustrates one example of a left side view of the cooling system;

FIG. 16 illustrates one example of a right side view of the cooling system;

Figure 1:
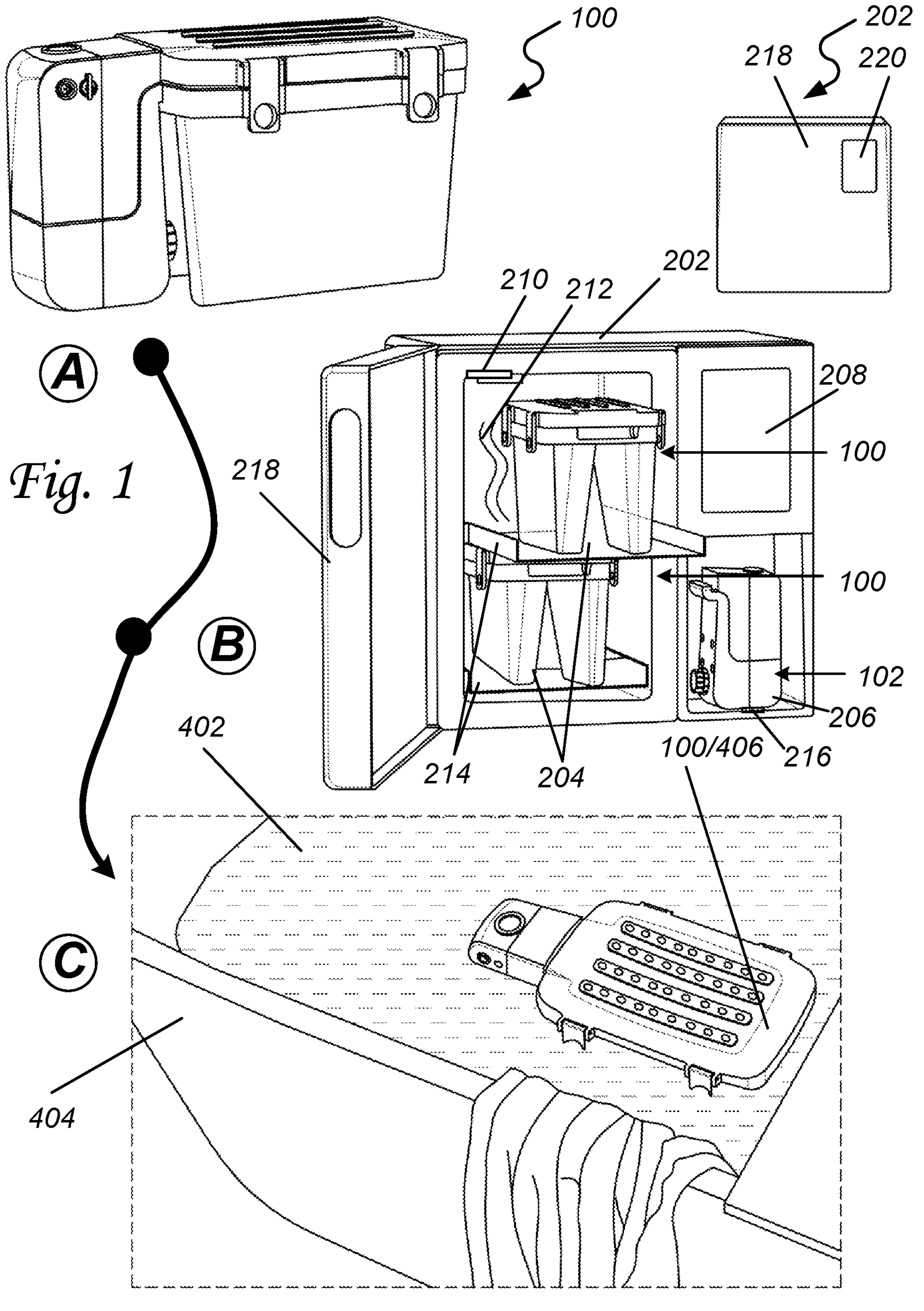
FIGS. 1-2 illustrates examples of a system for conducting temperature-controlled water exposure therapies.

The detailed description explains the preferred embodiments of the invention, together with advantages and features, by way of example with reference to the drawings.

DETAILED DESCRIPTION OF THE INVENTION

Temperature-controlled water exposure therapies, particularly cold plunges and ice baths, are widely used for their physiological and psychological benefits. These therapies have been shown to reduce inflammation, enhance circulation, shorten post-exercise recovery times, and support metabolic and neurological health. As interest in cold therapy has grown among athletes, wellness professionals, and health-conscious individuals, so too has the demand for effective, accessible systems that can deliver repeatable and safe cold-water exposure sessions.

Despite this growing popularity, the tools and methods available to conduct such therapies remain fundamentally inefficient, inconsistent, or cost-prohibitive. Traditional approaches often involve manually adding loose ice into a bathtub or water trough and waiting for the water to cool. This not only wastes time and water but also produces highly variable and short-lived temperature profiles. The rapid melt of irregular ice shapes, combined with uneven water circulation, often leads to hotspots, poor thermal penetration, and difficulty maintaining target temperatures throughout a session. For users seeking predictable and controllable exposure, such variability undermines the intended therapeutic benefits.

While some high-end commercial systems offer integrated chillers or cold plunge tanks, they are typically expensive, bulky, and limited to permanent or semi-permanent installations. These systems also rely on mechanical refrigeration loops, which can be loud, slow to operate, and energy-intensive. Moreover, few if any existing solutions are designed with modularity, personal portability, or intelligent session customization in mind. Users who wish to track progress, tailor cooling to biometrics, or run multi-user sessions in shared environments are left without meaningful technological support.

The present invention addresses these unmet needs by introducing a self-contained, modular, and data-aware chilling system capable of delivering efficient, controllable, and reusable cold therapy in nearly any setting. The core of the system is a reusable ice container designed to form a treatment ice with a finned or protruded geometry that significantly increases surface area and melting efficiency. This treatment ice can be deployed directly into a treatment tank, such as a standard bathtub or plunge basin, and interacts with a removably attached agitator module. The agitator module includes a battery-powered water pump that drives a directional water flow through one or more impingement ports. These jets are arranged and oriented to direct turbulent flow towards the treatment ice surface, accelerating melt, cooling the treatment water rapidly, and maintaining consistent temperatures during the therapy session.

A freezing and charging appliance, such as a multi-container freezing chamber, allows users to prepare multiple treatment ices while simultaneously recharging the agitator modules. The appliance may include conductive thermal ribs for enhanced freezing performance, air circulation fans to accelerate freeze times, and integrated charging stations positioned near each container location. Through this design, the invention supports rapid turnaround between sessions, quantized ice delivery, and multi-user scheduling.

To further improve functionality, the system optionally incorporates digital controls and data interfaces. A mobile application or onboard display can provide real-time temperature feedback, countdowns, or session prompts. For advanced users, the system may integrate with wearable sensors or biometric inputs, allowing the session to be optimized based on skin temperature, heart rate variability, or prior session history. Machine learning algorithms may be employed to refine future sessions based on personal response data, therapy goals, or shared anonymized user trends.

The invention is particularly advantageous for residential use, traveling athletes, wellness clinics, and rehabilitation environments where portability, reusability, and precise control are essential. Unlike fixed refrigeration systems, the disclosed solution is adaptable, cost-efficient, and designed to be recharged, reused, and redeployed with minimal setup. Whether used as a drop-in enhancement to existing tubs or as a complete modular cold therapy kit, the system brings quantized, efficient, and digitally optimized cold water therapy into a broad range of real-world settings.

In the present invention, the term "treatment ice" is intended to mean a frozen block of water formed within an ice container, optionally shaped with a finned or protruded geometry to enhance surface area, improve melt characteristics, and increase heat exchange efficiency during cold therapy sessions.

In the present invention, the term "treatment water" is intended to mean water contained within a treatment tank or chamber, which is actively circulated and cooled during a cold exposure therapy session through interaction with the treatment ice.

In the present invention, the term "agitator module" is intended to mean a modular unit that includes at least a water pump, a power source in an exemplary embodiment rechargeable, and control electronics, and is configured to circulate treatment water through the chilling system to facilitate active cooling.

In the present invention, the term "impingement port" is intended to mean a directional fluid nozzle or aperture integrated into the chilling system that delivers a concentrated stream of treatment water directly towards the surface of the treatment ice to accelerate melting and increase thermal exchange.

In the present invention, the term "fluid channel" is intended to mean the internal passage defined between an inner lid and outer lid of the chilling system, configured to direct incoming treatment water towards the surface of the treatment ice and toward an egress pathway.

In the present invention, the term "fluid channel slot" is intended to mean an outlet formed in the outer lid of the chilling system that allows chilled treatment water to exit the internal fluid channel and return to the surrounding treatment tank.

In the present invention, the term "cooling and charge chamber" is intended to mean a refrigeration appliance configured to freeze water within one or more ice containers and simultaneously charge the agitator modules via inductive or contact-based charging stations.

In the present invention, the term "fin" is intended to mean an upwardly projecting feature located on the interior bottom surface of the ice container, around which treatment ice is formed and from which the ice detaches during initial melt, improving exposure of the ice surface and accelerating chilling performance.

In the present invention, the term "water channel contour" is intended to mean a raised or contoured feature along the bottom surface of the ice container that permits treatment water to flow freely around, beneath, or through the container, promoting balanced intake flow and reducing stagnation zones.

In the present invention, the term "egress port" or "egress path" is intended to mean an opening formed in the outer lid of the chilling system through which chilled treatment water exits after passing over the treatment ice.

In the present invention, the term "controller" or "control system" is intended to mean an electronic module or circuit housed within the agitator module that governs pump operation, sensor input processing, communication with external devices, and session logic control.

In the present invention, the term "treatment tank" is intended to mean a bath, container, or other suitable reservoir configured to hold a volume of treatment water into which the chilling system and a user can be placed during a cold exposure therapy session.

Turning now to the drawings in greater detail, it will be seen that in FIG. 1, there is illustrated one example of a system for conducting temperature-controlled water exposure therapies. In an exemplary embodiment, a chilling system 100 can be inserted into a treatment tank 404 for use in a temperature-controlled water exposure therapy session. In this regard, the chilling system 100 includes an ice container 104 and a modular agitator module 102, which are operatively coupled and deployed into the treatment tank 404 filled with treatment water 402. The configuration shown enables a portable, reusable system for quickly transforming ordinary bathwater into a precisely controlled cold therapy environment.

The agitator module 102 is shown securely mounted to the end of the ice container 104 and includes an integrated water pump 124 housed within a sealed assembly. This pump 124 draws treatment water from the treatment tank 404 through a submerged inlet and delivers the water into a directed fluid circuit. The fluid circuit comprises multiple labeled flow stages: 402A indicates intake from the treatment tank 404 into the pump inlet; 402B identifies the pressurized output from the pump as it is conveyed through an internal water conduit 128; 402C represents the pressurized flow as it enters an internal fluid channel 126 positioned adjacent to the surface of the treatment ice 406 formed inside the container.

One or more impingement ports 130 are embedded within this channel structure and are oriented to direct turbulent, high-velocity water streams towards the exposed surface of the treatment ice 406. This controlled impingement promotes rapid and uniform melting, thereby accelerating thermal exchange between the treatment ice and the surrounding water. In contrast to prior approaches relying on passive thermal conduction or bulk immersion of irregular ice cubes, the directional melt pathway enabled by impingement ports 130 results in faster system responsiveness, less ice mass required, and more predictable cooling curves.

After contacting the treatment ice, the water, now significantly chilled, flows along an integrated exit path, labeled 402D, through one or more egress ports 134, also referred to as one or more egress paths 134, and fluid channel slots 136 defined within the lid structure. This returning flow is labeled 402E and ultimately re-enters the surrounding treatment tank as 402F, completing the circulation loop. Unlike prior approaches, which suffer from stagnant or layered thermal zones, this closed-loop recirculation architecture ensures continuous movement, mixing, and temperature homogenization throughout the treatment volume.

The system is configured such that the treatment ice 406 remains within the container 104 and is not freely floating in the bath. This approach helps prevent user contact with solid ice surfaces, thereby reducing thermal shock and increasing safety, particularly for long-duration or therapeutically guided exposure sessions.

Additionally, the positioning of the agitator module 102 in line with the water circuit and structurally integrated with the container 104 supports rapid assembly, alignment, and removal after use. The modular nature of the components enables easy recharging, sanitization, and re-freezing between sessions, providing logistical and hygienic benefits not achievable in older solutions.

This embodiment also provides structural separation between the electronics in the agitator module and the ice mass, reducing the risk of thermal degradation or condensation damage. In contrast to prior systems requiring external pumps or manual agitation, the present invention consolidates circulation, cooling, and control into a single drop-in platform that can be adapted to a wide range of residential or clinical environments without permanent installation.

Referring again to FIG. 1, there is further illustrated an exemplary embodiment of a cooling and charge chamber 202, which is a multifunctional refrigeration device designed to prepare and maintain both ice containers 104 and agitator modules 102 for use in temperature-controlled water exposure therapy. In an exemplary embodiment, the cooling and charge chamber 202 is configured to simultaneously freeze treatment water contained within one or more ice containers 104 into defined ice blocks, while also recharging the internal batteries of one or more agitator modules 102 stored within the same chamber.

Within the chamber 202, a plurality of thermal ribs 204 are positioned to contact or support the base or side surfaces of the inserted ice containers 104. These ribs are thermally coupled to cooling elements and serve to increase heat extraction during freezing. By maximizing the thermal contact area and focusing conduction across critical surfaces of the ice containers, the thermal ribs 204 enable faster freeze cycles and more uniform ice formation, in contrast to prior approaches relying solely on ambient convection or static contact with refrigerated shelving.

Integrated into the chamber is a charging station 206, which includes one or more inductive charging coils 216 embedded proximate to each conductive shelf 214. Each conductive shelf 214 can comprise a metal insert or thermally coated surface and is thermally linked to a cold plate or evaporator system within the chamber. When an agitator module 102 is positioned on or near these shelves, the corresponding battery-powered water pump within the module can be trickle-charged or fully recharged via inductive coupling. This eliminates the need for external cabling or manual electrical connections, improving ease of use and reducing electrical contact risks in damp environments.

The cooling and charge chamber 202 also includes a fan 210 that circulates airflow 212 within the interior volume of the chamber. This airflow 212 ensures that all container positions are evenly cooled and helps prevent thermal stratification, which can otherwise lead to inconsistent freezing performance. Circulating air additionally aids in moisture control and can reduce frost buildup inside the unit.

At the front of the device, the chamber includes a door 218, which can be either fully transparent or comprise a transparent or semi-transparent panel 220 to permit visual inspection of the freezing process. This allows a user to determine when a container is fully frozen or to verify the chamber's status without opening the door and disrupting the internal temperature.

Chamber operation is governed through an integrated set of programmable controls and display 208, which enable the user to configure and monitor the freezing and charging processes. These controls may allow for setting freeze durations, charging thresholds, or operating schedules based on container count or session demand. Unlike traditional freezers or battery docks, the unified nature of the cooling and charge chamber 202 allows both ice container and agitator module subsystems to be managed from a single programmable unit, increasing workflow efficiency and reducing equipment sprawl.

In an exemplary embodiment, the lid assembly, comprising the inner lid 114 and outer lid 116, is removably secured to the ice container 104 using a mechanically actuated latch 110 system. This latch 110 is configured to engage with structural components on the container body in a manner that ensures reliable sealing and structural stability during freezing, handling, and active use of the chilling system 100.

The latch 110 includes a movably mounted latch pin 112, which is pivotally or slidingly coupled to the latch 110 body such that it can be rotated or translated into a locking position. During assembly, the latch 110 is placed over a designated edge or lip of the lid assembly (114/116), such that the latch pin 112 aligns with a corresponding latch connector 118 formed on the upper portion of the ice container 104.

Once aligned, the latch pin 112 is manipulated into engagement with the latch connector 118, which may comprise a slot, cavity, or retention hook configured to receive and hold the pin securely. This connection prevents the lid assembly from lifting, shifting, or detaching during operation. The latch connector 118 is integrally molded or attached to the container wall and may be reinforced to withstand the tension generated by pump-driven water circulation or thermal expansion of frozen contents.

When the latch 110 is fully secured, it holds both the inner lid 114 and outer lid 116 in firm contact with the upper edge of the ice container 104. This creates a sealed boundary around the fluid channel 126, directing treatment water over the treatment ice and ensuring that internal pressure does not cause leaks or lid separation. The multi-point latch system can include several latch/latch pin/latch connector assemblies around the container perimeter to evenly distribute securing force.

To remove the lid assembly, the user disengages the latch pin 112 from the latch connector 118, allowing the latch 110 to pivot or slide open. This quick-release mechanism provides access to the container's interior for cleaning, refill, or post-session meltout, while preserving a re-sealable interface for repeatable use.

The cooperative function of latch 110, latch pin 112, and latch connector 118 provides a mechanically robust, tool-free, and water-resistant lid securing mechanism-distinct from prior approaches that rely on friction fits, screw caps, or adhesives. The ability to lock and unlock the fluid circuit without disassembling the entire system enhances both ease of use and field serviceability.

Collectively, these components allow the system to maintain a ready supply of frozen treatment ice and fully charged agitator modules, enabling repeated use throughout the day without external wiring, water connections, or additional refrigeration infrastructure. In contrast to prior approaches, which required separate refrigeration and charging stations or non-modular handling, the cooling and charge chamber 202 supports high-throughput use, modular scalability, and minimal operational overhead.

In operation, in an exemplary embodiment, FIG. 1 illustrates a use-case sequence for the chilling system 100, highlighting its preparation, charging, and deployment for cold water therapy. Reference 'A' depicts the ice container 104 in an initial fill state, where treatment water is loaded into the container prior to freezing. The container may be filled through an open lid or fill port, and is designed to define a surface-enhancing geometry, such as fins, ribs, or contours, that, when frozen, forms treatment ice 406 optimized for directional melting. Once filled, the ice container 104 is sealed and prepared for freezing.

In reference 'B', the filled chilling system 100—comprising the ice container 104 and optionally a mounted or separate agitator module 102—is inserted into the cooling and charge chamber 202. Within the chamber, the container is positioned on a conductive shelf 214 or thermal rib 204 to accelerate heat extraction and reduce freeze times. Simultaneously, the agitator module 102 is placed within the chamber on or near a charging station 206, which includes an inductive charging coil 216 configured to recharge the onboard battery of the agitator module. An airflow 212 system driven by a fan 210 circulates cold air around the chamber, promoting consistent freeze performance across multiple containers. A programmable control and display interface 208 on the front of the chamber allows the user to monitor the process or configure operational cycles. A transparent or semi-transparent door 220 permits visual confirmation of freeze status without interrupting the thermal environment.

After the treatment ice has fully formed and the agitator module is recharged, the chilling system 100 is removed from the cooling and charge chamber for deployment. Reference 'C' shows the chilling system 100 placed into a treatment tank 404 filled with treatment water 402. At this stage, the agitator module 102 is operatively attached to the ice container 104, forming a sealed fluid circuit that draws water from the treatment tank via the water pump 124, routes it through an inlet opening 140, and delivers it through one or more impingement ports 130 towards the surface of the treatment ice 406. The impingement action accelerates melting, enabling fast and efficient chilling of the surrounding treatment water. The chilled water exits through egress ports/paths 134 and fluid channel slots 136, returning to the bath and creating a closed-loop circulation process that ensures uniform temperature distribution.

This operational sequence enables a user to prepare, deploy, and reuse the chilling system with minimal manual effort or infrastructure. Unlike prior approaches requiring loose ice, external pumps, or complex fixed installations, the present system allows treatment ice and water agitation to be modularized into discrete, reusable units. This not only reduces waste and setup time but also allows for session scheduling, mobile deployment, and data-guided therapy customization.

Figure 2:
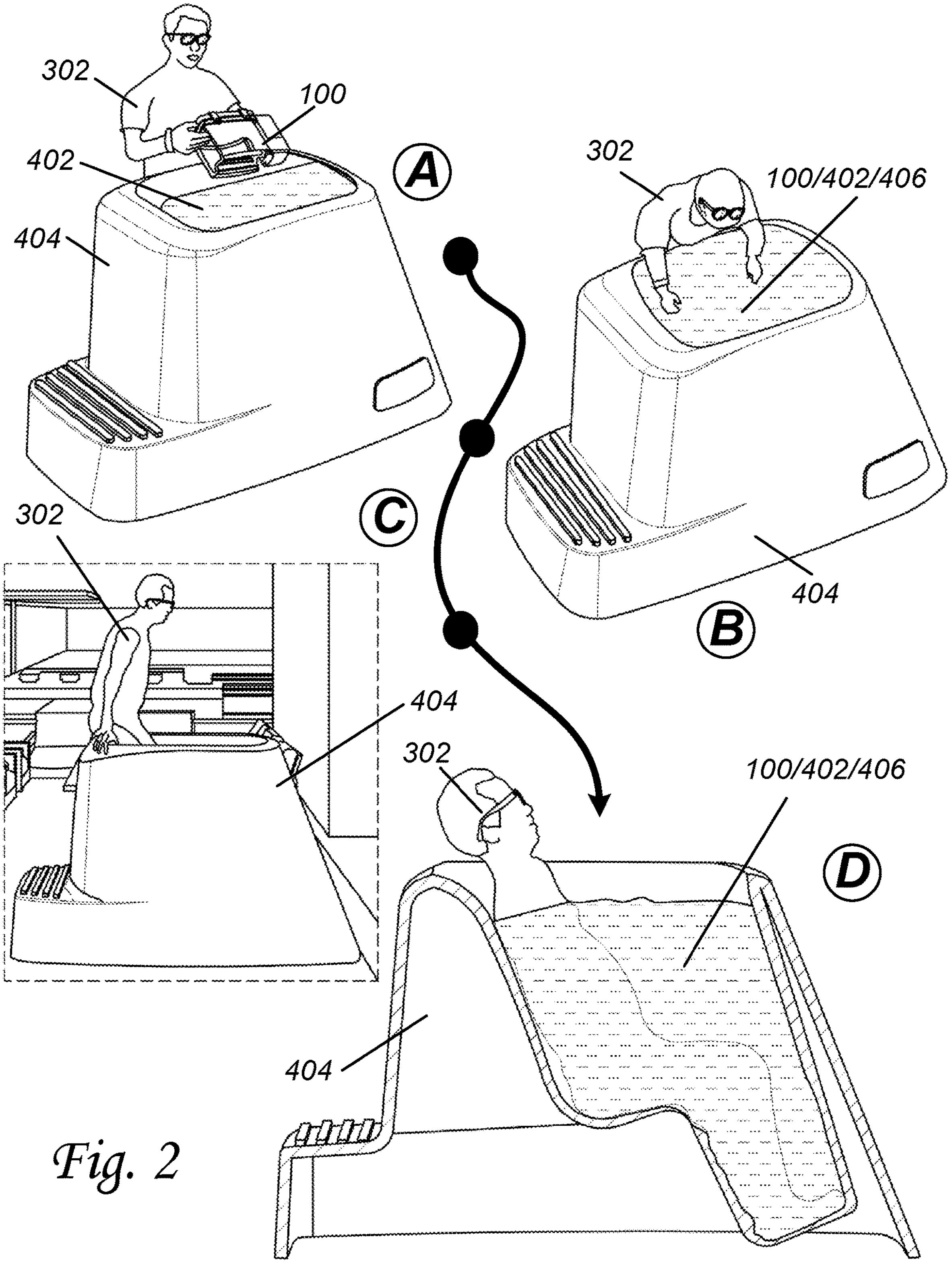

Referring to FIG. 2, there is illustrated one example of a system for conducting temperature-controlled water exposure therapies, shown through a multi-stage use case progression. In this exemplary embodiment, the chilling system 100 is deployed in a treatment tank 404, and the figure demonstrates the system's transition through key operational phases, from preparation and activation to active cooling and user immersion. This progression highlights how the system is designed to deliver consistent therapeutic performance while maintaining practical ease of use in real-world settings.

In reference 'A', a user 302 is shown manually placing the chilling system 100 into a treatment tank 404 that has been pre-filled with treatment water 402. The chilling system includes an ice container 104, preloaded with frozen treatment ice 406, and an attached agitator module 102, which contains the water pump 124 and associated control electronics. This stage represents the session preparation phase, emphasizing the portability and self-contained nature of the system. The user is able to deploy the chilling system without reliance on external plumbing, tethered power, or manual agitation, making it well-suited for both residential and professional environments. The system's compact footprint and integrated handle features facilitate quick, one-handed placement into the tub, streamlining the transition from storage to active use.

In reference 'B', the chilling system 100 is seen floating within the treatment water 402 in an active operating state. Once activated, either manually or via a mobile application or onboard interface, the agitator module 102 draws ambient treatment water into its intake using the water pump 124, circulates it internally, and ejects it through one or more impingement ports 130 aimed at the treatment ice 406 contained within the ice container 104. This creates a focused thermal exchange environment, where the turbulent flow towards the ice surface accelerates melting and chills the water far more rapidly and uniformly than passive immersion or free-floating ice blocks. Unlike prior approaches that rely on passive melting or crude agitation by hand, the chilling system 100 provides controlled, repeatable cooling performance without requiring user intervention or significant ice volume.

The floating configuration illustrated in reference 'B' enables unobstructed distribution of chilled water throughout the tub volume, creating a uniform thermal field. The structural integration of the pump, ice, and jets into a single modular unit ensures alignment and sealing of the flow path, avoiding leakage or loss of directional control. The treatment ice 406 is held within the ice container 104 and is not directly exposed to the user, reducing safety risks, prolonging melt time, and preserving the treatment water's clarity and cleanliness.

In reference 'C', the user 302 is shown climbing into the treatment tank 404 after the chilling system has sufficiently cooled the treatment water 402. Because the system operates independently and does not require repositioning, the user can enter the tub safely and comfortably. The chilling system 100 is designed with spatial clearance that allows a user to sit in the tub alongside it without interference or crowding. This approach stands in contrast to prior methods that use ice buckets or refrigeration coils, which obstruct seating areas or require repositioning once the session begins.

In reference 'D', a sectional view of the treatment tank 404 is illustrated, showing the user 302 fully immersed in the chilled treatment water 402 with their head above the waterline. The chilling system 100 remains in place and active during the session, continuing to circulate and chill the treatment water throughout. The proximity of the chilling system to the user ensures that the surrounding water remains within the target temperature range, which can be monitored and adjusted through the agitator module's internal controller or a paired mobile application. This enables time-controlled and temperature-controlled therapy, supporting protocols that require gradual cooling, sustained exposure, or pulsed circulation. The sectional view also underscores the ergonomic alignment of the user's body within the tub in relation to the chilling system, ensuring unobstructed immersion while maintaining optimal system performance.

In operation, the use-case progression illustrated in FIG. 2 demonstrates one example of how the chilling system enables a complete cold therapy cycle—from setup, to active chilling, to user immersion-using a single self-contained and reusable platform. This configuration offers significant advantages over prior approaches, which often require separate chilling devices, ice delivery, water mixing tools, or manual intervention to maintain water temperature. By encapsulating ice containment, circulation, melt acceleration, and modular recharging in a drop-in unit, the present invention achieves a balance of convenience, safety, and performance that meets the needs of both residential and professional users.

Figure 3:
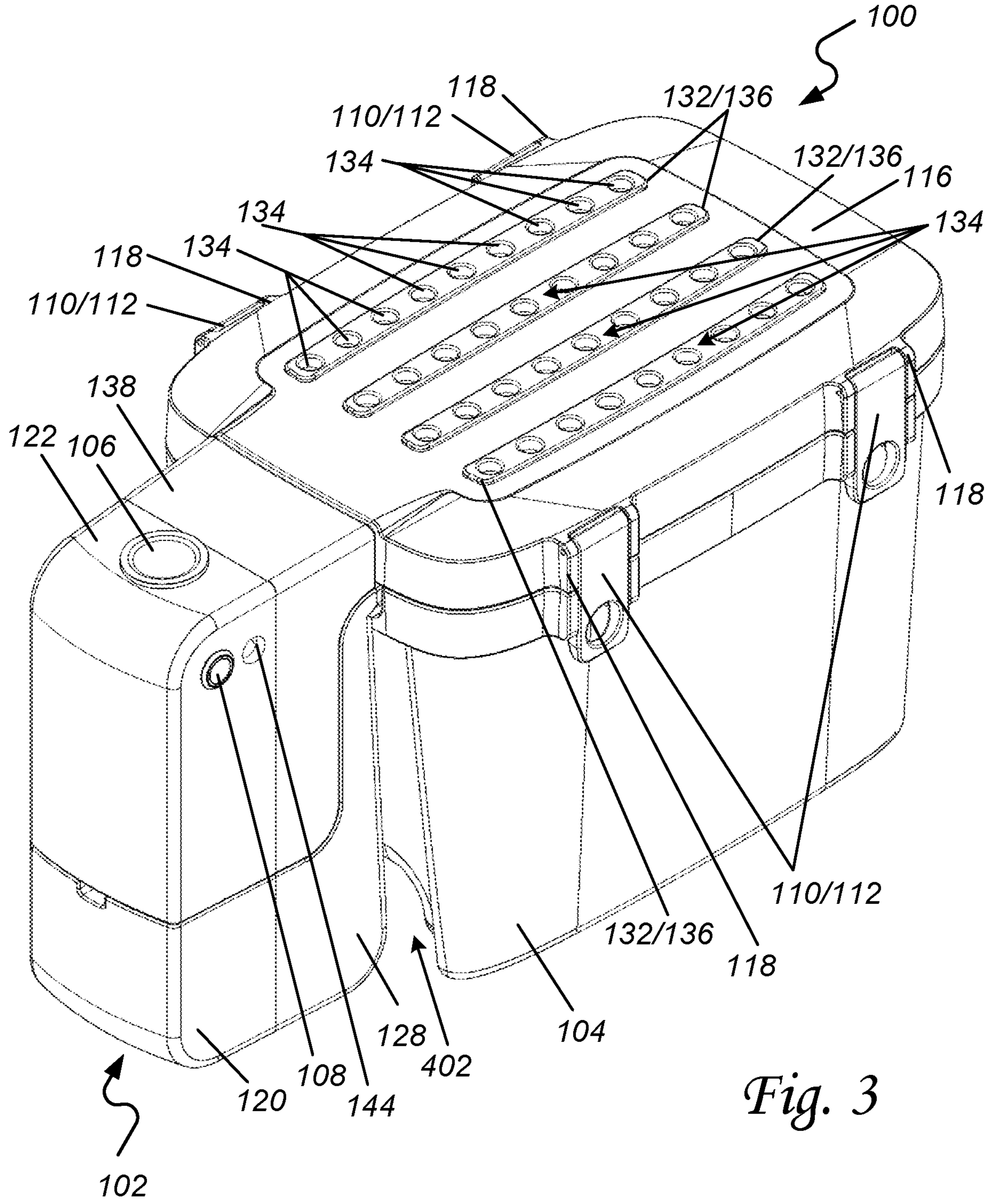
FIGS. 3-6 illustrate examples of perspective views of the top, front, back, and sides of a chilling system.

Referring to FIG. 3, there is illustrated a top perspective view of an exemplary embodiment of a chilling system 100 configured for use in temperature-controlled water exposure therapy. In this view, both structural and functional components of the system are shown in assembled form, illustrating the integration of fluid flow pathways, pump-driven circulation, and container architecture designed to support freezing, melting, and recirculation cycles in a water immersion environment.

The chilling system 100 comprises three primary assemblies: an ice container 104, an agitator module 102 that is attached at one longitudinal end of the container, and a combined inner lid 114 and outer lid 116 assembly that creates fluid flow pathways, orients impingement ports 130, and provides egress ports/paths 134 for the treatment water 402. The ice container 104 defines a primary cavity within which water is frozen into a block of treatment ice. The container is generally rectangular with contoured inner and outer geometries.

In certain embodiments, projecting upward along the bottom of the central cavity or ice container 104 can be a fin 160 is formed integrally with the base of the container 104. The fin 160 serves multiple functions. Structurally, it weakens the cohesion between the frozen ice mass and the container walls, allowing easier removal or loosening of the ice without mechanical prying or tool assistance. Functionally, it also increases surface area along the base of the ice mass, which in turn enhances melt rates during impingement or immersion. The presence of the fin is particularly advantageous during rapid cooling sessions, where directional melt can be used to accelerate thermal exchange.

The agitator module 102 is mounted at one end of the ice container 104 and includes both mechanical and electronic subsystems. In this view, a visible pump cover 120 encloses the mechanical assembly of a water pump 124, which draws treatment water 402 from the bath into a sealed water conduit 128. Adjacent to this, a controls cover 122 houses the electronic controller 500 and power source 514, such as rechargeable batteries. The modularity of the agitator 102 allows it to be detached and recharged separately from the ice container 104, facilitating reuse and extended session scheduling.

Figure 11A:
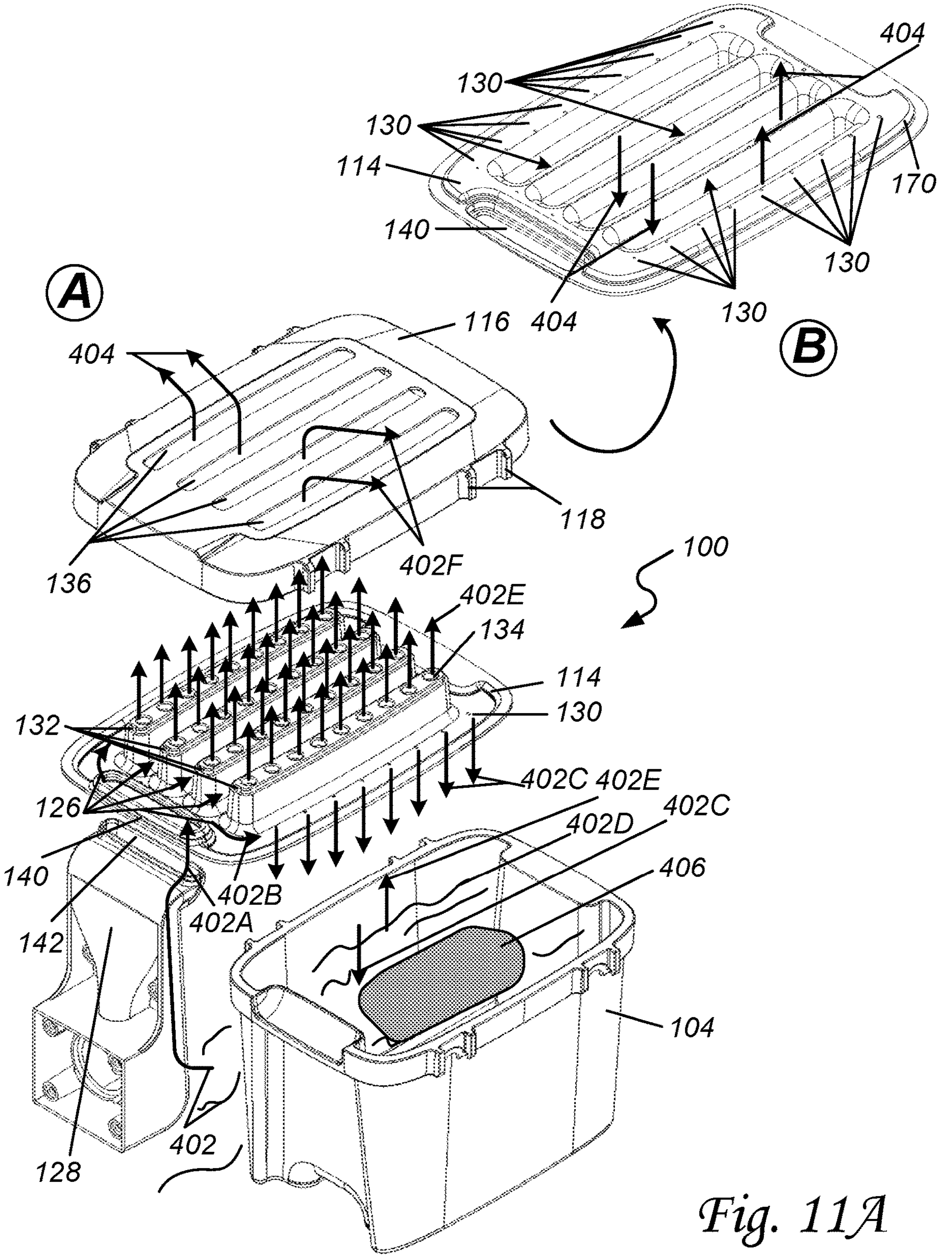
FIG. 11A illustrates one example of treatment water flow through the chilling system.

Better illustrated in at least FIG. 11A, a water conduit 128 extends from the agitator module 102 into an inlet opening 140 formed in the lid structure of the ice container 104. This water conduit 128 transfers external treatment water 402 from the pump into the internal fluid channels 126, which are defined by the structural layering of the outer lid 116 and a corresponding inner lid. These components are mechanically joined.

Toward the rear of the outer lid 116, a series of fluid channel slots 136 are shown, which serve to allow the chilled treatment water to return to the treatment tank after it has passed towards the treatment ice by way of egress ports/paths 134. These fluid channel slots 136 are formed in raised relief features along the lid surface and may include directional guides to promote even water dispersion and mixing.

Surrounding the chilling system 100 can be a partially shown volume of treatment water 402, illustrating the operating context in which the device is deployed. During operation, water from the treatment tank is drawn into the agitator module 102, circulated through the internal fluid path towards the ice, and discharged through the fluid channel slots 136 back into the treatment tank. This process creates a self-contained and highly efficient chilling cycle within a modular, drop-in device.

Unlike prior approaches relying on loose ice, passive cooling, or large fixed chillers, the chilling system 100 enables directional water movement, efficient ice utilization, and thermal regulation without the need for external plumbing or manual agitation. The top-down configuration shown in FIG. 3 emphasizes the tight integration of pumping, channeling, and melt acceleration features within a unit that is both portable and reusable.

Figure 4:
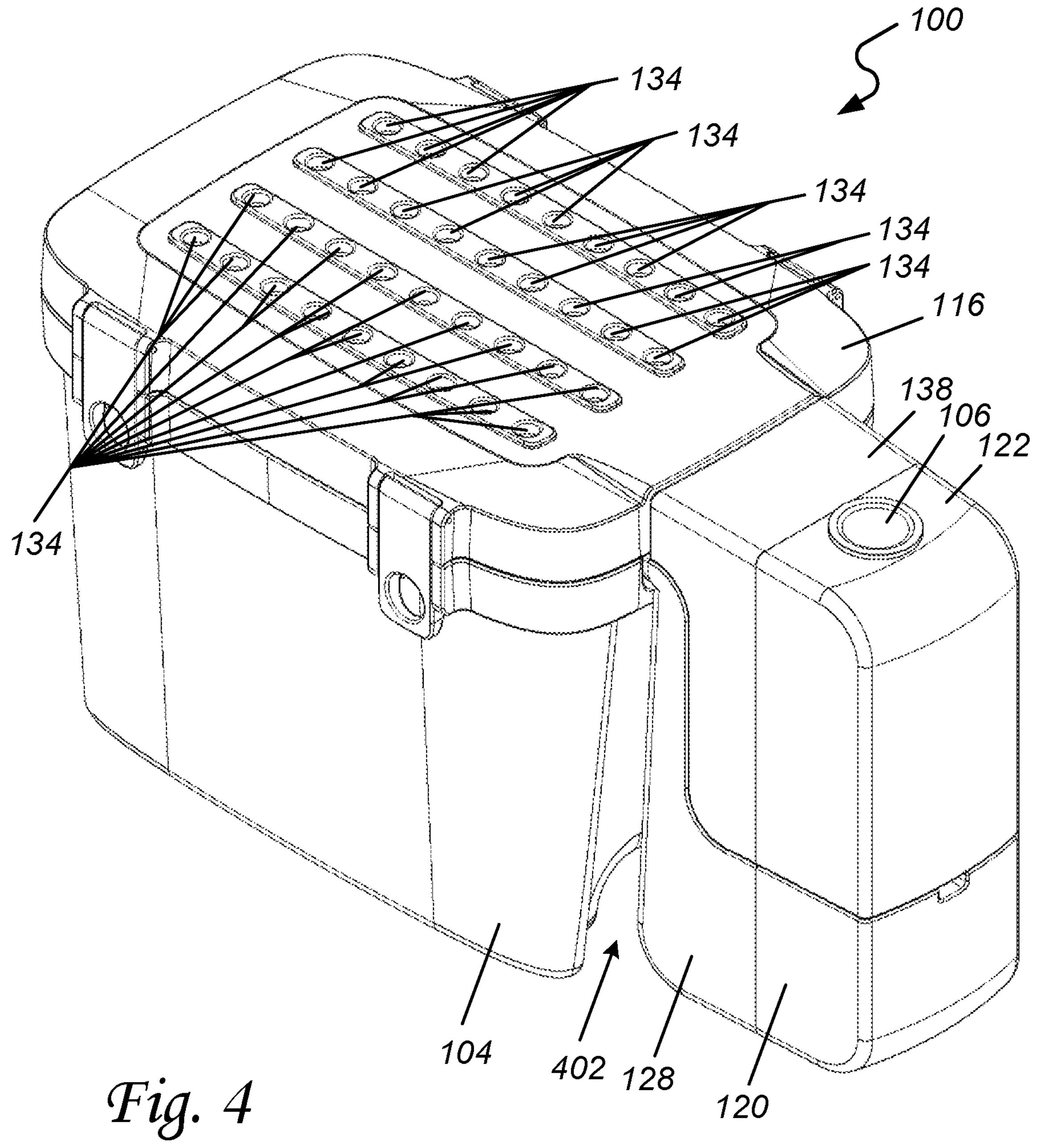

Referring to FIG. 4, there is illustrated a front perspective view of an exemplary embodiment of the chilling system 100 configured for use in temperature-controlled water exposure therapy. In this view, key structural and functional components are shown in detail, including the fluid egress system, lid assembly, and integrated pump housing.

The primary body of the chilling system is defined by the ice container 104, which holds a volume of water that, when frozen, becomes the core treatment ice used to cool the surrounding treatment tank, treatment water. Attached to the front face of the ice container 104 is the agitator module 102, which houses the water pump 124 and water conduit 128. The water pump 124 is enclosed by a pump cover 120, which is shaped to match the contours of the ice container 104 for stable attachment and sealed flow.

A top-mounted outer lid 116 is visible in this view and forms the upper boundary of the ice container's 104 internal fluid channel. Treatment water 402 can be introduced into the system through an inlet opening 140, located at the forward edge of the lid and aligned with the outlet of the water pump 124, by way of the water conduit 128, within the agitator module. The inlet opening 140 serves as the entry point to the internal fluid path between the combined inner lid 114 and outer lid 116, guiding the treatment water out through the impingement ports 130 in the inner lid 114 and towards the upper surface of the frozen treatment ice 406.

Along the rear section of the outer lid 116, a set of egress ports/paths 134 is clearly shown. These egress ports/paths are distributed across raised egress ridges 132 and are arranged to evenly discharge chilled treatment water 402 through the fluid channel slots 136 after it has circulated towards the treatment ice 406.

Figure 21:
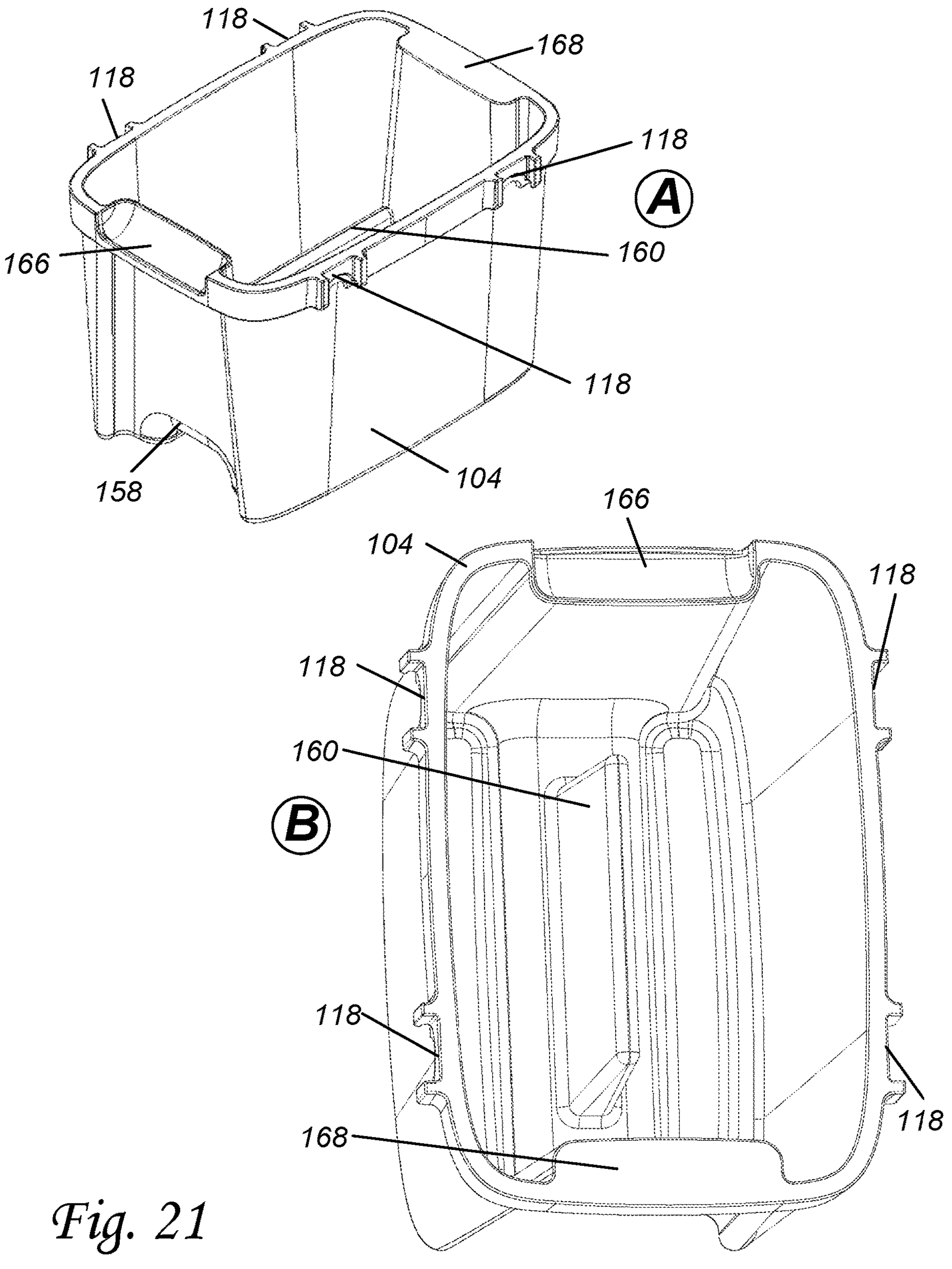
FIG. 21 illustrates one example of a perspective view of the ice container with internal view showing the fin.

Better illustrated in at least FIG. 21, a scooped handle 166 is shown projecting from the upper front edge of the ice container 104, near the agitator module 102. This handle accepts the water conduit 128 to allow treatment water to be directed between the inner lid 114 and outer lid 116 while also providing a stable gripping point for a user 302, for inserting, removing, or carrying the chilling system before and after use. Opposite the scooped handle 166, at the rear of the container, a flat handle 168 is integrated for complementary lifting or rotational positioning. The flat handle 168 forms a seal with the inner lid 114, abating treatment water from leaking at the perimeter of the ice container 104 proximate to the flat handle 168 area.

Surrounding the chilling system 100 is a portion of the treatment water 402, shown to contextualize the system's deployment in a treatment tank 406 filled with treatment water 402. As the water pump 124 drives water through the inlet opening 140, out of the impingement ports 130, and towards the treatment ice 406, the chilled treatment water 402, filling the ice container 104, exits via the egress ports/paths 134 which are configure across the top edge of the raised egress ridges 132, re-entering the surrounding treatment water within the treatment tank 406 in a controlled and distributed pattern.

Unlike prior approaches where melted ice passively cools the water with little directionality or feedback, the use of defined egress ports/paths 134, in coordination with a sealed flow path, enables precise control over the location, velocity, and dispersion of chilled treatment water 402 from the chilling system 100. This allows the chilling system 100 to maintain uniform treatment tank 406, treatment water 402 temperatures, reduce dead zones, and enable shorter cooldown cycles-all within a reusable, drop-in module.

Figure 5:
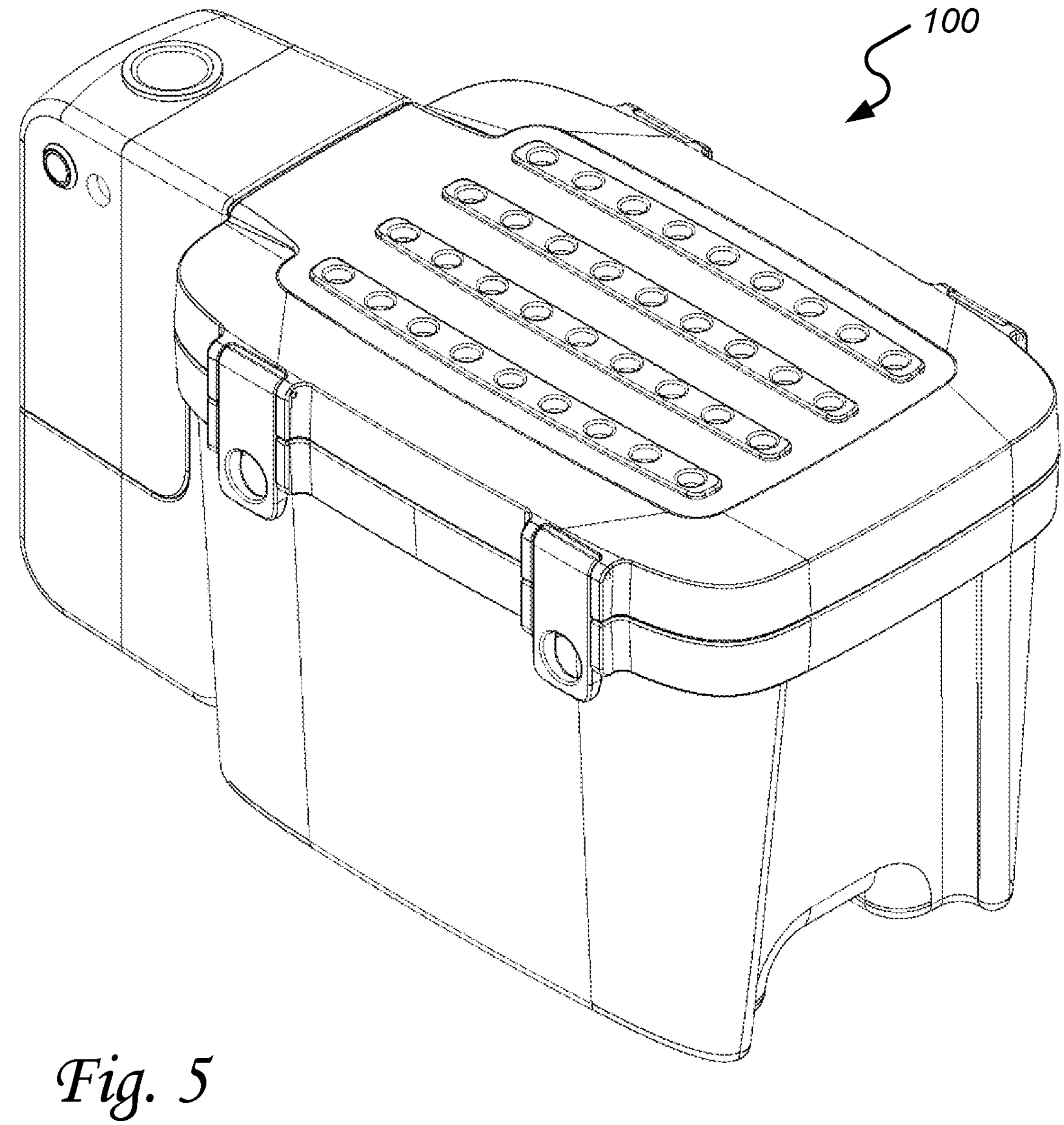
Figure 6:
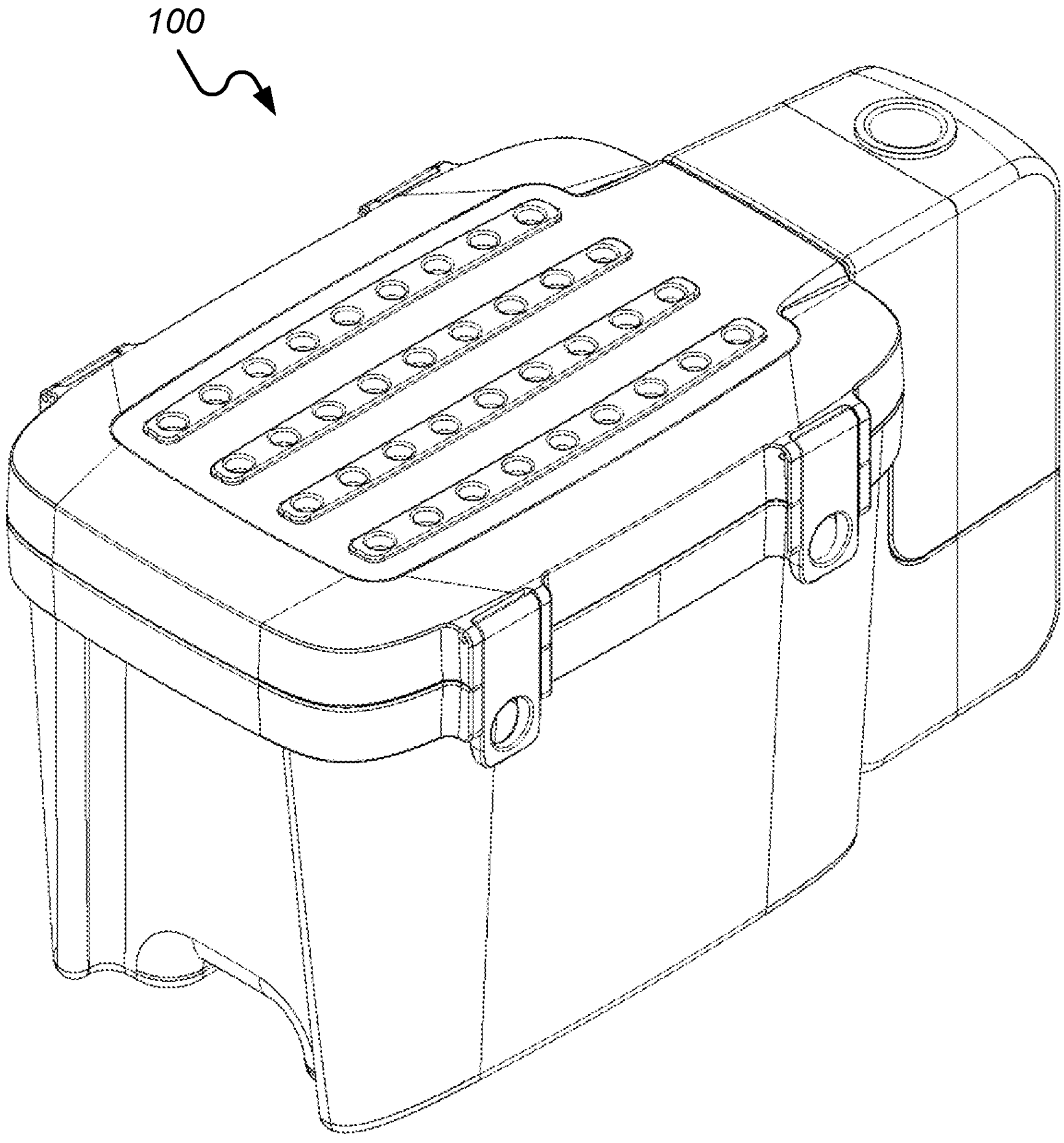

Referring to FIGS. 5 and 6, there are illustrated front perspective views of an exemplary embodiment of the chilling system 100.

Figure 7:
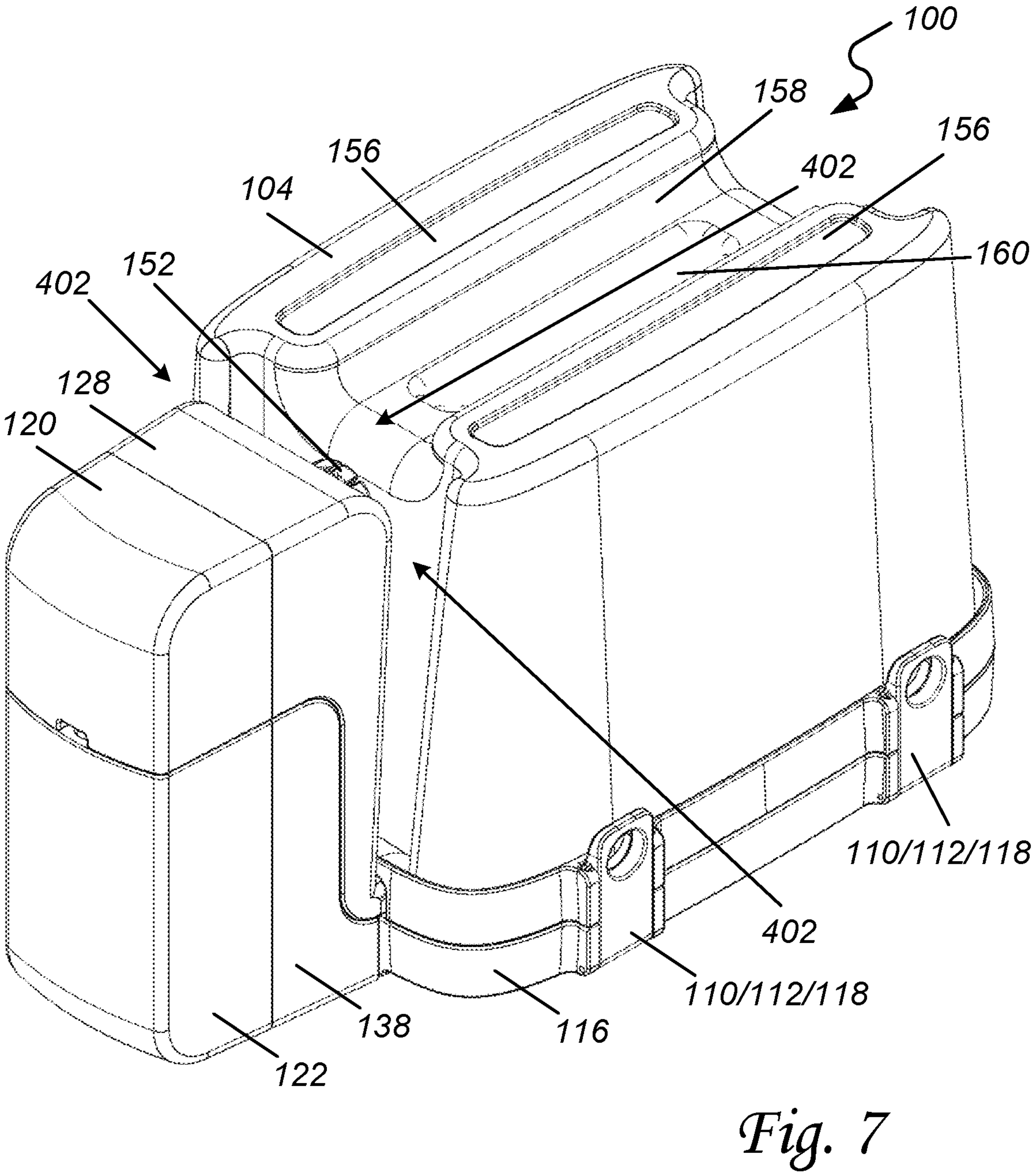
FIGS. 7-10 illustrate examples of perspective views of the bottom, front, back, and sides of a chilling system.

Referring to FIG. 7, there is illustrated a bottom and side perspective view of an exemplary embodiment of the chilling system 100 which includes an ice container 104 and an attached agitator module 102. This view reveals important underside and lateral features of the system that facilitate stable placement, directional fluid flow, and precise positioning during freezing and operation.

Visible along the bottom surface of the ice container 104 are positioning recesses 156, which are formed to engage with ridges or guides in a cooling and charge chamber 202. When the chilling system 100 is placed into such a chamber for freezing, the positioning recess 156 maintains the system in proper alignment and separation from adjacent units, allowing for optimized air circulation between containers. This airflow promotes faster and more uniform ice formation during freezing cycles.

Additionally, the positioning recesses 156 are part of the finned geometry configured to form a treatment ice 406 having a protruded or finned geometry to increase surface area and accelerate melting in treatment water.

Also visible from this angle is the bottom side of the fin 160, which protrudes upward from the interior bottom surface into the ice container 104 where the treatment ice 406 is formed. The treatment ice 406 is formed around the fin 160 during freezing. In operation, when the system is activated and treatment water 402 is circulated by the water pump 124, water impingement ports 130 begin to melt the treatment ice 406 along the top surface, and the turbulent flow melts the treatment ice 406 around the fin 160. This initiates early detachment of the ice block from the container's interior, allowing water to contact a greater portion of the ice surface more rapidly and thereby accelerating melt rate and cooling effectiveness.

The outer lid 116 is mounted to the upper edge of the ice container 104 and, together with the inner lid (not visible here), defines a sealed fluid channel 126. The water pathway is driven by the water pump 124 and delivered into the container through the inlet opening 140, which receives flow via the water conduit 128. The water conduit 128 is routed from the water pump 124 housed within the agitator module 102 and connects to the lid 114/116 structure to enable directional water movement via the impingement ports 130 towards the surface of the treatment ice 406.

The agitator module 102 is shown mounted at the forward end of the container and is enclosed by a pump cover 120 and a controls cover 122. The pump cover 120 houses and protects the internal water pump 124, while the controls cover 122 encloses the system's controller 500 and rechargeable batteries 514, shielding the electronics from moisture during immersion and operation.

Extending from the lid assembly are one or more fluid channel slots 136, which form part of the egress path for chilled water after it has circulated towards the treatment ice. These fluid channel slots 136, along with the egress ports/paths 134, guide the cooled treatment water 402 back into the treatment tank 406 for continuous thermal recirculation. The fluid channel slots 136 are shaped and oriented to reduce splash and distribute chilled treatment water 402 evenly into the surrounding environment.

In an exemplary embodiment, the latch 110, latch pin 112, and latch connector 118 are shown positioned along the lateral sides of the ice container 104, where they interface with the lid assembly, which includes the outer lid 116. In this rear and bottom perspective, the latch components are visible in their closed or operational orientation, illustrating how they are distributed around the container to provide multi-point securing of the lid structure.

The latch 110 is seen mounted externally to the lid assembly and extends downward along the container's sidewall where it aligns with the fixed latch connector 118 on the body of the ice container 104. The latch pin 112, though partially obscured in this view, is retained within the latch housing and seated into the connector structure, completing the mechanical lock. Their position on both sides of the container ensures symmetrical load distribution during transport, freezing, and pump-driven circulation.

This figure further illustrates how the latch hardware is flush-mounted or recessed into the container and lid surfaces, minimizing interference with the container's positioning recess 156 or structural base perimeter 152. The low-profile configuration also prevents snagging when the chilling system 100 is placed into a cooling and charge chamber 202 or submerged into a treatment tank 404 filled with treatment water 402.

Although the internal engagement function of the latch components is best appreciated in other views, FIG. 7 emphasizes their external orientation and shows how the latch system is designed to withstand environmental exposure, water immersion, and freeze-thaw cycles without compromising mechanical integrity or seal retention. The materials and placement are optimized to avoid accidental release or corrosion, making the assembly robust and maintenance-friendly even after repeated sessions.

Figure 8:
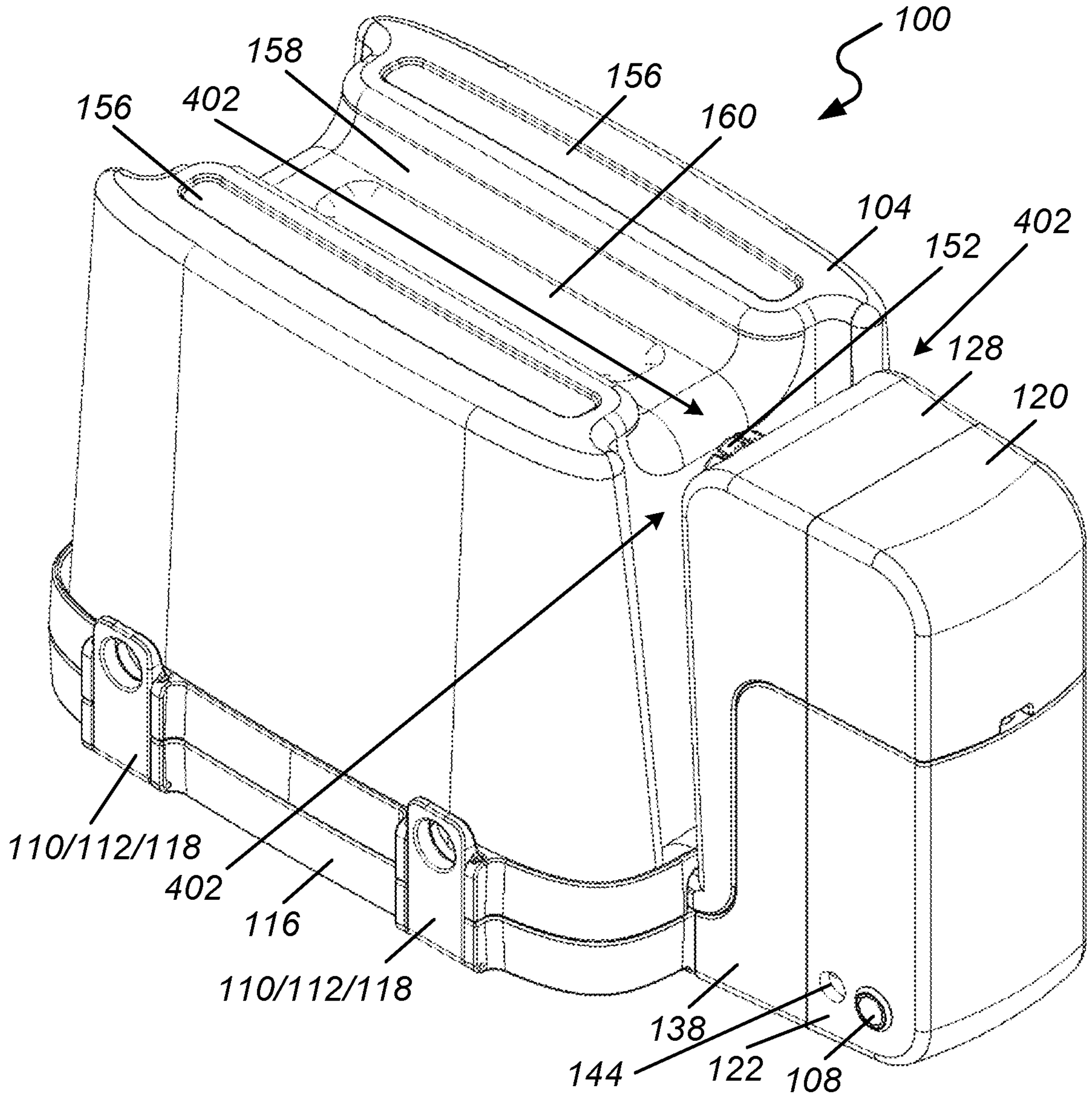

Referring to FIG. 8, there is illustrated a bottom and angled perspective view of an exemplary embodiment of the chilling system 100 comprising an ice container 104 and an attached agitator module 102, submerged in treatment water 402. This view reveals key interface elements and support structures that enable water circulation, system alignment, and efficient melt behavior during a cold exposure therapy session.

The underside of the ice container 104 is shaped to optimize fluid dynamics and mechanical stability. A water channel contour 158 is visible along the bottom surface. This contour forms a raised passage that allows treatment water 402 to flow unimpeded along the exterior surface of the container between its front edge and the region surrounding the inlet filter 152. This geometry promotes diverse and multi-directional intake of treatment water from both the front and rear of the system, enhancing flow balance and drawing water efficiently toward the pump 124 within the agitator module 102.

The fin 160 is positioned on the interior bottom surface of the ice container 104, protruding upward into the ice-forming cavity. In operation, treatment ice 406 is frozen around this fin. When the system is activated and impingement ports 130 direct circulating treatment water onto the ice surface, the melting process begins around the fin. This initiates early detachment of the treatment ice from the container's inner surface and increases the effective surface area exposed to water flow, accelerating thermal transfer and improving session responsiveness.

The positioning recess 156 traverses the underside of the container and is designed to engage ridges or supports within a cooling and charge chamber 202 during freezing. This recess keeps the system precisely aligned during cold air circulation, minimizing freeze time by ensuring adequate spacing and airflow between adjacent containers stored in parallel.

Mounted at the forward end of the container is the agitator module 102, which is enclosed by a pump cover 120 and a controls cover 122. The pump cover 120 houses and protects the system's internal water pump 124, while the controls cover 122 contains a controller 500 and rechargeable battery 514 used to manage the pump's operation. The front face of the controls cover includes a mode select button 108, allowing the user to select among operational modes such as low, medium, or high agitation rates depending on session preferences. Adjacent to this is a status indicator 144, which provides a visual signal-via LED or similar indicator—of system readiness, pump activity, or battery status.

Also visible is the connecting enclosure 138, which fastens the agitator module components together by linking the pump cover 120, controls cover 122, and the water conduit 128. The conduit terminates at the water conduit outlet 142, which aligns with the inlet opening 140 on the container lid and directs the pumped treatment water into the fluid channel 126 formed between the inner lid 114 and outer lid 116 (not fully visible in this view).

While the internal melt and flow dynamics are not shown in this perspective, the structural view of FIG. 8 clearly illustrates how the bottom and front geometries of the system work in concert to support stable immersion, directed intake, and melt acceleration. The modular and sealed architecture of the chilling system 100 allows it to operate entirely submerged without external connections, making it suitable for residential tubs or professional therapy environments.

Figure 9:
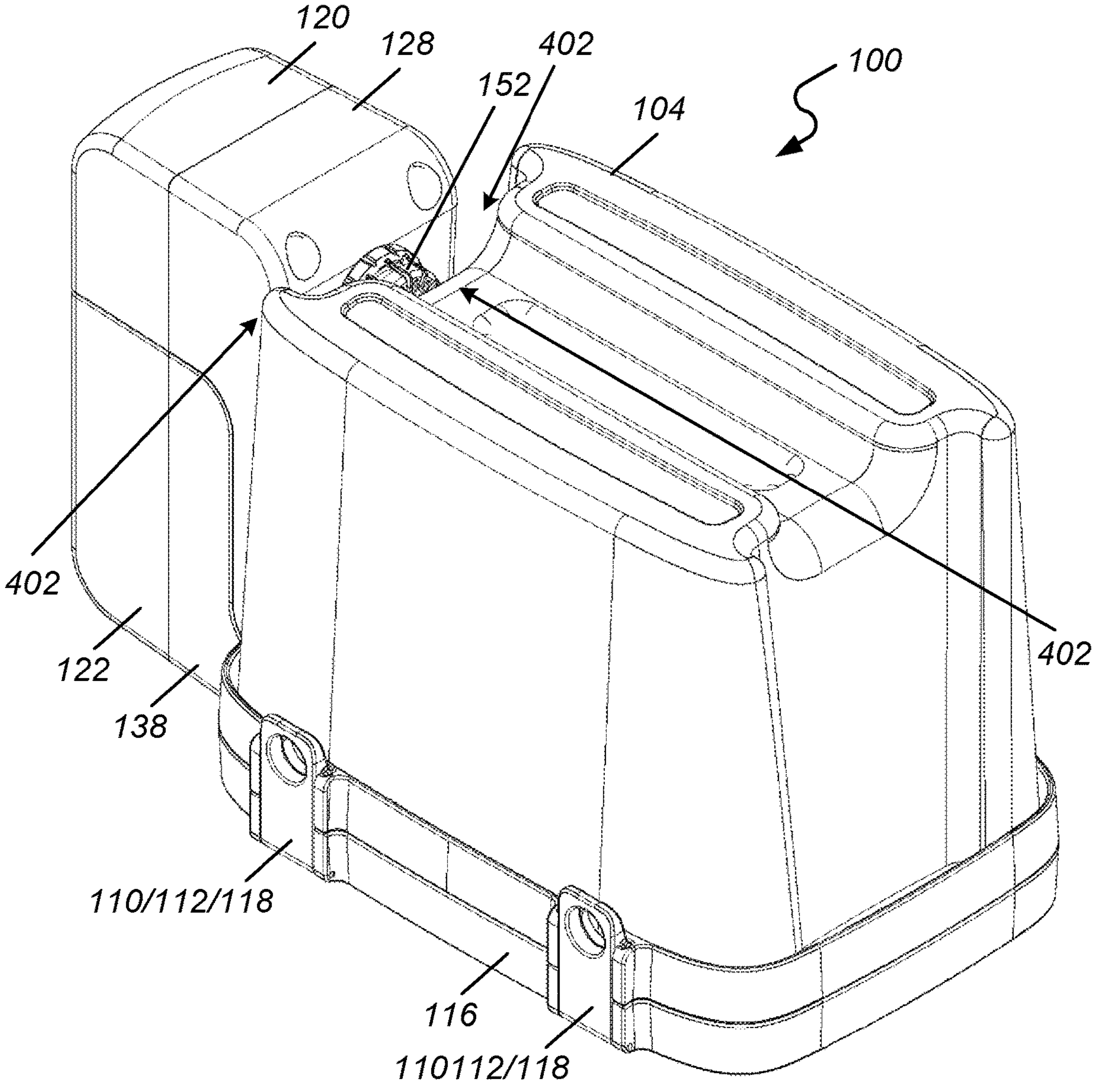

Referring to FIG. 9, there is illustrated a bottom and side perspective view of an exemplary embodiment of the chilling system 100 showing the interconnection of structural and fluidic elements that support cold water therapy operation. The chilling system 100 includes an ice container 104 coupled to an agitator module 102, with key components of the lid and pump interface visible from this angle.

Positioned atop the ice container 104 is an outer lid 116, which in conjunction with an inner lid 114, defines a sealed fluid channel 126 used to direct treatment water 402 towards frozen treatment ice 406 during operation. The outer lid 116 is mechanically secured to the container using a multi-point latch assembly. In this view, a latch 110 is shown mounted along the lateral edge of the lid assembly. The latch 110 includes a movable latch pin 112, which engages a latch connector 118 integrated into the body of the ice container 104. This engagement securely locks the lid in place, maintaining proper sealing and alignment during high-velocity water circulation and freezing cycles.

The agitator module 102 is affixed at the forward end of the container and is formed from several interlocking enclosures. The pump cover 120 houses water pump 124, which draws in treatment water 402 from the surrounding environment. Adjacent to it, the controls cover 122 enclose the system's controller 500 and power source 146, which can be a rechargeable power source. These covers are mechanically joined by a connecting enclosure 138 (not visible in this view), forming a cohesive and water-resistant pump assembly.

Running along the side of the agitator module 102 is a water conduit 128, which transports pressurized treatment water from the pump to the lid. This conduit terminates at the inlet opening 140, allowing the water to enter the internal fluid channel formed above the treatment ice 406. From there, treatment water 402 is routed through impingement ports 130 onto the surface of the treatment ice 406 and then returned chilled through an egress port/path 134 array to the surrounding treatment water 402.

Also visible in this view is the inlet filter 152, positioned on the side of the agitator module 102 proximate the side of the ice container 104. The inlet filter 152 is configured to screen treatment water 402 before it enters the water pump 124, helping to prevent debris from entering the fluid system. The inlet filter 152 is sealed in place by an inlet filter seal 154, which prevents leakage or bypass around the inlet filter 152 interface.

FIG. 9 further illustrates the compact and modular arrangement of the chilling system 100. The water pump 124, control electronics 500, inlet filter 152, and fluid delivery pathways are all self-contained within the agitator module 102, which removably mounts to the ice container 104 without tools or exposed cabling. The sealed architecture, mechanical latching system, and inline water conduit enable a highly portable and repeatable cold therapy system that improves upon prior approaches relying on loose ice, manual mixing, or non-integrated components.

Figure 10:
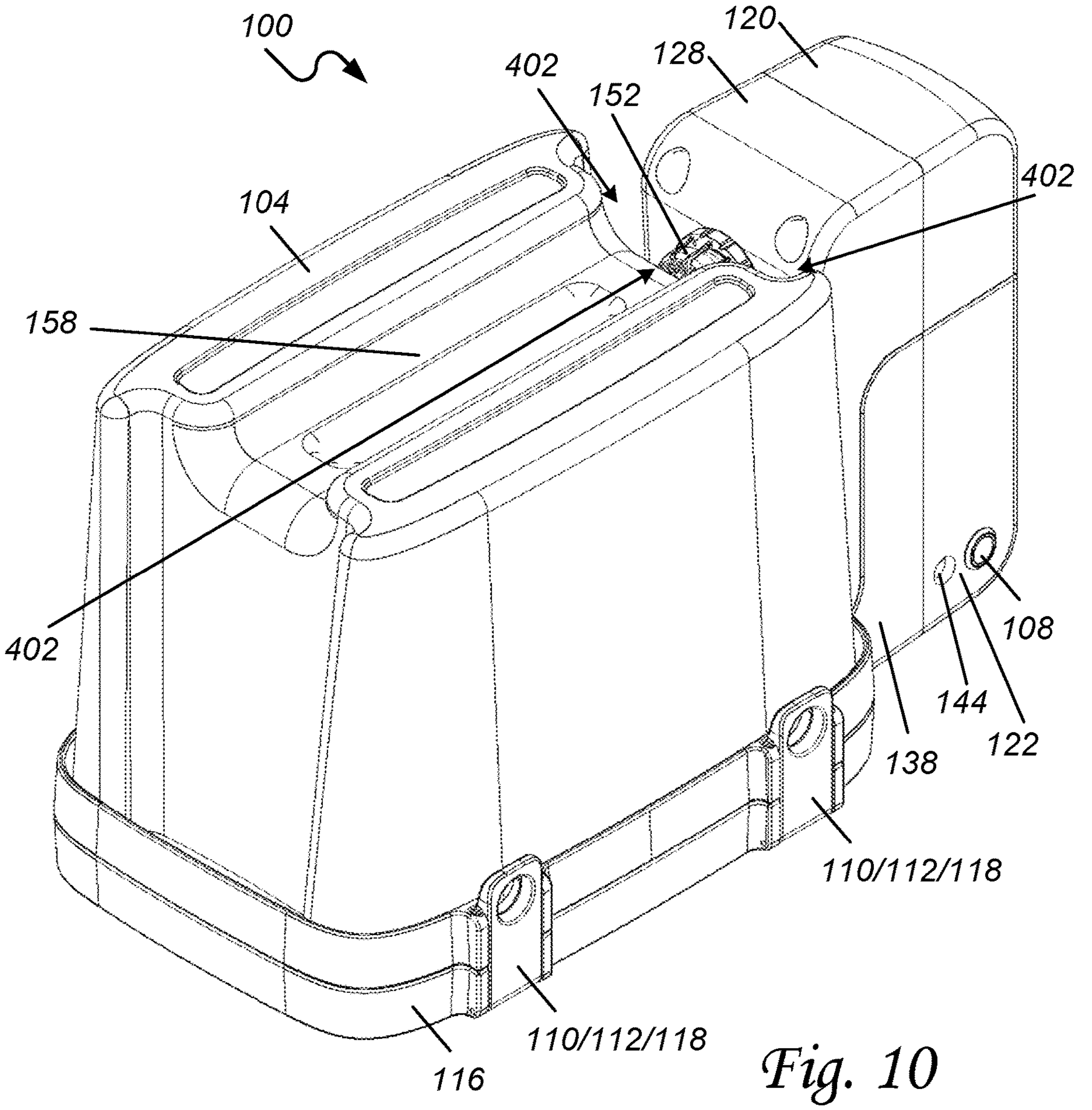

Referring to FIG. 10, there is illustrated a side perspective view of an exemplary embodiment of the chilling system 100 comprising an ice container 104 and a coupled agitator module 102. This view highlights the interaction between mechanical fasteners, fluidic pathways, user interface controls, and support structures, as integrated into the side profile of the system.

The agitator module 102, positioned at the back end of the ice container 104, is enclosed by a pump cover 120 and a controls cover 122, which protect internal components such as the water pump and rechargeable power source. On the outer face of the controls cover 122, a mode select button 108 is visible, allowing the user to toggle between operational modes such as low, medium, or high agitation. Adjacent to the button is a status indicator 144, which provides a visual output, such as an LED, to communicate readiness, power level, active operation of the chilling system 100, or other status conditions.

A water conduit 128 is shown exiting the pump housing, routing pressurized treatment water 402 toward the inlet opening of the lid assembly 114/116. This water conduit 128 forms part of a sealed fluid loop that ensures consistent directional water flow 402 towards the treatment ice 406 during use.

The top of the ice container 104 is sealed with an outer lid 116, which is part of a two-part lid assembly 114/116 that defines the upper fluid circulation channel. The lid is secured to the container using a mechanically locking latch 110, which is mounted along the side of the system. A latch pin 112 projects from the latch and engages with a corresponding latch connector 118 molded into the container wall. This latch interface prevents the lid from separating under internal pressure or fluid movement and supports easy removal for refilling or maintenance.

Beneath the agitator module 102, a suction-mounted inlet filter 152 is visible. This inlet filter 152 is positioned to screen incoming treatment water and prevent particulates from entering the pump system. It is integrated into the base of the agitator and works in tandem with an inlet filter seal 154 to ensure clean, leak-resistant operation during submerged use.

The lower portion of the ice container 104 includes a water channel contour 158, formed as a recessed external or raised internal feature that runs along the underside of the container. This structure contributes to a finned geometry configured to form a treatment ice having a protruded or finned geometry to increase the surface area and accelerate melting in treatment water 402 and allows treatment water 402 to flow around and beneath the container body, enhancing intake fluid dynamics and ensuring water from all directions, including front and rear, is drawn into the inlet filter 152. This design minimizes stagnant zones and improves temperature uniformity throughout the treatment tank.

Referring to FIG. 11A, there is illustrated one example of treatment water flow through the chilling system 100 emphasizing the internal treatment water flow path during operation. The figure shows the chilling system placed within a treatment tank 404 filled with treatment water 402, and reveals how the directional flow of treatment water 402A-402F is managed through the device to achieve efficient chilling performance and high thermal contact with the treatment ice 406.

The chilling system 100 includes an ice container 104, into which the treatment ice 406 is pre-frozen. Affixed to the front of the ice container is the agitator module 102, which includes a water pump 124 configured to draw in ambient treatment water from the treatment tank 404. Upon activation, the water pump 124 initiates the water flow sequence beginning with flow path 402A, which represents the intake of treatment water from the surrounding tub into the water conduit 128.

The treatment water 402A is routed through the water conduit 128 and delivered into the inlet opening 140, which feeds treatment water 402B directly into sealed internal fluid channels 126 formed between the inner lid 114 and outer lid 116. Once in the fluid channels 126, the treatment water 402B is distributed across the inner lid 114 in flowpaths 126/402B, traveling laterally and uniformly above the treatment ice 406.

From the fluid channels 126, the treatment water 402C is expelled through a series of impingement ports 130. These impingement ports 130 are strategically oriented and can include turbulence-enhancing geometries to direct concentrated streams of water directly downward onto the treatment ice 406. This action rapidly removes thermal energy from the circulating treatment water 402C by leveraging the large surface area of the treatment ice 406 and initiating aggressive melt at high-contact locations.

The result of this impingement is shown as flow path 402C/402D, where the treatment water is rapidly chilled upon contact with the ice. The chilled water accumulates within the ice container 104, filling the space around the melting ice. The flow of treatment water 402D is then guided upward through a series of raised egress ridges 132 formed into the inner lid 114. The raised egress ridges 132 streamline the upward movement of chilled treatment water 402D, encouraging complete distribution across the lid assembly 114/116 and avoiding stagnation.

After rising through the raised egress ridges 132, the chilled treatment water 402E exits the container through egress ports/path 134 and then exits fluid channel slots 136 shown as treatment water flow 402F. The fluid channel slots 136 are formed in the outer lid 116. These ports 134 and slots 136 return the chilled treatment water 402F into the surrounding treatment water 402 in the treatment tank 404. This closed-loop flow system ensures a continuous, recirculating exchange of water between the ice surface and the bath, maximizing chilling efficiency and maintaining uniform water temperature throughout the user's immersion.

The entire flow path, from intake 402A to discharge 402F, is fully enclosed within the chilling system 100, eliminating the need for external hoses, pumps, or ice circulation. This design provides not only improved safety and portability but also a repeatable, clean, and efficient cold therapy process that far exceeds the limitations of prior approaches, which often relied on passive convection, stagnant ice blocks, or unstructured melting without directional flow.

The directional flow system illustrated in FIG. 11A thus represents a significant advancement in water exposure therapy, offering a sealed, reusable, and thermally optimized solution that allows precise control over cooling rates and flow patterns-all housed within a single integrated module.

Figure 11B:
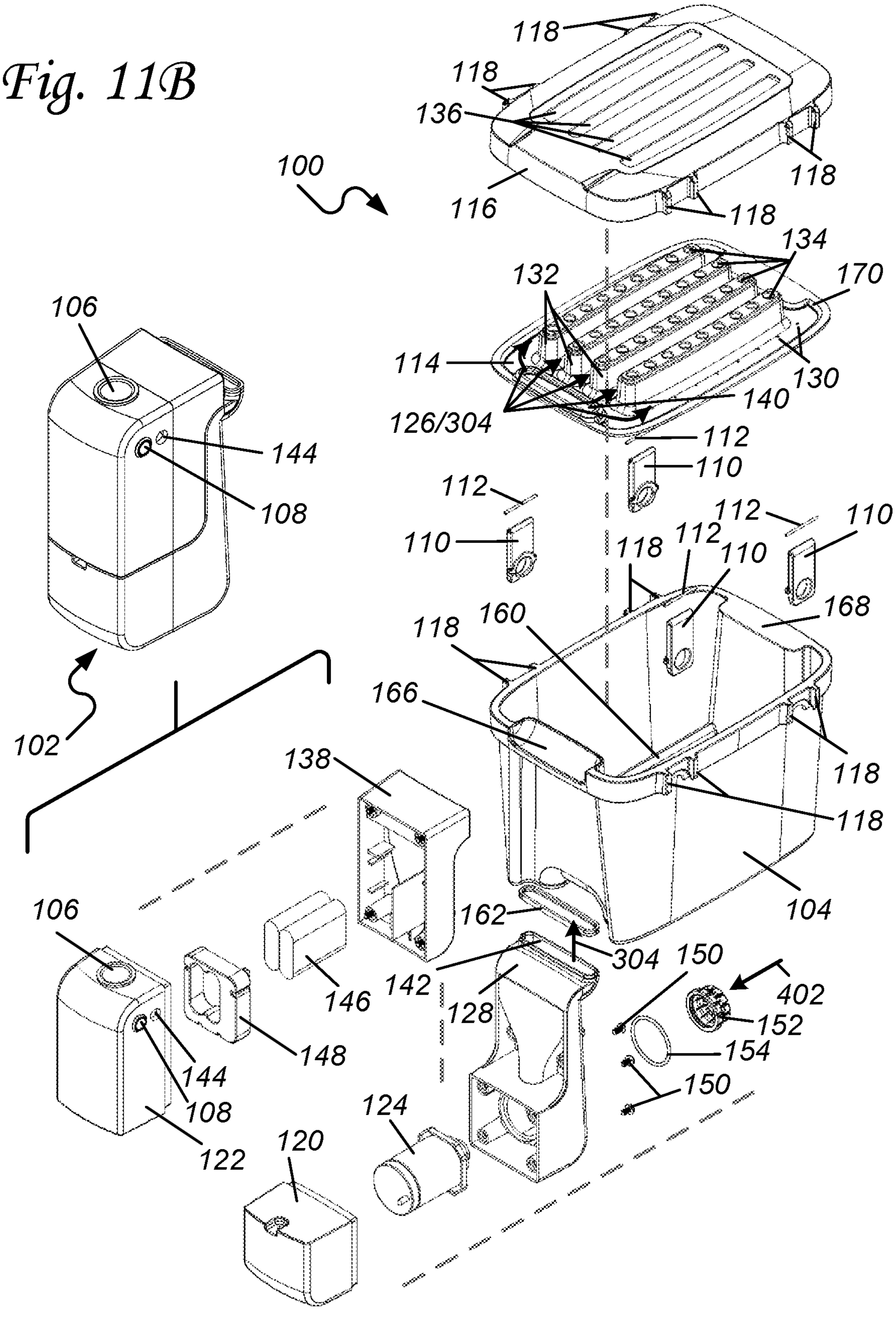
FIG. 11B illustrates one example of an assembly diagram of the cooling system.

Referring to FIG. 11B, there is illustrated an exploded assembly diagram of an exemplary embodiment of the chilling system 100 showing the mechanical and fluidic relationships between each component prior to assembly. In this view, the core subsystems including the agitator module 102, the ice container 104, and the lid assembly 114/116—are shown in disassembled form, revealing how the chilling system 100 is modularly constructed for reuse, maintenance, and efficient operation.

At the base of the assembly is the ice container 104, which defines the primary ice-holding volume where treatment ice 406 is formed. The container includes an internal cavity shaped to define a surface-enhancing ice profile and incorporates several structural features that contribute to flow control and integration with other components. A fin 160 is visible at the interior bottom surface and promotes rapid melt initiation. The fin 160, as well as other features, are part of a finned geometry that forms in the treatment ice 406, a protruded or finned geometry that increases surface area to accelerate melting in treatment water 402.

Additionally, molded into the container wall are latch connectors 118, which provide locking engagement points for the latches 110 used to secure the lid assembly.

The lid assembly comprises an inner lid 114 and an outer lid 116, which mate together to define internal fluid channels 126. The fluid channels 126 receive and distribute treatment water 402 towards the treatment ice 406, by way of impingement ports 130, during operation. The inner lid 114 includes a set of raised egress ridges 132, which are configured to channel upward-moving chilled treatment water 402 toward designated discharge egress port/path 134 locations. The outer lid 116 includes a corresponding set of fluid channel slots 136 that align with the egress ridges 132. When the lids 114/116 are mated, each egress ridge 132 protrudes through its respective slot 136. This configuration permits treatment water 402 that has passed over and around the treatment ice 406 to rise up the ridges 132 and be discharged through the slots 136, returning chilled treatment water 402 back to the treatment tank 404 in a controlled, structured flow path.

The lid assembly is secured to the ice container 104 using a latching system. Each latch 110 includes a latch pin 112 that is movably coupled to the latch body and engages one of the latch connectors 118 on the container. This creates a secure mechanical connection that can be manually locked and released, ensuring watertight sealing during use and easy disassembly for cleaning or refilling.

An agitator module 102 can be attached to the ice container 104. The agitator module 102 delivers water circulation and control functionality. The agitator module 102 can be formed from three interlocking housings: the pump cover 120, which encloses the water pump 124; the controls cover 122, which protects the controller 500 and power source 514, which can be a rechargeable battery; and the connecting enclosure 138, which joins the housing components and structurally integrates treatment water 402 pathway, which uses water pump 124, and control electronics 500, including power switch 106 configured to start and stop the agitator module 102, mode selection button 108, and status indicator 144.

In operation, treatment water 402 can be drawn into the agitator module 402 through the inlet filter 152, which is sealed to the pump housing by an inlet filter seal 154 to prevent unfiltered water or debris from entering the system. Pressurized treatment water 402 exits the water pump 124 via the water conduit 128, which leads to the water conduit outlet 142. This water conduit outlet 142 can include an inlet opening gasket 162, and mates with the inlet opening 140 on the inner lid 114, enabling seamless fluid delivery into the fluid channel 126.

Inside the fluid channel, water is directed through one or more impingement ports 130, which are oriented to spray treatment water directly onto the treatment ice 406 within the ice container 104. The impingement enhances melt performance and accelerates the cooling of the circulating treatment water 402. Chilled water then rises through the system, as guided by the egress ridges 132, and exits via the fluid channel slots 136 as previously described.

Also visible in the exploded assembly are several user interface and structural support components. The power button 106 and mode select button 108 are mounted on the outer face of the controls cover and allow the user to turn the system 'ON' and 'OFF' as well as toggle operational settings such as water pump 124 intensity or duration. A status indicator 144, positioned nearby, provides real-time visual feedback of the system's operational state using an LED or equivalent signaling technology.

Additional mechanical fasteners 150, such as screws, rivet, and other suitable fasteners can be used to secure the various parts of the chilling system 100, as required and/or desired in a particular embodiment.

In an exemplary embodiment, the agitator module 102 may be configured not only to house functional components such as the water pump 124, controller 500, rechargeable battery 514, and temperature sensor 522, but also to incorporate flow-directing features that eliminate the need for a separate lid assembly. Specifically, the agitator module 102 can include one or more impingement ports, formed as integrated openings, nozzles, or flow channels within the water conduit 128 or connecting enclosure 138, which are oriented to direct treatment water 402 toward the surface of the treatment ice 406 within the ice container 104. These impingement ports may be molded or machined into the agitator housing and may include angled or contoured features to create high-velocity, focused streams that enhance melt performance and thermal transfer.

In this configuration, the treatment water 402 drawn in through the inlet filter 152 is circulated by the pump 124 through the internal fluid pathways of the agitator module. Once pressurized, the water exits via the impingement ports, which are aligned with the upper or lateral regions of the treatment ice 406 to ensure continuous exposure and agitation. As the water flows across the ice surface, it is chilled and subsequently exits the ice container through one or more egress ports/paths, which may also be integrated directly into the agitator module housing or positioned near its lower edge in conjunction with the container wall. This flow circuit enables the treatment water to re-enter the treatment tub 404, completing a passive or pump-assisted recirculation loop.

This embodiment provides several functional advantages over prior configurations requiring a multi-component lid assembly. By consolidating the pumping, direction, and discharge functionality within the agitator module itself, the overall assembly is simplified, reducing part count, improving sealing integrity, and streamlining setup for the user. Additionally, this design facilitates improved cleaning, transport, and modularity, as the entire flow and control system is housed within a single detachable component. When the agitator module 102 is removed, the ice container 104 can be independently frozen, stacked, or stored, and reconfigured later without requiring alignment of a separate fluid path or lid structure.

In an exemplary embodiment, the ice container 104 is formed from a polymeric material selected not only for thermal insulation during use, but also for controlled stiffness and flexibility during and after freezing. This structural balance allows the treatment ice 406 to detach cleanly from the container's interior walls once submerged in treatment water 402, enabling the ice to float upward and increase its contact surface with the circulating water. The detachment behavior is dictated by a combination of the polymer's material properties (e.g., modulus of elasticity), wall thickness, and internal geometry-including any surface texturing or release-promoting structures such as the fin 160.

The geometry of the ice container 104 may also be configured to enhance freeze efficiency, especially when used in conjunction with a convection freezing system. In some embodiments, the container includes external airflow channels, contours, or positioning recesses 156 that facilitate the flow of air 212 around or beneath the unit. These airflow pathways reduce insulating boundary layers and allow fan-driven convection to improve overall heat extraction rates. A fan 210, powered either by battery or wired connection within the cooling and charge chamber 202, may direct high-velocity air into select regions of the chamber to maintain airflow across critical surfaces of the container.

To further accelerate freezing, the ice container may include one or more internal projections or receptacles designed to hold removable or embedded conductive materials. These materials may be fabricated from high-thermal-conductivity materials such as aluminum or copper, or conductive polymers, and are configured to increase the internal surface area in contact with water. The result is a more uniform and faster freezing process, enabling efficient preparation of treatment ice and reducing turnaround time between therapy sessions.

Figure 12A:
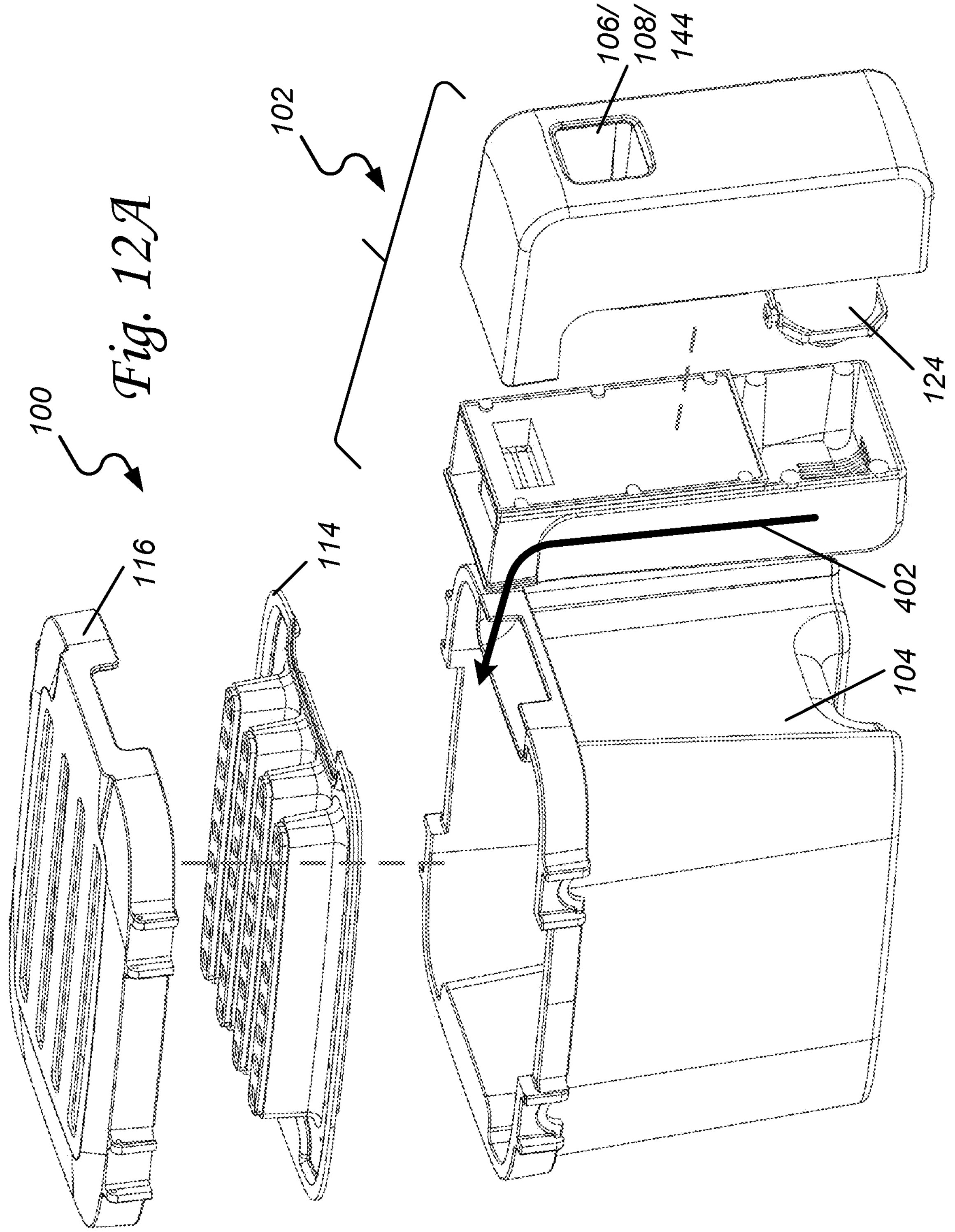
FIG. 12A illustrates one example of a chill system with an agitator assembly diagram.

Referring to FIG. 12A, there is illustrated one example of a chill system 100 is illustrated, including an agitator module 102 coupled to an ice container 104.

In this example, the chill system 100 is configured for use in cold water immersion therapy within a tub 404 containing treatment water 402. The ice container 104 defines an interior volume configured to hold treatment ice 406 and is sized to be positioned directly within the tub 404 such that treatment water 402 within the tub 404 may circulate around and through the system during operation. In embodiments with large tubs 404, more than one chilling system 100 can be placed in the treatment water 402 and operate to increase the speed of chilling the treatment water.

The agitator module 102 is mounted to the ice container 104 via a lid assembly 114/116 positioned at an upper opening of the ice container 104. The agitator module 102 houses a pump 124 configured to draw treatment water 402 from the tub during use. A connecting enclosure 138 fluidly couples the pump 124 to internal fluid channels 126 formed in the lid 114/116, thereby establishing a controlled fluid delivery path from the tub 404 to and through the ice container 104.

As shown, the connecting enclosure 138 is configured to route treatment water 402 upward from the pump 124 along a generally vertical flow path before redirecting the treatment water 402 into the lid 114/116. This arrangement enables treatment water 402 to be delivered to one or more impingement ports 130 associated with the ice container 104 with minimal loss of flow momentum. During operation, treatment water 402 discharged from the impingement ports 130 is directed toward treatment ice 406 contained within the ice container 104, after which the treatment water 402 returns to the tub 404, forming a recirculating treatment water loop that contacts a user 302 immersed in the treatment water 402.

Figure 12B:
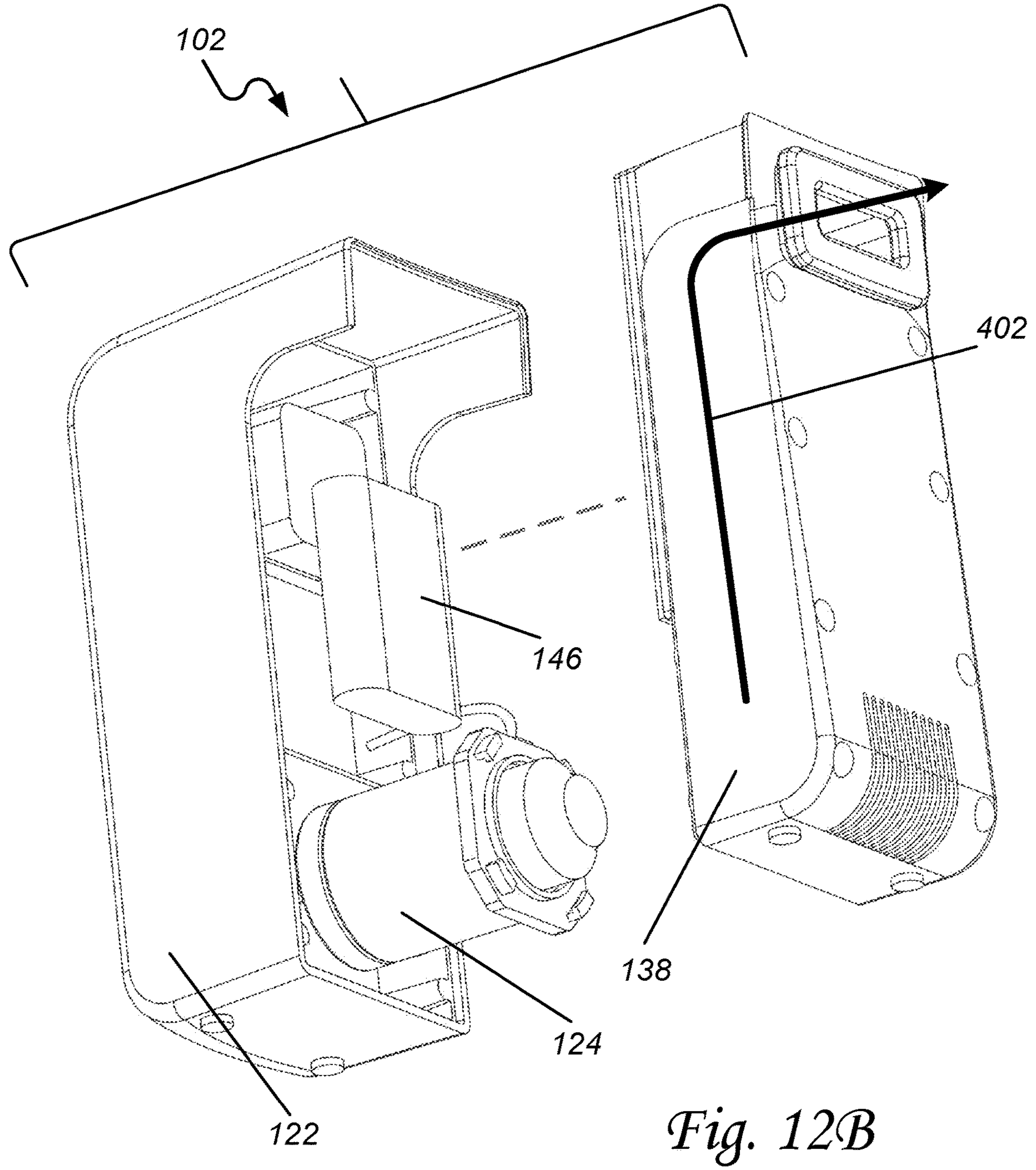
FIG. 12B illustrates one example of an agitator assembly diagram.

Referring to FIG. 12B, there is illustrated one example of the agitator module 102 in an assembly diagram.

In this view, the agitator module 102 is shown with its primary components separated to illustrate fluid and structural relationships. The pump 124 is positioned within a controls cover 122 housing of the agitator module 102 and is configured to receive treatment water from the surrounding tub 404 environment when the chill system 100 is submerged in the treatment water 402.

The connecting enclosure 138 extends from an outlet of the pump 124 and defines an internal flow passage configured to convey treatment water 402 toward the lid 114/116. In this exemplary embodiment, the internal flow passage 402 extends along a generally vertical axis from the pump 124 and transitions through one or more angular bends that redirect the treatment water 402 into the lid region 114/116. The internal flow passage 402 is substantially free of internal contours, obstructions, or tortuous routing that would otherwise abate the momentum of the treatment water 402 prior to delivery.

At least FIG. 11A shows the portions of the lid 114/116 that define one or more internal fluid channels 126. These internal fluid channels 126 are arranged to receive treatment water 402 from the connecting enclosure 138 and distribute the treatment water 402 toward multiple impingement ports 130. This configuration supports efficient transfer of treatment water 402 from the pump 124 to the ice container 404 and impingement onto the treatment ice 406 while preserving water flow energy.

Figure 12C:
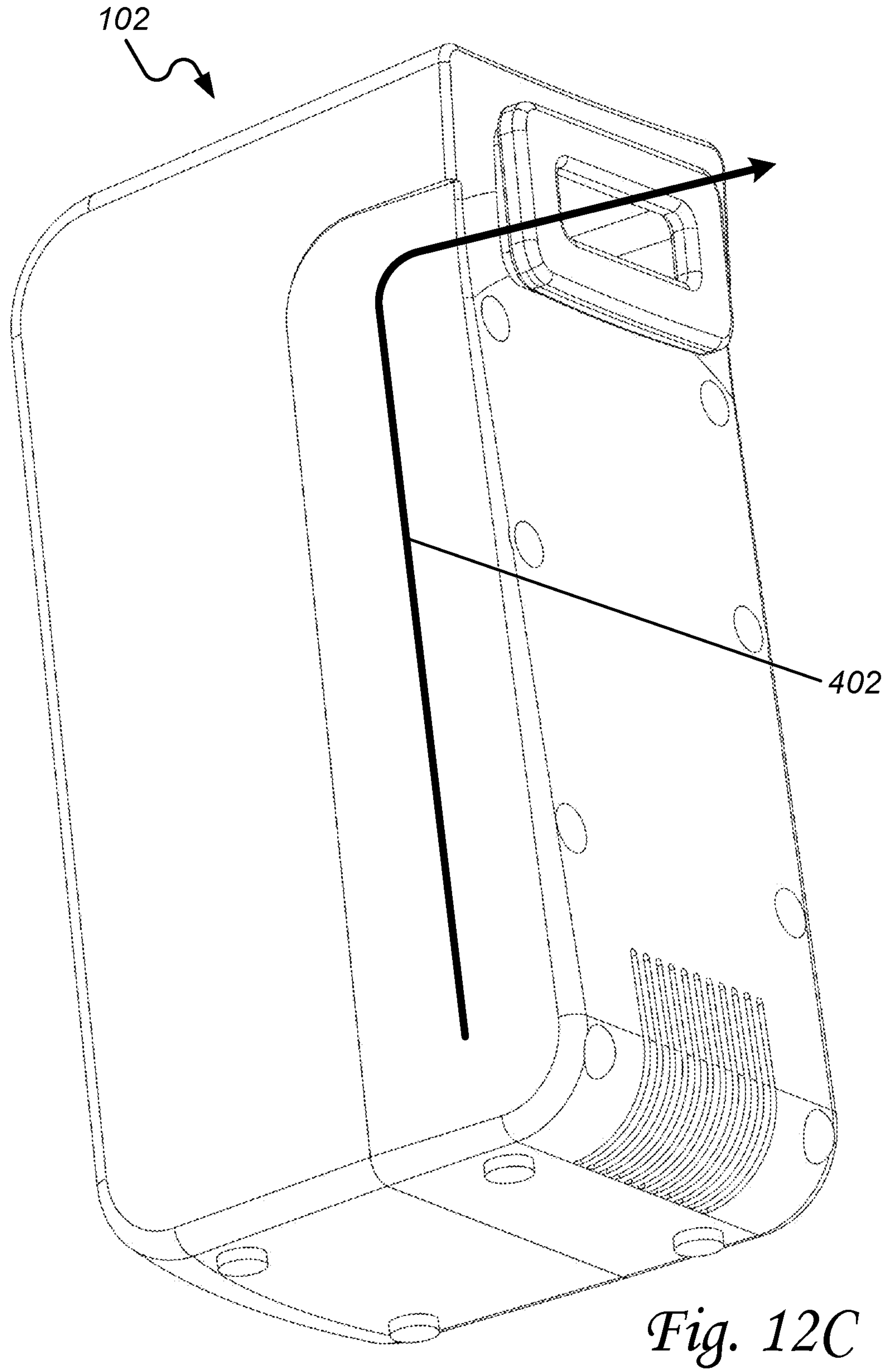
FIG. 12C illustrates one example of an agitator.

Referring to FIG. 12C, there is illustrated one example of the agitator module 102 in an assembled configuration.

Figure 12D:
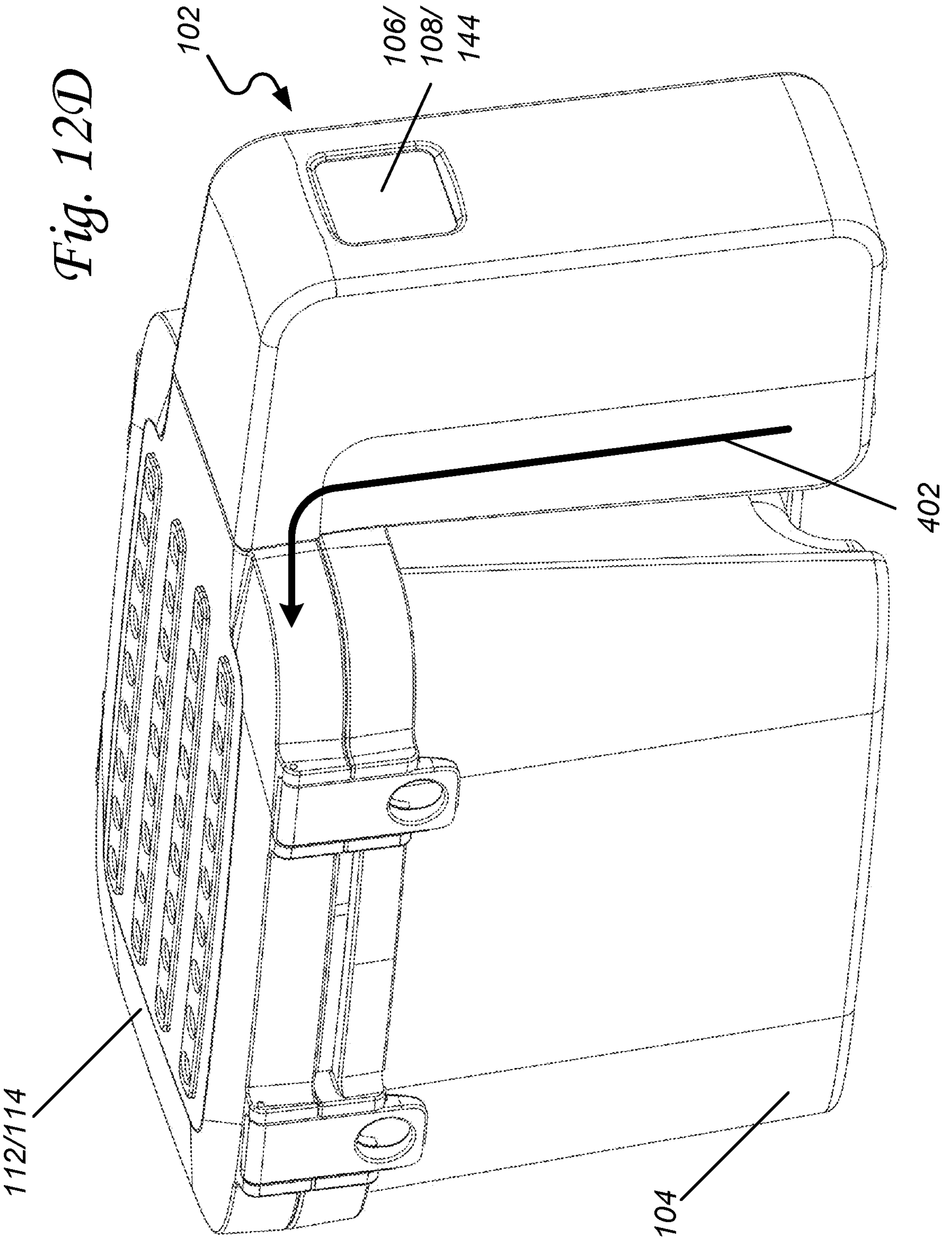
FIG. 12D illustrates one example of a chill system with an agitator.

In this view, the pump 124 and connecting enclosure 138 are shown integrated within the agitator module 102 for aligned with the lid 114/116, better illustrated in at least FIG. 12D. The connecting enclosure 138 interfaces with the lid 114/116 such that treatment water 402 exiting the one or more angular bends enters the one or more internal fluid channels 126 formed in the lid 114/116.

The internal fluid channels 126 extend within the lid 114/116 to supply treatment water 402 to a plurality of impingement ports 130. The impingement ports 130 are oriented to direct treatment water 402 downward toward the treatment ice 406 contained within the ice container 402. By supplying treatment water 402 to multiple impingement ports 130 via the internal fluid channels 126, the agitator module 102 enables treatment water 402 to be delivered across multiple spaced locations of the treatment ice 406 rather than at a single point. This increases the melt rate of the treatment ice 406 and speeds chilling of the treatment water 402.

This distributed impingement promotes more uniform heat transfer between the treatment water 402 and the treatment ice 406 during use. As treatment water 402 contacts the treatment ice 406, the treatment water 402 is chilled and subsequently exits the ice container 104 to return to the surrounding tub 402.

Referring to FIG. 12D, there is illustrated one example of the chill system 100 with the agitator module 102 installed on the ice container 104.

In this configuration, the ice container 104 is shown positioned for operation within a tub 404 containing treatment water 402. The lid 114/116 couples the agitator module 102 to the ice container 104 and defines a fluid interface between the connecting enclosure 138 and the internal fluid channels 126.

Within the interior volume of the ice container 104, one or more internal structures are positioned to interact with treatment ice 406. Better illustrated in at least FIG. 21, the internal structures include at least one fin 160 extending into the interior volume. The fin 160 can be configured such that treatment ice 406 formed within the ice container 104 may initially adhere to the fin 160 during freezing.

During use, treatment water 402 drawn from the tub 404 by the pump 124 is delivered through the connecting enclosure 138, routed through the internal fluid channels 126 in the lid 114/116, and discharged through the impingement ports 130 toward the treatment ice 406. As the treatment water 402 contacts the treatment ice 406, melting begins, causing the treatment ice 406 to separate from the fin 160. Once released, buoyancy causes the treatment ice 406 to move upward and float within the ice container, increasing the exposed surface area of the treatment ice 406 in contact with circulating treatment water 402. The increased exposed surface area increases the treatment ice 406 melt and speeds chilling of the treatment water 402.

The chilled treatment water 402 then exits the ice container 104 and returns to the tub 404, where it mixes with surrounding treatment water 402 and contacts a user 302 immersed therein. This recirculating treatment water loop enables the ice container 104 to function as an in-situ heat exchange component within the tub 404, providing rapid chilling of the treatment water 402 during an immersion therapy session.

Figure 12E:
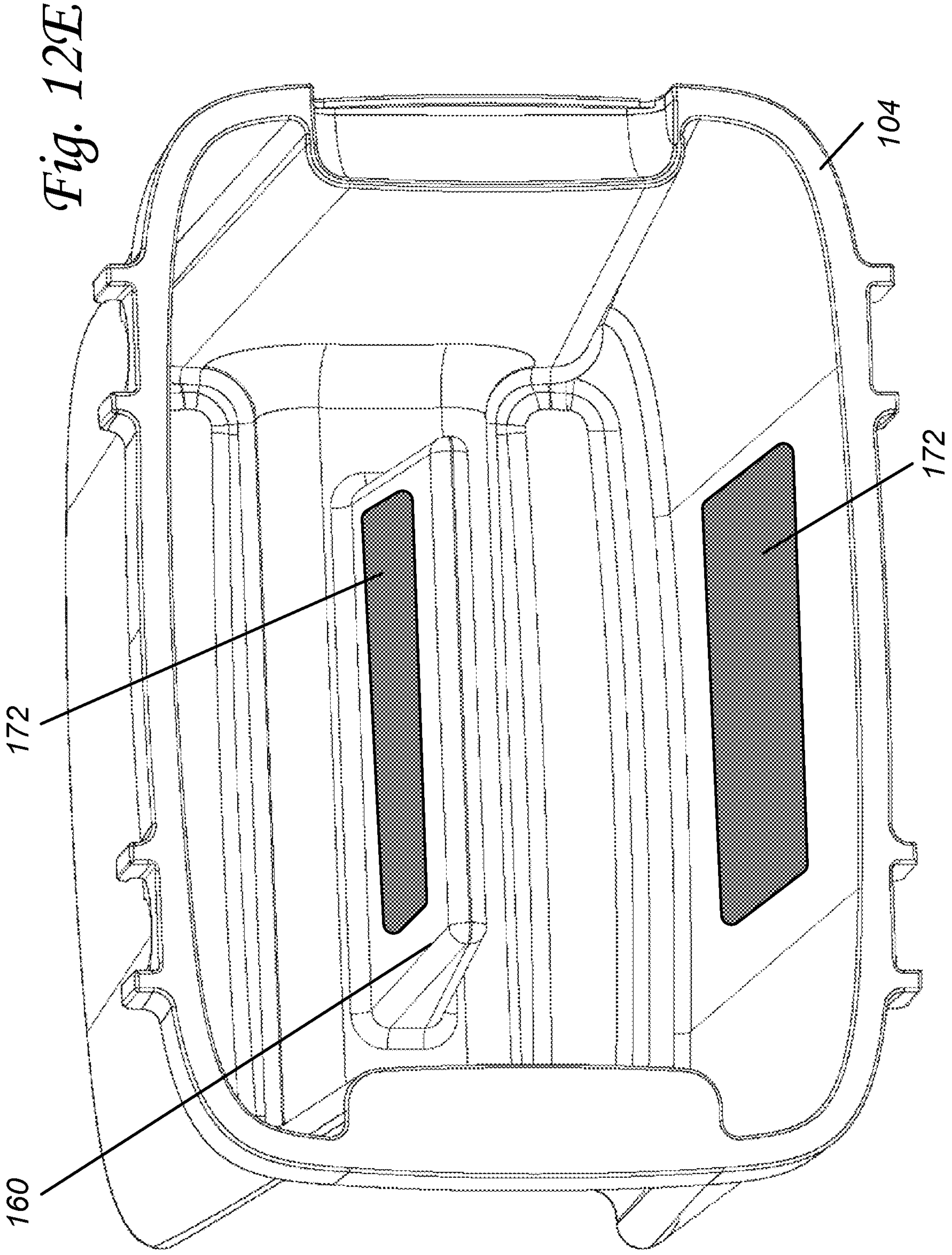
FIG. 12E illustrates one example of an ice container with conductive inserts.

Referring to FIG. 12E, there is illustrated one example of an ice container 104 is illustrated, including one or more conductive inserts 172 positioned within an interior volume of the ice container.

In this exemplary embodiment, the ice container 104 is configured for use in cold water immersion therapy and is sized to be positioned within a tub 404 containing treatment water 402. The conductive inserts 172 extend into the interior volume of the ice container 104 and are arranged to interact directly with water prior to use during freezing to form the treatment ice.

The conductive inserts 172 may comprise elongated elements such as rods, fins, ribs, plates, or other structures formed from materials having higher thermal conductivity than the surrounding body of the ice container 104. By way of non-limiting example, the conductive inserts 172 may be formed from metals, metal alloys, ceramic-filled polymers, or other thermally optimized polymeric materials. In some embodiments, multiple conductive inserts 172 are provided and may be spaced apart from one another to distribute thermal conduction across different regions of the interior volume.

During a freezing phase prior to use, water introduced into the ice container 104 freezes around the conductive inserts 172. The conductive inserts 172 act as thermal conduction pathways that accelerate heat extraction from the water, thereby reducing the time required to form treatment ice 406 within the ice container 104. In this manner, the conductive inserts 172 improve preparation efficiency for a therapy session.

In the illustrated embodiment, the conductive inserts 172 extend inward from one or more interior walls, the fin 160, or other suitable areas of the ice container 104. In some variations, the conductive inserts 172 may be permanently bonded to the ice container 104, such as by over-molding, adhesive bonding, welding, or integral formation during manufacture. In other variations, the ice container 104 may define one or more mounts, recesses, slots, or receivers configured to removably receive the conductive inserts 172, thereby allowing a user to install, remove, or interchange different insert configurations to tailor freezing and melting characteristics.

During use, when the ice container 104 is submerged in treatment water 402 within the tub 404, treatment water 402 drawn from the tub 404 is delivered through internal fluid channels 126 in the lid 114/116 and discharged through one or more impingement ports 130 toward the treatment ice 406 formed around the conductive inserts 172. As the discharged treatment water 402 contacts the treatment ice 406, the treatment water 402 is chilled and returns to the tub 404 to form a recirculating treatment water loop.

As the melting of the treatment ice 406 initiates, the conductive inserts 172 cooperate with circulating treatment water 402 to reduce adhesion between the treatment ice 406 and the ice container 104. This interaction promotes detachment of the treatment ice 406 from the conductive inserts 172 and allows the treatment ice 406 to move upward and float within the ice container 104 due to buoyancy. Upward movement of the treatment ice 406 increases the exposed surface area of the treatment ice 406 in contact with circulating treatment water 402, thereby enhancing heat transfer and accelerating chilling of the treatment water 402 during an immersion therapy session.

In an exemplary embodiment, one or more of the conductive inserts 172 extend through or penetrate a wall of the ice container 104 such that a first portion of each conductive insert 172 is positioned within the interior volume of the ice container 104 and a second portion of each conductive insert 172 is externally exposed outside the ice container. In this configuration, the externally exposed portion of the conductive insert 172 is configured to thermally couple with an external cooling environment in which the ice container 104 is placed during a freezing phase, such as a freezer or other cold storage environment, such as charge chamber 202. Thermal energy is conducted from treatment water within the ice container 104, through the conductive insert 172, and dissipated into the external environment, thereby accelerating formation of treatment ice within the ice container relative to containers lacking such thermally coupled structures.

In further exemplary embodiments, the conductive inserts 172 that penetrate the wall of the ice container 104 may be sealed to the ice container to prevent leakage of treatment water while maintaining thermal conductivity. The externally exposed portions of the conductive inserts 172 may be configured as fins, rods, plates, or other surface-enhancing geometries to increase heat transfer to the surrounding freezing environment. During use, when the ice container 104 is submerged in treatment water within a tub, the same conductive inserts 172 continue to function as internal heat transfer elements that cooperate with circulating treatment water to promote detachment and upward movement of the treatment ice. In this manner, the conductive inserts 172 provide dual functionality by accelerating ice formation prior to use and enhancing ice release and chilling efficiency during an immersion therapy session.

Referring to FIGS. 12F-12K, there is illustrated one example of a stacking lid 174 configured for use with the ice container 104 during formation of treatment ice external of a tub.

In this exemplary embodiment, the stacking lid 174 is configured to be removably secured to an upper opening of the ice container 104 while water contained therein is being frozen into treatment ice, such as when the ice container 104 is placed within a freezer or other cold storage environment.

As shown in FIG. 12F, reference views “A” and “B” illustrate top perspective views of the stacking lid 174. In these views, the stacking lid 174 defines an upper surface configured to receive and support another ice container 104 placed thereon. The upper surface may include a recessed region, raised rim, contour, or other locating feature configured to engage a lower portion of the ice container 104 positioned above it. This engagement inhibits lateral movement between stacked ice containers and reduces the likelihood of slippage during stacking, transport, or freezing.

Figure 12G:
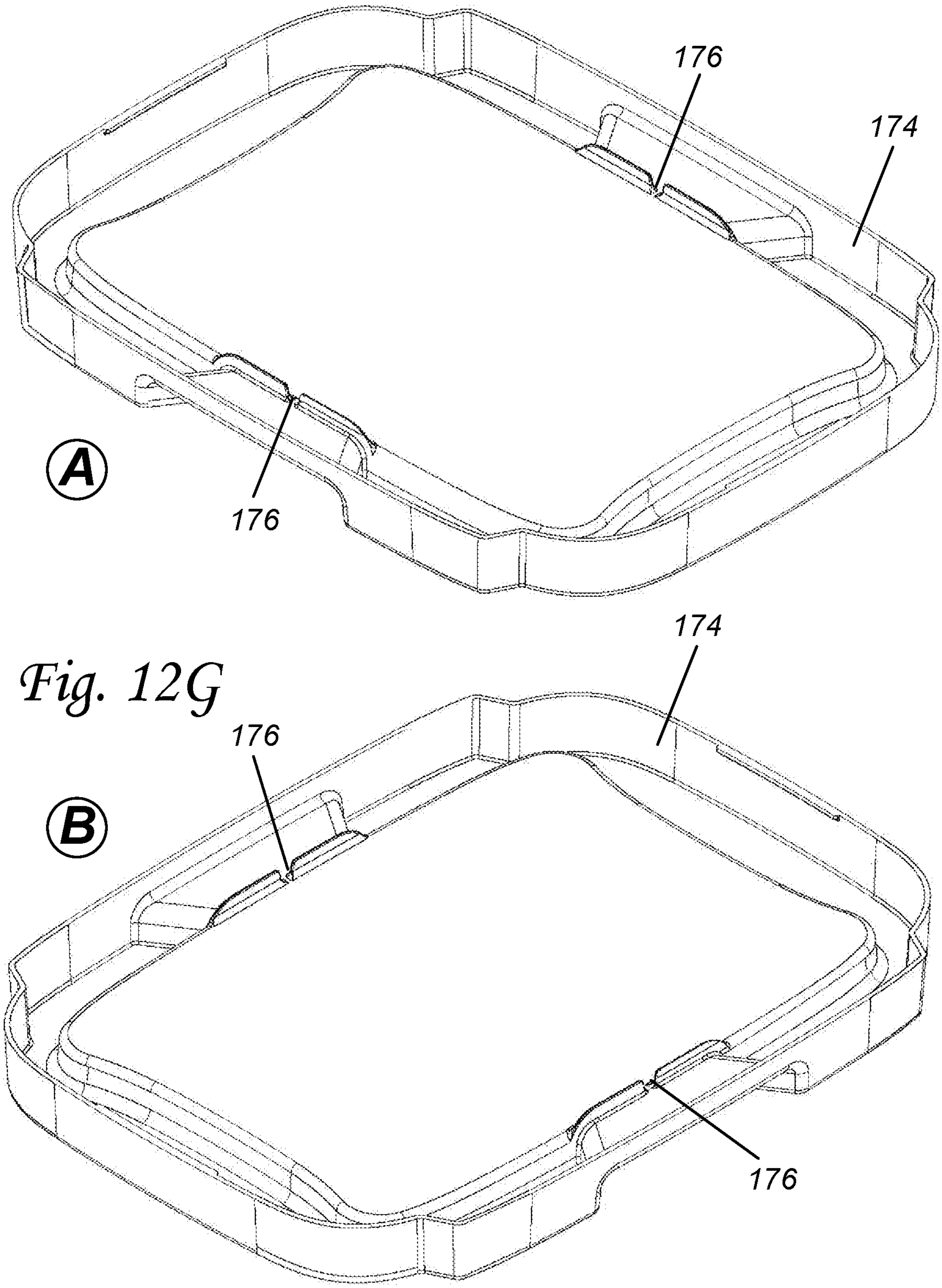

FIG. 12G, reference views “A” and “B,” illustrate bottom perspective views of the stacking lid 174. In these views, the stacking lid 174 includes a lower interface region configured to mate with the top of the ice container 104. An air vent 176 can be formed into the innerseal perimeter to allow air to equalize within the ice container 104 during the water freezing process, as well as during the ice container 104 stacking process. The lower interface region may include one or more sealing surfaces, lips, flanges, or engagement features configured to seat against the ice container 104 to secure and lock the stacking lid 174 in place. When installed, the stacking lid 174 covers the open top of the ice container 104, thereby reducing or preventing spillage of water during handling, movement, or sloshing prior to freezing.

Figure 12H:
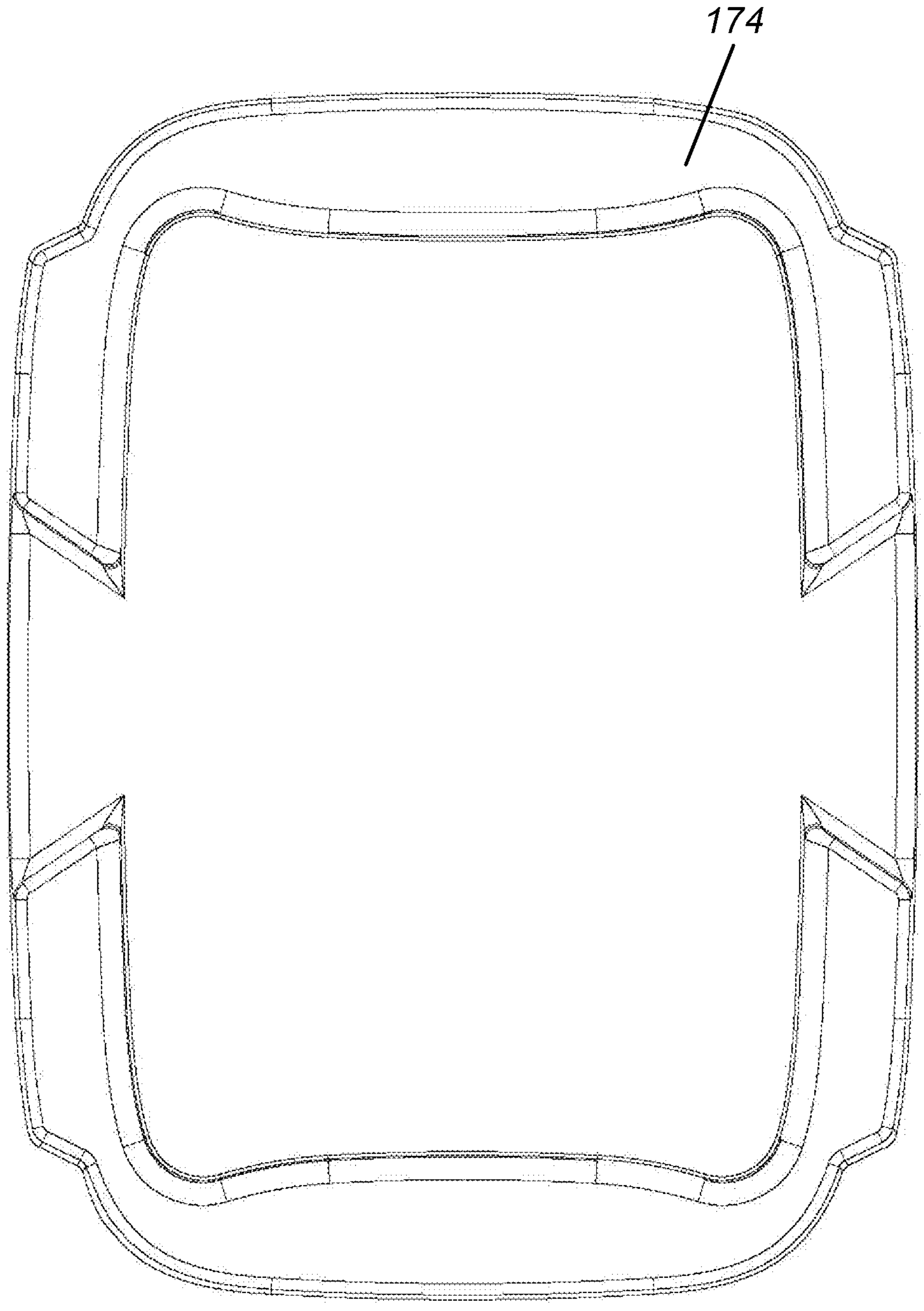

FIG. 12H illustrates a top view of the stacking lid 174. In this view, the geometry of the upper surface of the stacking lid 174 is shown as configured to receive a corresponding footprint of an ice container 104 placed above it. The upper surface may be circular, polygonal, or otherwise shaped to complement the geometry of the ice container 104, and may include centering features that guide placement of the ice container 104 during stacking.

Figure 12I:
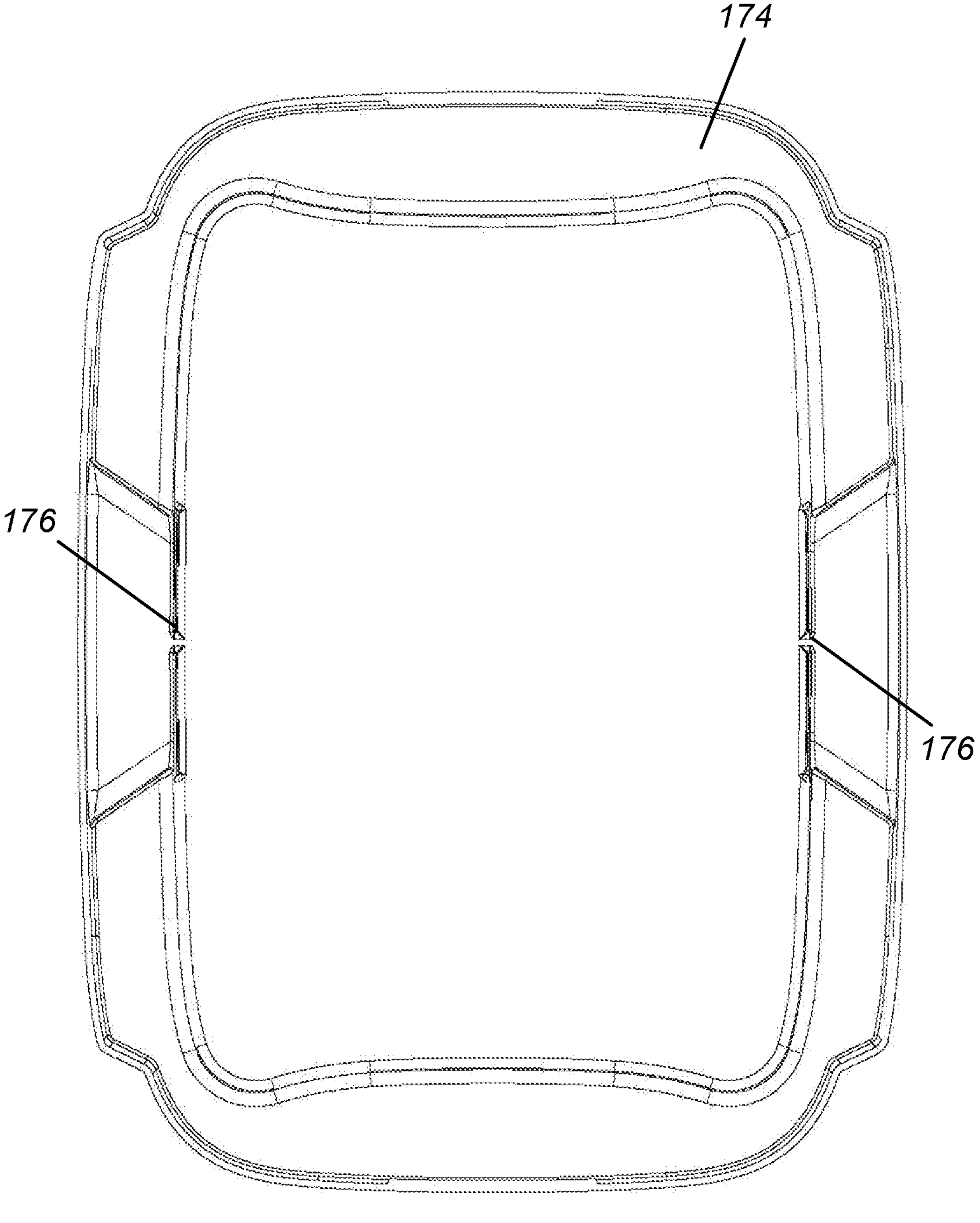

FIG. 12I illustrates a bottom view of the stacking lid 174. In this view, the lower interface region of the stacking lid 174 is shown as configured to align with and secure to the upper rim of the ice container 104. The lower surface geometry may be selected to distribute loads from stacked ice containers while maintaining a stable seal to the ice container 104 below.

Figure 12J:
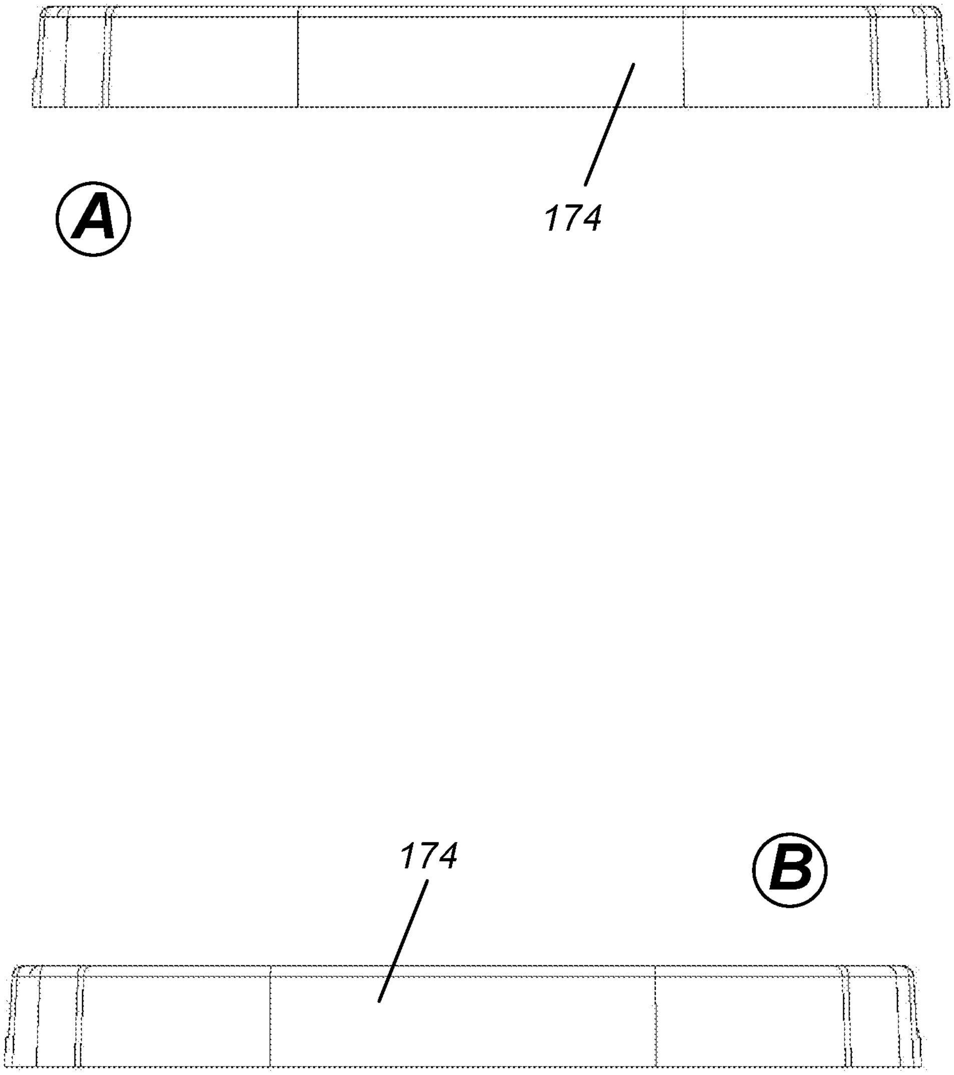
Figure 12K:
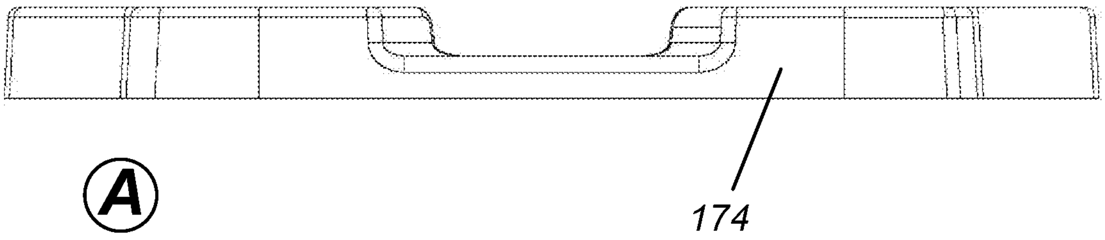
Figure 12K:
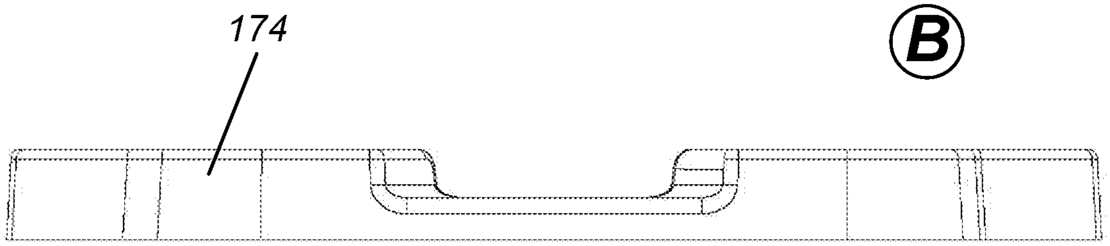

FIGS. 12J, reference views "A" and "B," illustrate front and back views of the stacking lid 174, respectively, while FIGS. 12K, reference views "A" and "B," illustrate left and right side views of the stacking lid 174. These views collectively illustrate the vertical profile and thickness of the stacking lid 174, as well as any peripheral contours or engagement features that cooperate with the ice container 104. In some embodiments, the stacking lid 174 may include a substantially uniform thickness, while in other embodiments, the thickness may vary to provide additional rigidity or nesting functionality.

During use, the stacking lid 174 enables multiple ice containers 104 filled with treatment water to be stacked vertically during a freezing phase, thereby conserving space within a freezer and improving preparation efficiency. By securing to the ice container 104 and preventing water spillage, the stacking lid 174 facilitates safe handling and transport prior to freezing. Once treatment ice has been formed, the stacking lid 174 may be removed to allow the ice container 104 to be configured and used within a tub for cold water immersion therapy, or replaced with another lid or agitator assembly as described elsewhere herein.

Figure 13:
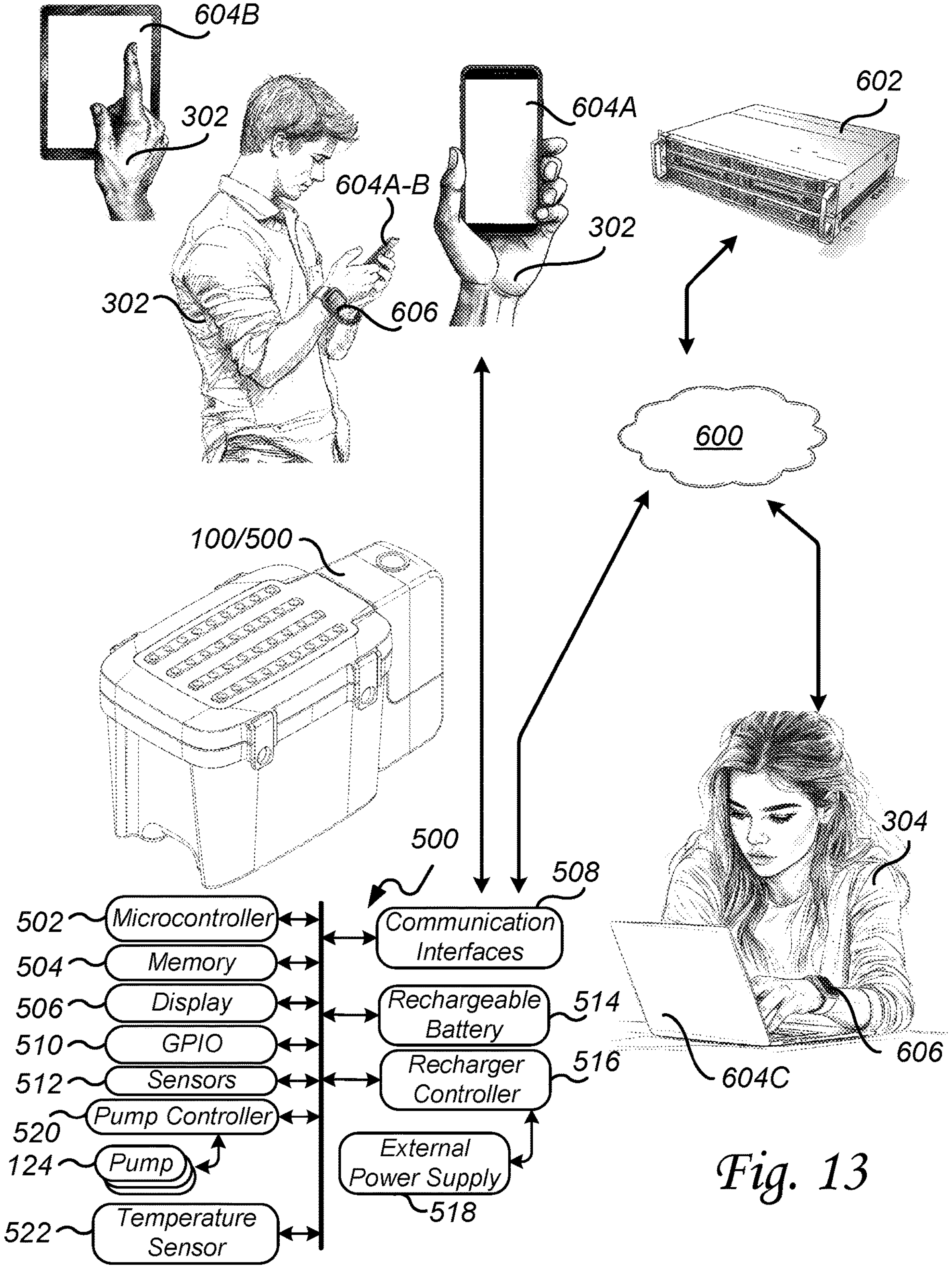
FIG. 13 illustrates one example of the chilling system control system and a network diagram.

Referring to FIG. 13, there is illustrated one example of the chilling system 100 and its associated control system 500, and network connectivity 600. This figure details how the agitator module 102 integrates control, power management, sensing, and wireless communication capabilities to support intelligent operation and connected cold water therapy experiences.

At the heart of the system is a controller 500, housed within the agitator module 102 and responsible for managing all functional operations of the chilling system 100. The controller 500 includes a microcontroller 502, which serves as the central logic unit. The microcontroller 502 is operationally coupled to a variety of onboard and peripheral components, allowing the system to autonomously regulate its own functionality and respond to user input or remote instructions.

The memory 504 stores executable firmware, session presets, sensor calibration profiles, and user-defined treatment parameters. This memory may comprise volatile and non-volatile types such as flash, EEPROM, or RAM, enabling both persistent data logging and runtime computation.

A display 506, which may include an LED array, LCD, or similar visual indicator, is positioned on the exterior of the controls cover 122 of the agitator module 102. It is configured to display system status, session countdowns, pump intensity, or other session-specific alerts. This display is supported by an adjacent status indicator 144, which may provide visual confirmation of device readiness, operational activity, or fault states.

The communication interface 508 enables wireless or wired connectivity between the controller 500 and external systems. Supported interfaces may include Bluetooth, Wi-Fi, NFC, USB, or other suitable wireless interface and/or protocol, depending on implementation. Through this interface, the chilling system 100 operates as a fully web-enabled Internet of Things (IoT) device.

The controller 500 further includes a bank of general purpose input and outputs (GPIO) 510, which support signaling and control of peripheral elements including sensors, switches, and diagnostic ports.

A power switch 106, a status indicator 144, and a mode select button 108 can be integrated as part of the GPIO 510. The power switch 106 can be configured to start and stop the agitator module 102. The status indicator can be configured to provide a visual indication through light light-emitting diode (LED) or other suitable indicators of the operational status of the agitator module 102. The mode select button 108 can be configured for user interaction. This input allows the operator to cycle between predefined therapy modes, such as low, medium, or high agitation, and initiate or terminate a treatment session. Control logic within the microcontroller 502 interprets this input and adjusts pump speed, duration, or sensor thresholds accordingly.

A variety of sensors 512 may also be supported, including water level sensors, flow rate detectors, or pump diagnostics, enhancing feedback and safety.

The rechargeable battery 514 supplies power to the controller 500 and the pump 124. Battery performance is governed by a recharge controller 516, which manages charge/discharge cycles, session runtime, and power allocation between system components. Power can be replenished from an external power supply 518, which may include a wall transformer, solar charger, USB source, or inductive charging pad-especially useful when the chilling system is docked in a cooling and charge chamber 202.

The pump controller 520 is a dedicated driver circuit under the direction of the microcontroller 502. It regulates the speed, duty cycle, and activation of the water pump 124, which draws water through the inlet filter 152 and directs it through the impingement ports 130 and over the treatment ice 406.

Among the supported sensors is a temperature sensor 522, which monitors the temperature of the surrounding treatment water 402 and enables the system to modulate water circulation rates to maintain a predefined thermal profile. The temperature sensor 522 may comprise a thermistor, RTD, or infrared element positioned in fluid contact with the water circuit.

In terms of external connectivity, the chilling system 100 communicates by way of the controller system 500 communication interface 508 over a global network 600, such as the Internet, enabling a wide range of cloud-connected functionality. The communication interface 508 allows the controller 500 to exchange data with:

Remote data processing resources 602 such as a cloud server, which may store session logs, manage firmware updates, or run predictive analytics;

Computing devices 604, including 604A smartphones, 604B tablets, and 604C laptops or desktops, which allow users to configure sessions, monitor live status, or review historical performance via a dedicated app or web interface;

Wearable devices 606, such as smartwatches or biometric trackers, which may supply real-time biometric feedback (e.g., heart rate, skin temperature) to the chilling system 100 or receive status alerts and readiness prompts from it; and Data communicates in other ways with other data processing devices, as may be required and/or desired in a particular embodiment.

The controller 500 may receive biometric inputs, session trigger signals, or other data from the wearable device 606, coordinate session timing with a smartphone app 604A, log post-session data to the cloud via the remote server 602, and be configured and utilized in other ways. In some embodiments, the wearable device 606 or app 604 can recommend session parameters based on user recovery state or previous session data, enabling a fully adaptive cold exposure regimen.

This multilayer architecture-comprising onboard control, user interface, and external connectivity-positions the chilling system 100 as a smart, connected, and autonomous platform for cold therapy. It moves beyond passive cooling to deliver interactive, data-driven therapy experiences, integrating seamlessly with the user's health ecosystem while offering robust local operation even in offline environments.

FIG. 11B collectively demonstrates how the chilling system 100 is modularly designed for efficient assembly, field servicing, and user-guided deployment. Unlike prior systems with fixed structures or disposable parts, the present design provides robust interlocking features, interchangeable modules, and a fully integrated water circulation path-all of which contribute to reusability, safety, and enhanced thermal performance.

Figure 14:
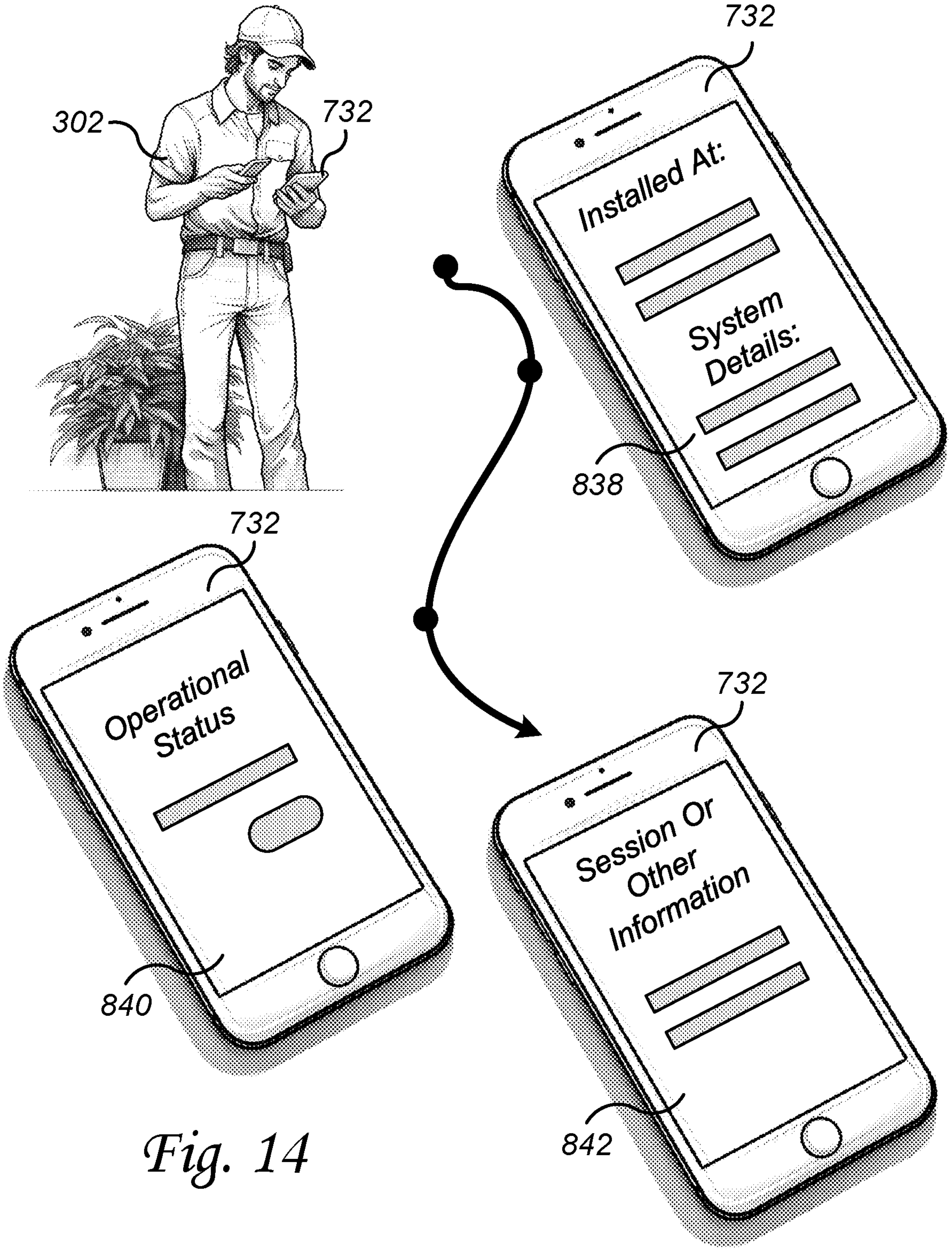
FIG. 14 illustrates one example of a user's use of a software application.

Referring to FIG. 14, there is illustrated one example of a user 302 interacting with a software application designed to monitor, configure, and manage the chilling system 100, including its integrated control system 500. In this exemplary embodiment, the user 302 operates a computing device 604, which may include a smartphone 604A, tablet 604B, laptop or desktop 604C, or a wearable device 606 such as a smartwatch, to access a dedicated application interface.

The software application enables full lifecycle interaction with the chilling system 100—from initial installation and diagnostics, to real-time session monitoring, remote control, and post-session analytics. The computing device 604 communicates with a remote data processing resource 602 (e.g., a cloud server) over a global network 600 (e.g., the Internet). This networked architecture allows the application to retrieve live system performance metrics, manage session scheduling, synchronize maintenance records, and log usage history across multiple sessions and devices.

A first display screenshot 838 illustrates a system overview dashboard, showing technical details associated with a specific chilling system 100. This includes identifying attributes such as device model and serial number, session configuration (e.g., single or dual pump, active agitation rate, ice block size), installation date, last serviced timestamp, current firmware version of the controller 500, and other data. This screen enables the user to confirm system registration and validate that the chilling system is online and properly provisioned.

A second display screenshot 840 shows an operational status interface. This screen provides real-time readouts of the system's active state, such as selected treatment mode (e.g., recovery, performance boost, cooldown), pump activity status, water temperature as measured by temperature sensor 522, and battery level from the rechargeable battery 514. The user 302 can verify that the system is operating within expected parameters, activate or pause sessions, and optionally initiate system diagnostics such as impeller checks or temperature sensor calibration.

A third screenshot 842 presents session history and maintenance logs. This screen may show upcoming scheduled sessions, recorded therapy durations, average water temperatures, or user exposure times. Maintenance data may include pump runtime hours, battery cycle count, and alerts for filter replacement or firmware updates. In some embodiments, the service app also provides prompts for cleaning, ice container refreezing readiness, or battery recharge optimization based on recent usage.

The user interface is designed to work seamlessly with the communication interface 508 of the controller 500, allowing bidirectional data exchange between the chilling system 100/500 and the application. Integration with a wearable device 606 further enables personalized session recommendations, heart rate or biometric monitoring, and automated session initiation based on detected physical activity or recovery state.

By providing a unified digital interface for session planning, system diagnostics, and device maintenance, the software application illustrated in FIG. 14 transforms the chilling system 100 into a smart, connected therapy device. It supports both casual users and professional operators by simplifying the operational workflow, improving accountability, and enabling data-driven personalization of cold water exposure therapy.

Figure 17:
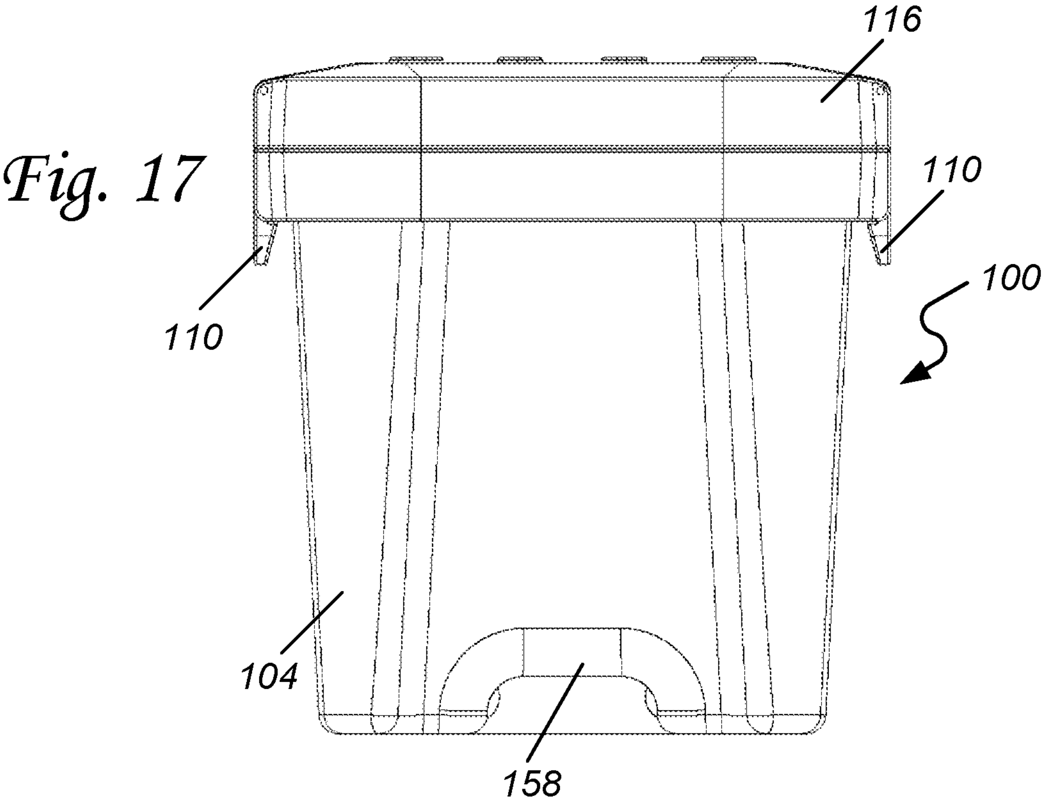
FIG. 17 illustrates one example of a front view of the cooling system.
Figure 18:
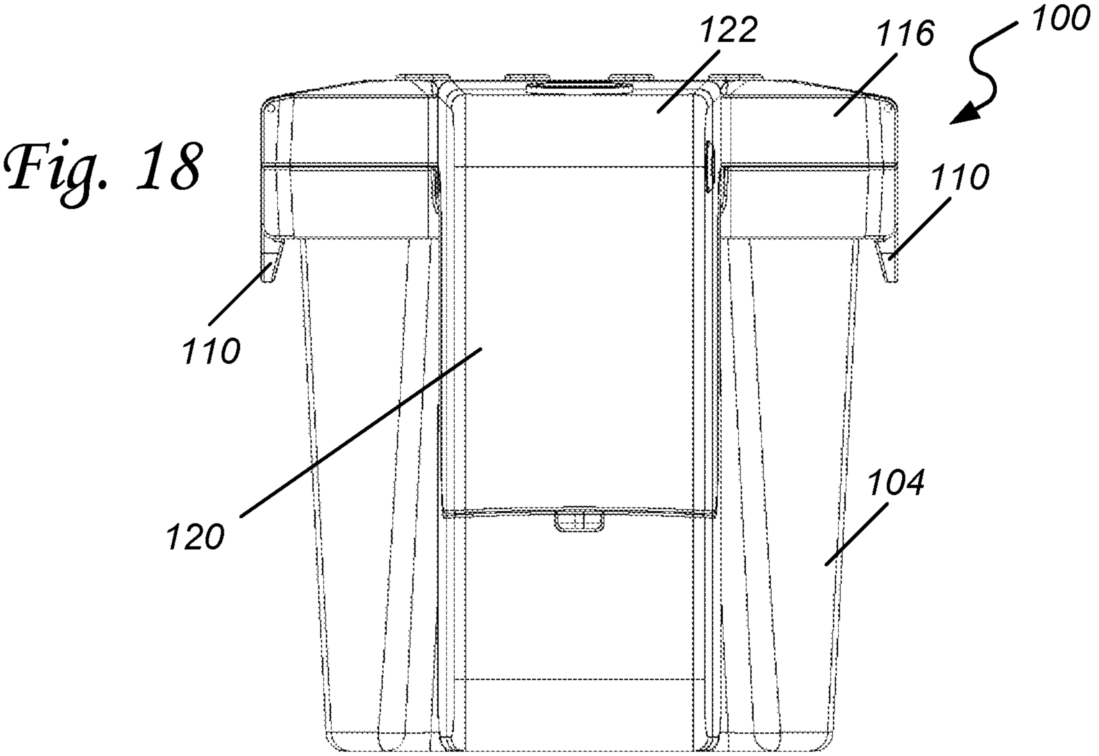
FIG. 18 illustrates one example of a back view of the cooling system.
Figure 19:
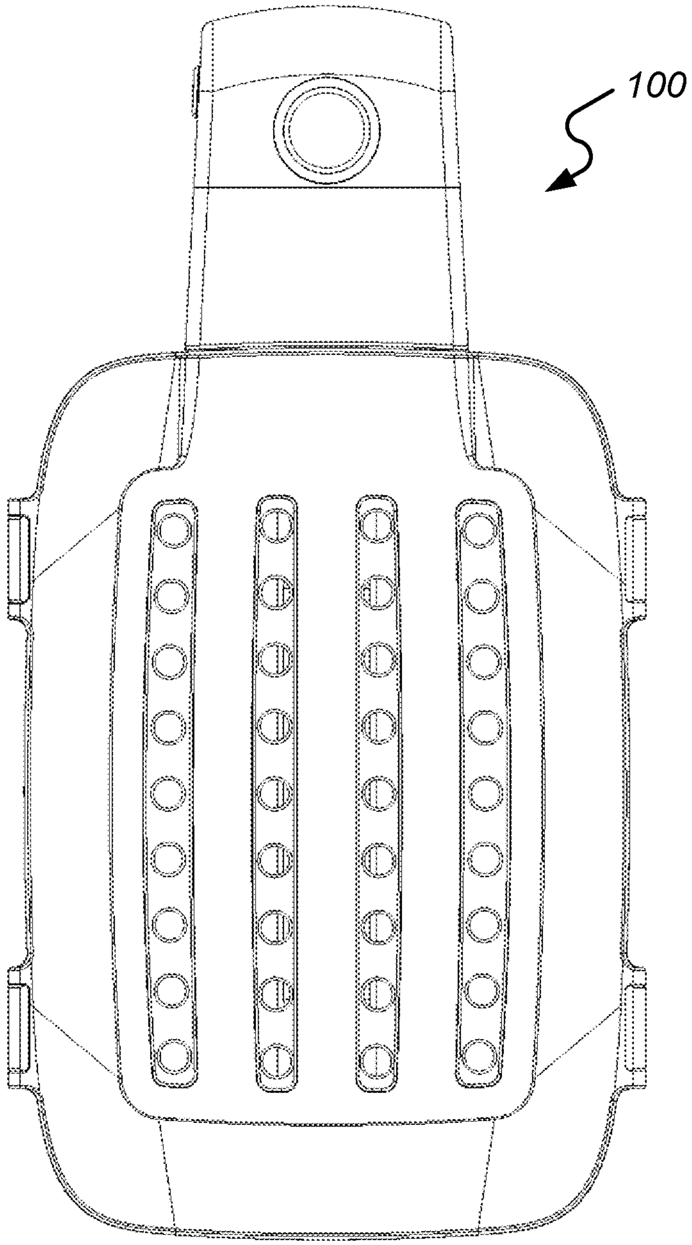
FIG. 19 illustrates one example of a top view of the cooling system.
Figure 20:
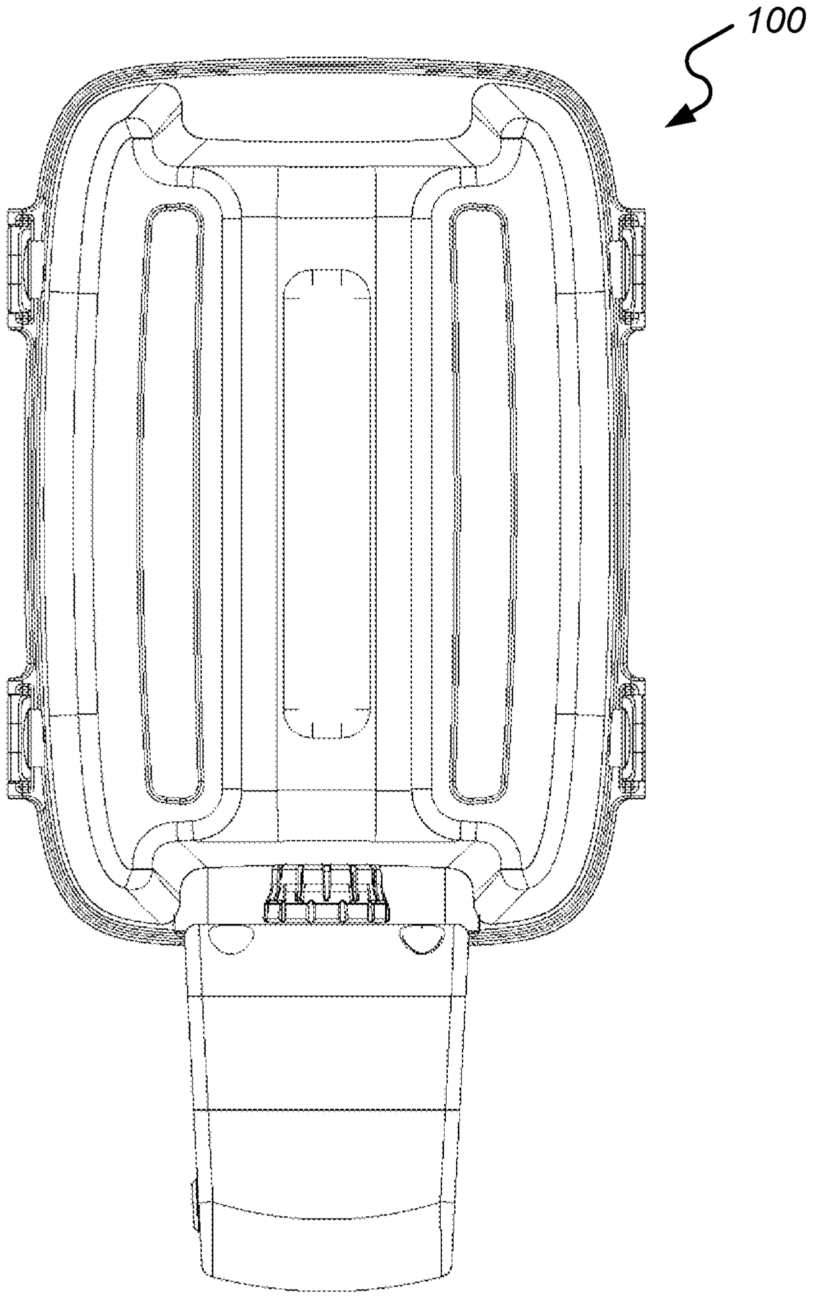
FIG. 20 illustrates one example of a left view of the cooling system.

Referring to FIGS. 15 through 20, there are illustrated orthogonal views of an exemplary embodiment of the chilling system 100, including FIG. 15, the left side, FIG. 16 right side, FIG. 17 front, FIG. 18 back, FIG. 19 top, and FIG. 20 bottom views, respectively. These views together reveal the complete exterior profile of the chilling system 100, including the integrated ice container 104, the agitator module 102, and the lid assembly formed by the inner lid 114 and outer lid 116. The system's geometric consistency across all faces reflects its modular and portable design, intended for repeatable placement into a treatment tank or a cooling and charge chamber without the need for orientation-specific components. These figures confirm the relative placement and alignment of key external features such as the scooped handle 166, flat handle 168, pump cover 120, controls cover 122, water conduit 128, and user interface elements like the status indicator 144 and mode select button 108.

From these views, the clean enclosure profile and sealed interface geometry are also evident, demonstrating how the chilling system 100 houses its internal fluid channel 126, impingement port architecture, water routing pathways, power system, and sensor electronics within a streamlined housing. The figures further reinforce that the system is symmetrical across key axes and structurally self-contained, with no external hoses, fasteners, or cabling required for operation. Aspects such as the integrated latch structure, inlet placement, and filter access are shown to be flush-mounted or integrated into the form factor, contributing to the overall waterproofing and ease of use. While the mechanical function and assembly logic have been described in prior figures, these orthogonal views provide dimensional and geometric context that supports manufacturing, user orientation, and visual confirmation of the complete device layout.

Referring to FIG. 21, there is illustrated one example of a perspective view of the ice container 104, shown in two orientations to highlight its internal geometry and melt-enhancing structural features. In reference view 'A', the interior cavity of the ice container 104 is visible from a frontal perspective, revealing the centrally positioned fin 160, which protrudes upward from the interior bottom surface. In reference view 'B', the ice container 104 is shown in a tilted orientation to further expose the lower cavity and clarify the relative placement of the fin 160 and surrounding support structures all of which contribute to the finned geometry that is configured to form a treatment ice 406 having a protruded or finned geometry to increase surface area and accelerate melting in the treatment water 402.

The fin 160 is configured as an integral upward projection within the ice container 104 and serves a critical role during the melting phase of a cold exposure session. When the container is filled and frozen, the treatment ice 406 forms around and partially envelops the fin. During operation, when circulating treatment water 402 is impinged onto the ice surface via water jets 130 (as shown in earlier figures), thermal transfer begins near the fin. This initiates a melt path along the interface between the ice and the container wall. As the ice begins to separate from the fin, additional surface area becomes exposed to the treatment water, increasing thermal contact and accelerating the melt rate. This mechanism promotes rapid deployment of chilling capacity into the surrounding bath, improving the system's time-to-temperature performance compared to prior passive approaches.

Also visible along the rim of the ice container 104 are the latch connectors 118, which are configured to interface with latch pins 112 of the latch assembly 110 to secure the inner and outer lid assembly. These connectors ensure that the lid remains tightly affixed to the container during freezing, handling, and circulation phases.

Positioned along the underside of the container is the water channel contour 158, which is visible in the angled perspective. This contour elevates the bottom surface of the container slightly above the base of the treatment tank, allowing treatment water to flow from both the front and rear toward the inlet filter 152 located beneath the agitator module. This encourages balanced flow dynamics and prevents dead zones where stagnant water might reduce system efficiency.

The scooped handle 166 is integrally formed on one end of the ice container 104, specifically at the interface where the agitator module 102 and water conduit 128 connect to the container and align with the inner lid 114 and inlet opening 140. The contoured geometry of the scooped handle 166 is configured to promote ergonomic lifting, positioning, and tilt control during insertion or removal of the chilling system 100 from a treatment tank 404 or cooling and charge chamber 202. The open contour also accommodates finger clearance and enhances grip, particularly when the system is wet or partially submerged.

Opposite the scooped handle, the flat handle 168 is formed integrally on the other end of the ice container 104. This structure presents a smooth, horizontal lifting surface and is specifically configured to engage with the inner lid 114 in a flush manner. In operation, the flat handle 168 helps prevent unintended treatment water leakage or egress at the lid-to-container contact zone proximate to this end. The contrasting handle geometries enable intuitive orientation of the chilling system and support balanced transport, modular sealing, and directional alignment for proper flow operation.

FIG. 21 thus illustrates several structural features that directly contribute to the thermal efficiency, reusability, and modular integration of the chilling system. By leveraging internal geometry, such as the fin and channeling structures, the system enables faster, more predictable chilling cycles and supports repeatable, high-performance cold therapy sessions across various use environments.

In an exemplary embodiment, the ice container 104 may be further enhanced with structural features that promote rapid and efficient freezing of the treatment ice 406. To reduce freeze times and improve thermal exchange during storage in the cooling and charge chamber 202, the ice container 104 can be formed with one or more airflow channels or positioning recesses 156. These features enable increased airflow to circulate around or beneath the container when the chamber fan 210 is activated, preventing the formation of insulating air pockets and supporting convective cooling. When multiple ice containers are stacked within the chamber, these airflow pathways maintain separation and ensure consistent freeze conditions across units. The geometry of the ice container 104 may also include raised ribs, inset panels, or cutaways that guide airflow along key surfaces in contact with cold plates or conductive shelving, further improving freeze uniformity.

In additional embodiments, the interior of the ice container 104 may include surface-enhancing structures, such as the fin 160, or other protrusions extending into the volume of the container. These internal features increase the surface area of water in contact with thermally conductive material, thereby accelerating heat extraction during freezing. In some variations, the ice container 104 may be configured to accept removable or embedded conductive inserts, such as metal rods, fins, or thermally optimized polymers, which nest within or project from the container walls. These inserts can be permanently bonded or slid into designated mounts within the container. Furthermore, the internal structures may be geometrically configured to allow the treatment ice 406 to release from the container and float upward when submerged in treatment water 402. This behavior exposes a greater portion of the treatment ice to circulating water early in the session, thereby increasing melt rate and chilling efficiency. Collectively, these enhancements provide faster freeze times, improved modularity, and optimized cooling performance for cold water exposure therapies.

In further embodiments, the surface-enhancing structures within the ice container 104 may be configured to perform multiple thermodynamic functions across different phases of operation. During a freezing phase prior to use, the fin 160, conductive inserts, and any additional internal protrusions act as heat conduction pathways that promote more rapid heat extraction from the treatment water used to form the treatment ice 406. By increasing contact between the freezing water and thermally conductive material distributed within the interior volume, the time required to prepare the ice container 104 for a therapy session may be reduced relative to containers having smooth interior walls.

During a use phase, when the ice container 104 is positioned within a tub containing treatment water 402, the same internal structures cooperate with circulating treatment water to enhance heat transfer from the treatment water to the treatment ice 406. In particular, treatment water delivered toward the ice container via one or more impingement ports may contact the treatment ice 406 at multiple locations, accelerating melting and promoting release of the treatment ice from the fin 160 or other internal structures as melting initiates. Once released, buoyancy causes the treatment ice 406 to move upward or float within the ice container 104, increasing the exposed surface area of the treatment ice in contact with circulating treatment water.

In some embodiments, the internal structures may include a plurality of protrusions, fins, ribs, or other features extending inward from one or more interior surfaces of the ice container 104. Such protrusions may be distributed along an interior bottom surface, sidewall, or combination thereof, and may be uniform or non-uniform in size, spacing, or orientation. These protrusions may be integrally formed with the ice container 104, bonded thereto, or provided as removable elements. In combination with the fin 160, the protrusions may further disrupt adhesion between the treatment ice 406 and the ice container 104 as melting begins, facilitating controlled release without manual intervention.

In embodiments including conductive inserts 172, the inserts may be positioned to extend partially or fully into the interior volume of the ice container 104 and may be arranged to project into regions of expected ice formation. The conductive inserts 172 may be formed from metals, alloys, ceramic-filled polymers, or other materials selected to provide enhanced thermal conductivity relative to the surrounding container body. In some embodiments, the inserts are removably received within mounts, recesses, or channels formed in the ice container 104, allowing users to tailor freezing and melting performance by selecting different insert configurations. In other embodiments, the inserts are permanently bonded or over-molded into the ice container 104 to provide a fixed thermal profile.

The internal structures described herein may be further configured to cooperate with fluid delivery features associated with a lid or agitator module, such that treatment water directed toward the ice container 104 impinges on the treatment ice 406 across multiple locations rather than at a single point. This distributed impingement increases overall heat exchange efficiency and promotes more uniform chilling of the treatment water 402 returned to the tub. As the chilled treatment water mixes with surrounding treatment water within the tub, the temperature of the treatment water contacting a user immersed therein may be reduced more rapidly, particularly during an initial phase of a therapy session.

Advantageously, by combining accelerated ice formation prior to use with controlled release, increased exposed ice surface area, and distributed impingement during use, the ice container 104 functions as an in-situ heat exchange component within an immersion-based cold water therapy system. Unlike closed-loop or isolated cooling systems in which treatment fluid is separated from the user, the embodiments described herein enable direct interaction between circulating treatment water, treatment ice, and the user within a shared treatment volume. This architecture provides improved thermal efficiency, reduced preparation time, and enhanced cooling performance without requiring external heat exchangers or wearable cooling interfaces.

Figure 22:
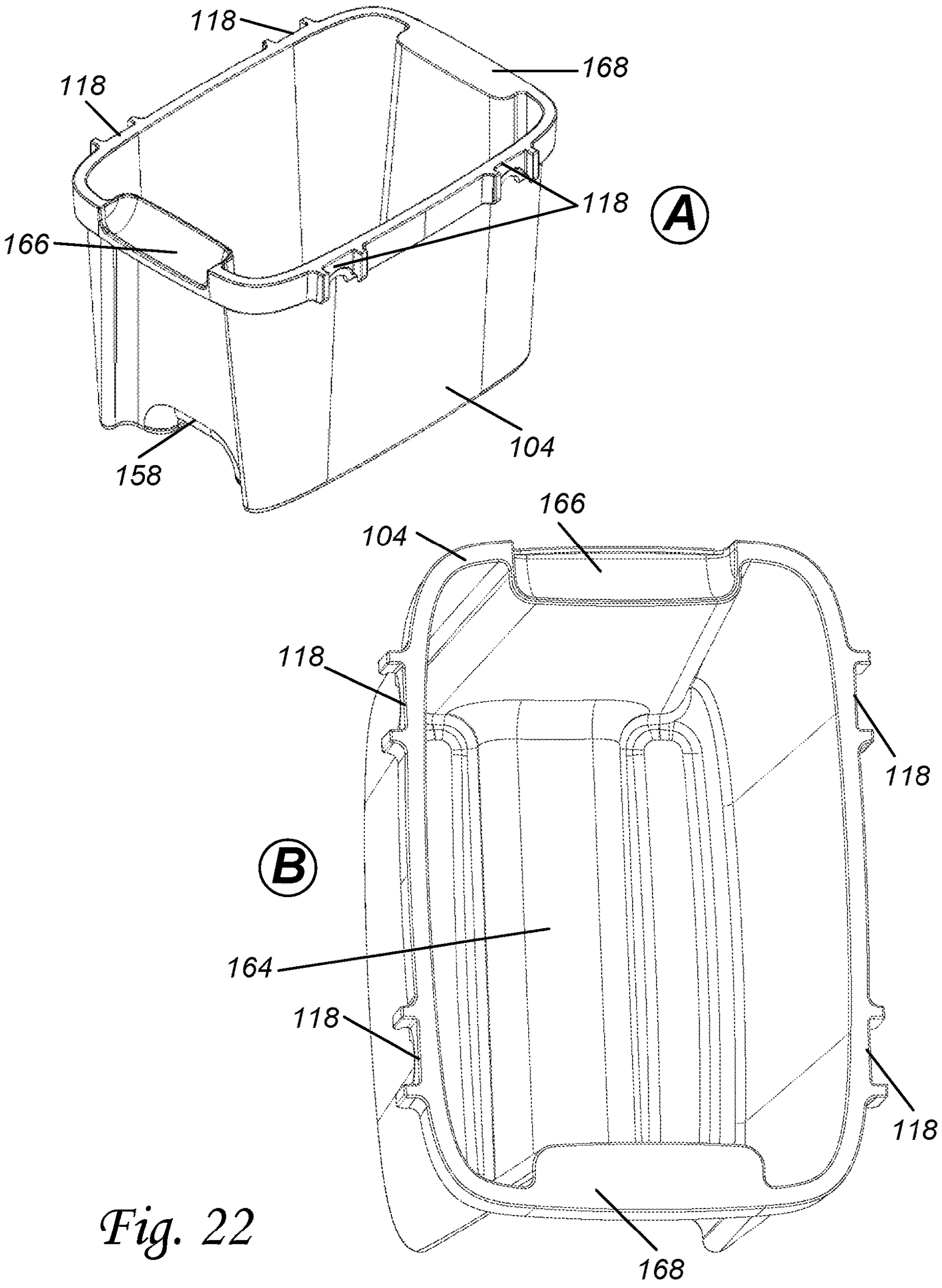
FIG. 22 illustrates one example of a perspective view of the ice container with internal view showing the ice container absent the fin.

Referring to FIG. 22, there is illustrated one example of a perspective view of the ice container 104, shown in two orientations similar to those presented in FIG. 21. In reference view ‘A’, a first perspective shows the internal volume of the ice container from above, while in reference view ‘B’, the container is tilted to expose the lower interior surface. In contrast to FIG. 21, the embodiment depicted here omits the upward-projecting fin 160, and instead incorporates a finless bottom surface 164.

The finless bottom surface 164 is a smooth, predominantly flat internal floor of the ice container 104. This configuration is used in embodiments where the optional fin 160 is not included. The flat surface facilitates easier molding, simplified cleaning, and may be preferred in use cases where slower or more uniform melting is desired. While it does not provide the accelerated melt behavior associated with the fin 160, the finless design still supports full integration with the agitator module 102, lid assembly, and treatment water circulation system.

By supporting interchangeable ice containers—with or without the fin—the system offers greater manufacturing flexibility and adaptability to different performance preferences. For example, high-intensity recovery sessions may benefit from the rapid melt dynamics enabled by the fin 160, while general—use or extended-duration sessions may favor the slower, steady chilling offered by the finless bottom 164. The lid locking features, fluid pathway architecture, and agitator interface remain fully compatible across both variants, preserving the modularity and interchangeability that define the chilling system 100.

Figure 23:
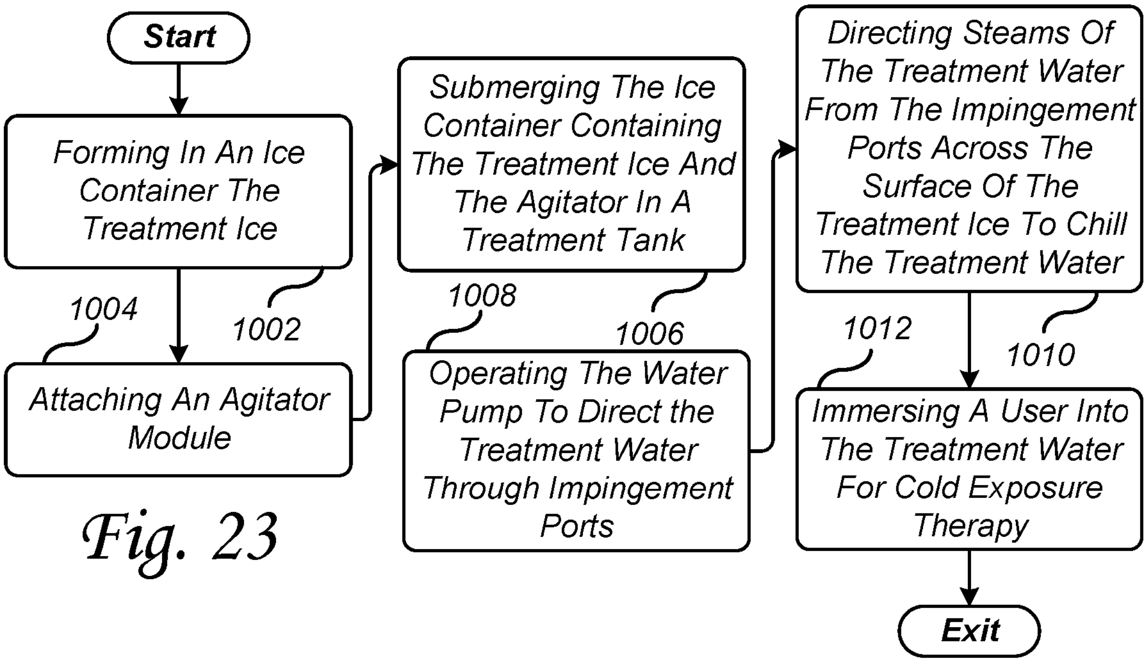
FIGS. 23-25 illustrated examples of a method for conducting temperature-controlled water exposure therapies.

Referring to FIG. 23, there is illustrated one example of a method for conducting temperature-controlled water exposure therapies using the chilling system 100. The method is presented as a flowchart of sequential steps, beginning with preparation and continuing through operation and therapeutic use.

This method demonstrates an integrated, modular, and user-driven approach to cold therapy, eliminating the need for loose ice, external plumbing, or uncontrolled chilling cycles. By leveraging directed water flow, surface-enhanced ice geometry, and intelligent pump control, the system delivers efficient and repeatable thermal exposure with minimal setup and high portability.

In step 1002, treatment ice is formed inside an ice container 104. The ice container is configured with a finned geometry, such as an internal fin 160, or other raised or recessed surface-enhancing features. These structural geometries imprint into the ice as it freezes, resulting in a treatment ice 406 with increased surface area. This expanded surface area promotes more efficient melting when exposed to treatment water 402, thereby accelerating the rate at which the surrounding water is cooled during therapy sessions.

In step 1004, an agitator module 102 is attached to the ice container 104. The agitator module includes a water pump 124, which is enclosed by a pump cover 120 and operatively connected to a water conduit 128. The agitator module is configured to mount securely to the container via alignment features such as the connecting enclosure 138, housing guide slots 166, and locking tab 168. Once attached, the system becomes a self-contained chilling unit ready for use.

In step 1006, the fully assembled chilling system is placed into a treatment tank 404 filled with treatment water 402.

In step 1008, the pump is activated using a mode select button 108, and begins drawing in treatment water through an inlet filter 152 positioned at the bottom of the agitator module. Water is then driven through the pump and routed through the water conduit 128, which terminates at the water conduit outlet 142, feeding into an inlet opening 140 on the inner lid 114.

In step 1010, the circulating treatment water is directed through at least one impingement port 130 disposed within the fluid channel 126 formed between the inner lid 114 and outer lid 116. The impingement ports emit streams of treatment water 402 at high velocity onto the surface of the treatment ice 406. The jet orientation, which may be angled or include vortex-inducing geometry, maximizes turbulent contact with the ice surface. This action removes thermal energy from the water rapidly, reducing water temperature in real-time.

In step 1012, once the treatment water 402 is sufficiently chilled, a user 302 can be immersed into the treatment tank 404 for cold exposure therapy. The circulating chilled water uniformly surrounds the user, allowing controlled thermal exposure with predictable temperature decline and recovery parameters. The continuous recirculation of water through the chilling system maintains target temperatures throughout the duration of the session, ensuring consistent and repeatable therapy outcomes.

Figure 24:
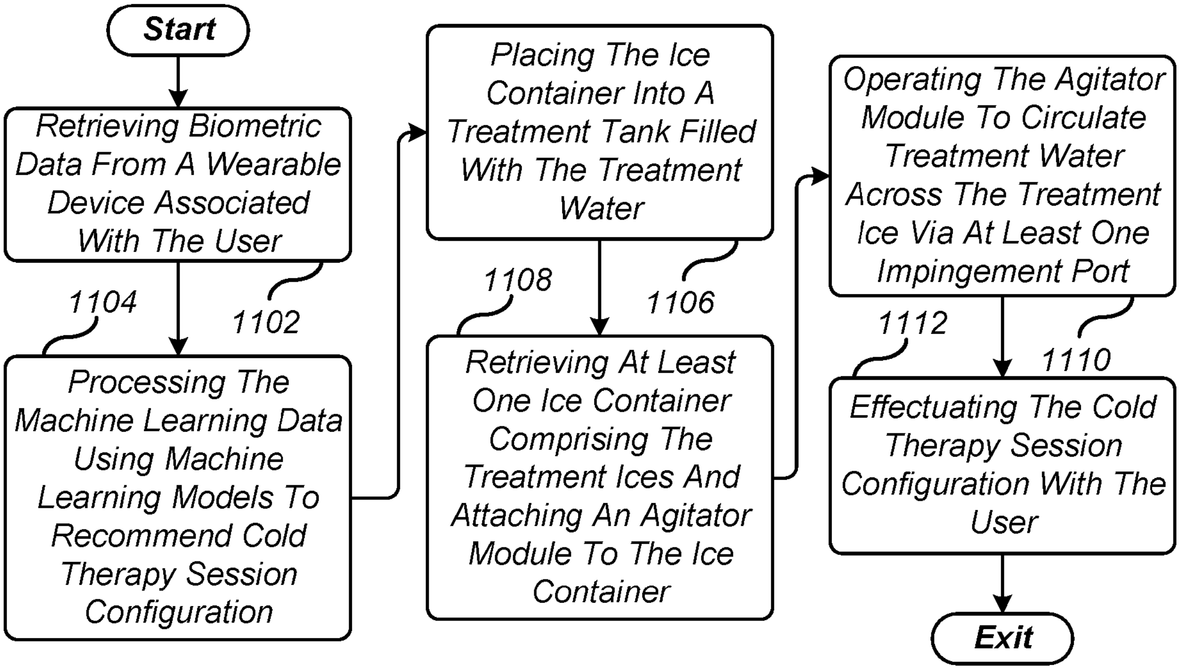

Referring to FIG. 24, there is illustrated one example of a method for conducting temperature-controlled water exposure therapies using biometric data and machine learning-driven personalization. The flowchart depicts a sequence of steps that combine user health data, predictive modeling, and modular system assembly to guide and execute an individualized cold exposure session using the chilling system 100.

This method represents a highly adaptive and intelligent implementation of cold therapy. By incorporating biometric feedback, predictive configuration, and modular hardware, the system personalizes treatment protocols to each user's physiological state and performance goals-offering a next-generation solution for wellness, recovery, and performance optimization.

In step 1102, biometric data is retrieved from a wearable device 606 associated with the user. This data may include metrics such as skin temperature, heart rate, recovery indicators, or activity levels, and is wirelessly communicated to the controller 500 via the communication interface 508 or relayed through a paired computing device 604, such as a smartphone 604A or tablet 604B. The wearable device 606 may be configured to continuously track physiological data, which is uploaded at session start or streamed in real-time.

In step 1104, the biometric data is processed by a machine learning model, either embedded within the controller 500 or hosted by a remote data processing resource 602 via a global network 600. The model analyzes the biometric input in the context of past session history and environmental conditions to recommend a cold therapy session configuration. This configuration may specify parameters such as the quantity of treatment ice 406 to be used, the desired impingement port 130 intensity, and the optimal session duration. The recommendation can be displayed to the user through a mobile app interface or synced directly to the chilling system 100.

In step 1106, the recommended number of ice containers 104 containing frozen treatment ice 406 are retrieved from a cooling and charge chamber 202. Each ice container may optionally feature a fin 160 or finless bottom surface 164, depending on the required melt rate. An agitator module 102, which includes a water pump 124, controller 500, and rechargeable battery 514, is then attached to each selected ice container. This prepares the system for deployment in accordance with the recommended session configuration.

In step 1108, the fully assembled chilling system 100 is placed into a treatment tank 404 filled with treatment water 402. The water conduit 128 is aligned with the inlet opening 140, enabling fluid intake and directional circulation towards the ice.

In step 1110, the agitator module 102 is activated-either manually via the mode select button 108 or automatically in response to the synced configuration- and begins circulating the treatment water. The pump 124 draws water through the inlet filter 152, pushes it through the water conduit 128, and into the fluid channel 126 via the inlet opening 140. The water is then driven through one or more impingement ports 130, which direct the chilled streams onto the surface of the treatment ice 406, enhancing melt and cooling the surrounding water. Jet intensity may be dynamically modulated in real time based on temperature readings from a temperature sensor 522.

In step 1112, the recommended cold therapy session is effectuated. The user enters the treatment tank 404, and the chilling system maintains circulation and thermal performance as defined by the session configuration. Throughout the session, the system may log performance data, monitor user interaction, and transmit outcome metrics back to the wearable device 606 or cloud-based server 602 for post-session analysis and future model training.

Figure 25:
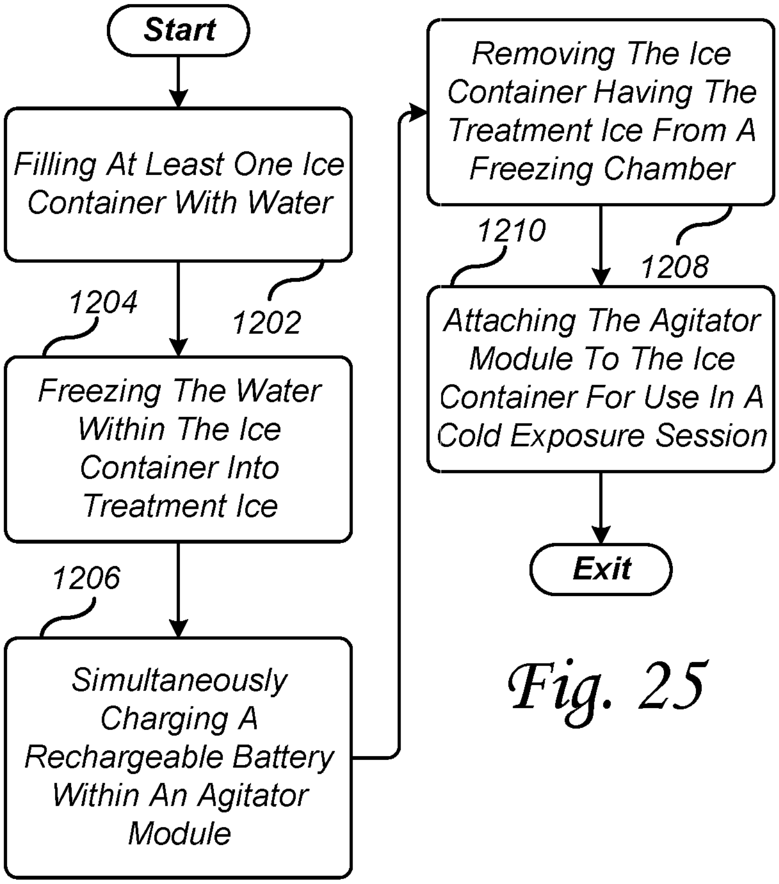

Referring to FIG. 25, there is illustrated one example of a method for preparing a chilling system 100 for conducting temperature-controlled water exposure therapies, as represented in a flowchart format. The method includes steps that begin with water loading and freezing and culminate in preparing a fully charged and assembled chilling system for a therapy session.

This preparation method enables a streamlined, modular workflow that minimizes downtime between sessions and supports reliable system readiness. By coordinating ice formation with battery charging and enabling simple field assembly, the system facilitates repeatable, user-friendly deployment in home or professional environments.

In step 1202, at least one ice container 104 is filled with water. The container may feature internal geometry such as a fin 160 or finless bottom surface 164, depending on the desired melt profile. The water may be introduced through an open top prior to sealing with the inner lid 114 and outer lid 116. Each container is dimensioned to hold a predetermined volume of water, which when frozen will form a high-surface-area treatment ice 406 suitable for efficient thermal exchange during therapy.

In step 1204, the filled ice container is placed into a freezing chamber or cooling and charge chamber 202, where the water is solidified into treatment ice. The chamber may include features such as conductive shelves 214 or thermal ribs 204 to accelerate heat extraction during the freezing process. While the water is freezing, a rechargeable battery 514 located within an agitator module 102 is simultaneously charged. The agitator module may be docked on or near an inductive charging coil 216 embedded in the chamber. A recharge controller 516 manages the charge cycle, ensuring the system is ready for portable use immediately after freezing is complete.

In step 1206, once the water is frozen, the ice container 104 containing the treatment ice 406 is removed from the freezing chamber. The container may be easily handled using the scooped handle 166 and flat handle 168, which assist with lifting and alignment. This step ensures the ice container is ready to be coupled with the agitator module and deployed into a treatment tank.

In step 1208, the agitator module 102, which now contains a fully charged battery, is attached to the ice container 104. The agitator module comprises the water pump 124, controller 500, water conduit 128, and necessary housing structures such as the pump cover 120, controls cover 122, and connecting enclosure 138. The system is now fully assembled and ready for use in a cold exposure therapy session, wherein it can be submerged in a treatment tank 404, activated, and used to circulate and chill treatment water 402.

Figure 26:
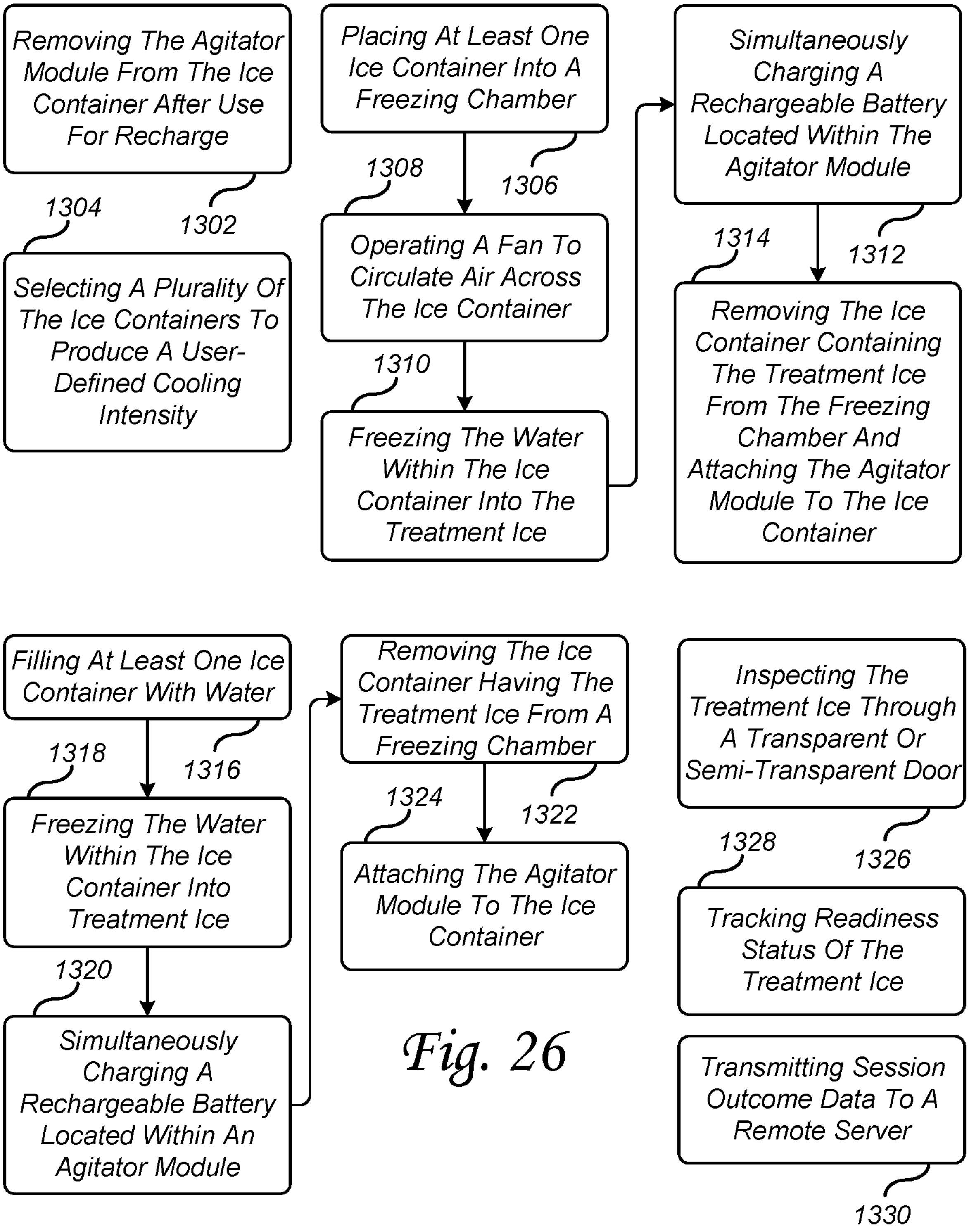
FIGS. 26-28 illustrated exemplary embodiments that can be used interchangeably with the methods of the present invention.

Referring to FIG. 26, there are illustrated exemplary embodiments that can be used interchangeably with the methods of the present invention.

In step 1302, the agitator module 102 is removed from the ice container 104 after the completion of a cold therapy session. The agitator module-comprising a water pump 124, controller 500, and rechargeable battery 514—is configured for detachable engagement via structures such as the connecting enclosure 138 and associated guide and latch features. After the system has completed treatment water circulation and the treatment ice 406 has melted or sufficiently cooled the bath, the user disengages the agitator module from the container housing. The scooped handle 166 and flat handle 168 on the ice container facilitate stable handling during removal.

Once detached, the agitator module may be cleaned, inspected, and placed into a cooling and charge chamber 202 or similar recharge interface. Charging may be conducted via a physical charging port or through inductive charging coils 216 embedded in the chamber. The recharge controller 516 manages safe energy transfer to the battery 514, preparing the module for its next use cycle. This modular separation of power/control and thermal mass simplifies maintenance and increases system longevity, while reducing user effort between therapy sessions.

In step 1304, a plurality of ice containers 104 is selected to achieve a user-defined cooling intensity for a given cold therapy session. Because each container can be independently prepared with treatment ice 406 and outfitted with an agitator module 102, the number of deployed units directly influences the total surface area of ice available for chilling treatment water 402. By selecting more containers-whether based on session duration, target temperature drop, or user recovery needs—the system provides granular control over the chilling rate and thermal load. This modular, quantized approach allows users to scale therapy intensity without requiring system redesign or complex settings.

In step 1306, at least one ice container 104 filled with water is placed into a freezing chamber, such as a cooling and charge chamber 202. The ice container may feature internal geometries such as a fin 160 or finless bottom surface 164, which shape the resulting ice into a structure optimized for thermal exchange.

In step 1308, a fan 210 is activated to circulate air 212 across the placed ice container within the freezing chamber. This airflow improves thermal transfer by reducing insulating air layers and ensures uniform freezing across the water volume. When multiple containers are vertically stacked, the fan orientation may be configured to optimize cross-sectional airflow between containers.

In step 1310, the circulated air, in combination with conductive shelves 214 or thermal ribs 204, freezes the water within the ice container into treatment ice 406. These conductive components enhance heat extraction by maintaining high contact with the container base, shortening freeze time and producing solid, stable ice geometry.

In step 1312, during the ice formation process, a rechargeable battery 514 within an agitator module 102 is simultaneously charged via a charging station 206 integrated into the freezing chamber. Charging may occur through inductive charging coils 216 positioned near or beneath the agitator module or through physical charging contacts, and is managed by a recharge controller 516 that ensures safe and efficient energy delivery.

In step 1314, once freezing is complete, the ice container-now containing fully formed treatment ice—is removed from the freezing chamber. The agitator module 102, having completed its charging cycle, is then attached to the container using an interface that includes components such as the connecting enclosure 138, housing guide slots 166, and locking tab 168. This completes the system assembly, rendering it ready for deployment in a treatment tank 404 for cold exposure therapy.

In step 1316, at least one ice container 104 is filled with water in preparation for a cold therapy session. The container may include internal geometry such as a fin 160 or finless bottom surface 164, which determines the surface-enhancing characteristics of the resulting treatment ice 406. The container's wide opening and integrated scooped handle 166 assist in safe filling, handling, and alignment within the freezing system.

In step 1318, the water-filled ice container is placed into a freezing chamber, such as the cooling and charge chamber 202, where it is frozen into treatment ice. The chamber may include a conductive shelf 214 or thermal rib 204 thermally coupled to a cold plate to promote uniform heat extraction. A fan 210 may circulate airflow 212 throughout the cavity to accelerate and standardize the freezing process.

In step 1320, while the water is freezing into treatment ice, a rechargeable battery 514 housed within an agitator module 102 is simultaneously charged. The agitator module may be placed on or near an inductive charging coil 216 embedded in the freezing chamber and monitored by a recharge controller 516, enabling full charging by the time the ice is ready.

In step 1322, the ice container 104 containing the frozen treatment ice 406 is removed from the freezing chamber using the scooped handle 166 or flat handle 168. The modularity of the system allows the user to easily retrieve and deploy pre-frozen units for therapy preparation.

In step 1324, the agitator module 102 is attached to the ice container 104. This connection is made using guiding and fastening structures such as the connecting enclosure 138, housing guide slots 166, and locking tab 168, creating a sealed assembly that channels water through the water conduit 128 and into the chilling system during use.

In step 1326, the user may inspect the treatment ice 406 during formation through a transparent or semi-transparent door 220 of the freezing chamber. This visual access enables the user to verify full freeze completion without opening the chamber, preserving internal temperature and improving energy efficiency.

In step 1328, the system tracks the readiness status of both the treatment ice and the agitator module. The freezing chamber may include programmed logic, timers, or thermal sensors that monitor elapsed freeze time, while the agitator module reports charge status via the controller 500 and status indicator 144, enabling a readiness signal to be displayed locally or via a connected application 604.

In step 1330, after the therapy session concludes, session outcome data-such as duration, peak cooling rate, temperature profile, and user-reported experience—may be transmitted to a remote server 602. This transmission occurs over a global network 600 via the communication interface 508 within the controller 500, allowing the machine learning model to refine future session recommendations based on aggregated real-world data.

Figure 27:
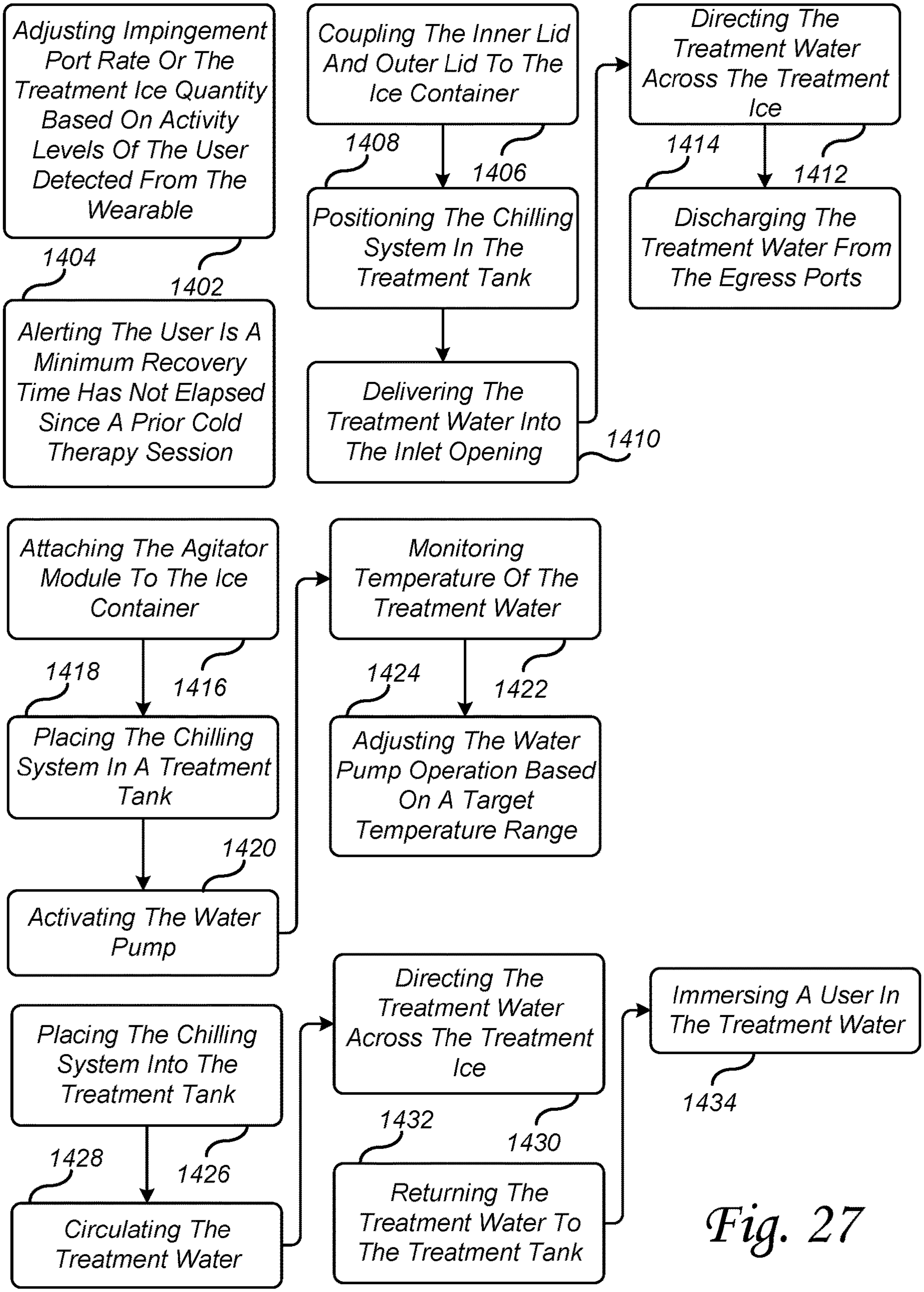

Referring to FIG. 27, there are illustrated exemplary embodiments that can be used interchangeably with the methods of the present invention.

In step 1402, the impingement port 130 flow rate or the number of ice containers 104 used during a session is adjusted based on activity levels of the user as detected by a wearable device 606. The wearable device may monitor movement, exertion, or recovery metrics and communicate this data to the controller 500 via the communication interface 508. Based on the received information, the system dynamically alters the treatment water 402 circulation intensity or increases the quantity of treatment ice 406 to meet recovery needs. This closed-loop adjustment ensures optimal cold exposure tailored to the user's physiological state and activity profile.

In step 1404, the system issues an alert to the user if a minimum recovery time has not elapsed since a previous cold therapy session. This safeguard is based on historical usage data stored in memory or retrieved from a remote data processing resource 602. The controller 500, in coordination with a connected mobile device 604 or the wearable 606, monitors session timestamps and enforces safe recovery intervals to prevent overexposure. If a new session is initiated prematurely, the system may delay activation or prompt the user with a visual or haptic warning until recovery criteria are satisfied.

In step 1406, the inner lid 114 and outer lid 116 are coupled together and secured to the ice container 104, forming a sealed unit that defines a fluid channel 126 between the two lids. The assembly is secured using latches 110, latch pins 112, and latch connectors 118, which maintain alignment and prevent leakage during operation. This configuration enables fluid to be directed towards the treatment ice in a controlled manner while also providing structural integrity during transport and immersion.

In step 1408, the fully assembled chilling system 100—including the ice container, agitator module, and lid assembly—is positioned in a treatment tank 404 filled with treatment water 402. The scooped handle 166 and flat handle 168 facilitate ergonomic lowering and stable seating of the system in the tub, ensuring proper flow alignment and thermal contact between the treatment ice and circulating water.

In step 1410, treatment water 402 is delivered into the inlet opening 140 using the water pump 124 housed within the agitator module 102. The pump draws water in through the inlet filter 152, routes it through the water conduit 128, and directs it into the fluid channel formed between the inner and outer lids. The system ensures continuous delivery of water for active thermal exchange.

In step 1412, the treatment water flows through the fluid channel 126 and is projected towards the surface of the treatment ice 406 via at least one impingement port. These jets may be oriented at various angles and include turbulence-enhancing features to maximize surface contact and thermal agitation, resulting in efficient melting and heat extraction.

In step 1414, the treatment water, having been chilled by contact with the treatment ice, is discharged from the system through one or more egress ports/paths 134 formed in the outer lid 116. The water passes through fluid channel slots 136 and reenters the treatment tank 404, where it uniformly distributes around the user 302 for therapeutic cold exposure. This controlled recirculation maintains water temperature and delivers consistent cooling throughout the session.

In step 1416, the agitator module 102 is attached to the ice container 104, forming a unified chilling system assembly. The agitator module, which houses the water pump 124, controller 500, temperature sensor 522, and rechargeable battery 514, interlocks with the container via features such as the connecting enclosure 138 and integrated conduit alignment. This modular attachment enables portable, tool-free assembly and ensures reliable water flow routing for the chilling cycle.

In step 1418, the assembled chilling system 100—now containing treatment ice 406 and the attached agitator module—is placed into a treatment tank 404 filled with treatment water 402. The system's geometry and integrated scooped handle 166 and flat handle 168 allow ergonomic placement and stability during operation.

In step 1420, the water pump 124 is activated using the mode select button 108 located on the agitator module. This interface allows the user to choose a pump operation mode (e.g., low, medium, or high flow), initiating the circulation of treatment water through the internal channels of the system.

In step 1422, the temperature sensor 522, housed within or near the pump's circulation pathway, begins monitoring the temperature of the treatment water. This real-time measurement provides the basis for adaptive system response, ensuring water is cooled to an appropriate therapeutic range.

In step 1424, the controller 500 evaluates temperature data and dynamically adjusts the water pump's operation-modulating flow rate, duration, or jet intensity—to maintain a target temperature range. This closed-loop regulation ensures effective and consistent cold therapy tailored to user preferences or biometric recommendations.

In step 1426, the fully assembled chilling system 100, including the ice container 104, treatment ice 406, and agitator module 102, is placed into a treatment tank 404 filled with treatment water 402. The configuration allows for seamless deployment, either in residential or professional therapy environments.

In step 1428, the treatment water 402 is circulated using the water pump 124, which draws the water through the inlet filter 152, propels it through the water conduit 128, and delivers it into the fluid channel 126 formed between the inner lid 114 and outer lid 116.

In step 1430, the circulated treatment water is directed towards the treatment ice 406 via at least one impingement port 130. The jet orientation, geometry, and flow intensity promote rapid ice melt and heat exchange, effectively chilling the water during contact.

In step 1432, the chilled treatment water, having passed over the ice, flows through one or more egress ports/paths 134 located in the outer lid 116. The water exits through fluid channel slots 136 and returns to the surrounding volume of the treatment tank 404, forming a recirculating loop that maintains water temperature near the user.

In step 1434, the user 302 is immersed in the treatment water 402, experiencing the therapeutic effects of the chilled environment. The active circulation system ensures consistent thermal contact, improving recovery outcomes compared to static water immersion.

Figure 28:
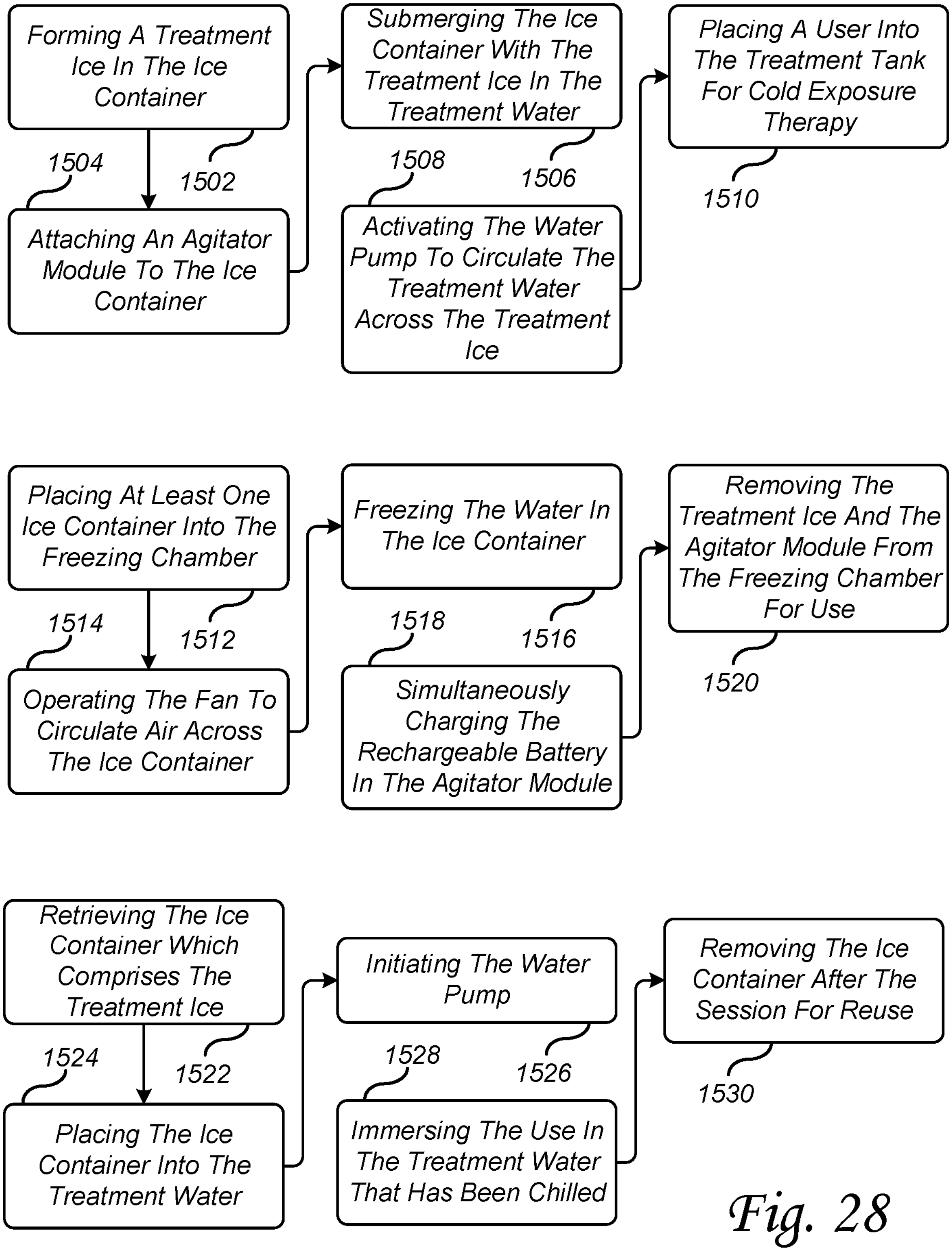

Referring to FIG. 28, there are illustrated exemplary embodiments that can be used interchangeably with the methods of the present invention.

In step 1502, the treatment ice 406 is formed within the ice container 104. The container's interior geometry, which may include a fin 160 or a finless bottom surface 164, shapes the frozen water to maximize surface area and melting performance. The container may be placed in a freezing chamber 202, where thermal ribs 204, conductive shelves 214, and circulating air 212 help expedite freezing.

In step 1504, the agitator module 102 is attached to the ice container. The module includes a water pump 124, controller 500, rechargeable battery 514, and supporting interfaces such as the water conduit 128 and connecting enclosure 138, forming a self-contained assembly capable of powered treatment water circulation.

In step 1506, the ice container-now containing the treatment ice and agitator module—is submerged into treatment water 402 within a treatment tank 404. The container's scooped handle 166 and flat handle 168 allow safe and stable placement into the water.

In step 1508, the water pump 124 is activated to begin circulating the treatment water towards the treatment ice. The pump draws water through the inlet filter 152, directs it into the fluid channel 126, and propels it toward the surface of the treatment ice via one or more impingement ports 130, enhancing chilling efficiency through active contact.

In step 1510, the user 302 is placed into the treatment tank 404 for cold exposure therapy. The actively circulated, chilled water provides a uniform thermal environment that supports physical recovery and therapeutic objectives.

In step 1512, at least one ice container 104 is placed into the freezing chamber 202, which is configured to accommodate one or more containers vertically or laterally using positioning recesses 156. This ensures airflow and heat exchange are evenly distributed during freezing.

In step 1514, the fan 210 is operated to circulate air 212 across and through the chamber. This airflow supports consistent and rapid freezing by maintaining a uniform ambient temperature around the ice containers.

In step 1516, the water inside the ice container freezes into treatment ice 406, aided by contact with conductive shelf 214 or thermal rib 204 structures that draw heat away from the container's base. The resulting ice block may include raised geometries for improved melt performance.

In step 1518, while the water is freezing, the rechargeable battery 514 within the agitator module 102 is simultaneously charged. This may occur via inductive charging coils 216 embedded within or beneath the chamber, regulated by a recharge controller 516 to manage charging cycles.

In step 1520, after freezing is complete, the treatment ice 406 and the charged agitator module 102 are removed from the freezing chamber 202 for use in a subsequent water exposure therapy session. The components are now prepared for immediate assembly and deployment.

In step 1522, the ice container 104, which now contains treatment ice 406 and has the agitator module 102 attached, is retrieved from storage or the freezing chamber for active use.

In step 1524, the fully prepared ice container is placed into treatment water 402 within a treatment tank 404, where it will begin chilling the water upon activation.

In step 1526, the water pump 124 is initiated, beginning active circulation of treatment water through at least one impingement port 130. The water passes over the treatment ice, extracting thermal energy and returning to the tub in a chilled state.

In step 1528, the user 302 is immersed in the treatment water 402, now cooled through contact with the circulated treatment ice. The uniform temperature distribution enhances the therapeutic effect and supports repeatable treatment conditions.

In step 1530, following the session, the ice container 104 is removed from the treatment water. The modular assembly allows for easy disassembly, cleaning, and reuse in subsequent therapy cycles, preserving battery life and ice container integrity.

The capabilities of the present invention can be implemented in software, firmware, hardware, or some combination thereof.

The flow diagrams depicted herein are just examples. There may be many variations to these diagrams or the steps (or operations) described therein without departing from the spirit of the invention. For instance, the steps may be performed in a different order, or steps may be added, deleted, or modified. All of these variations are considered a part of the claimed invention.

While the preferred embodiment of the invention has been described, it will be understood that those skilled in the art, both now and in the future, may make various improvements and enhancements which fall within the scope of the claims which follow. These claims should be construed to maintain the proper protection for the invention first described.

What is claimed is:

1. An ice container assembly configured for use in cold water immersion therapy, the ice container assembly comprising:

an ice container configured to be positioned within a tub containing treatment water, the ice container defining an interior volume and being configured to hold treatment ice;

a lid coupled to the ice container;

one or more internal fluid channels formed in the lid;

one or more impingement ports fluidly coupled to the one or more internal fluid channels;

an agitator module coupled to the lid;

a pump disposed within the agitator module;

a connecting enclosure fluidly coupled to the pump;

wherein the pump is configured to draw the treatment water from the tub;

wherein the connecting enclosure defines:

an internal flow passage extending along a vertical axis with internal contours; and one or more angular bends that redirects the treatment water from the vertical axis into the one or more internal fluid channels;

wherein the one or more internal fluid channels deliver the treatment water to the one or more impingement ports;

wherein the one or more impingement ports discharge the treatment water toward the treatment ice within the ice container;

directing the treatment water toward the treatment ice to chill the treatment water; and recirculating the treatment water after chilling back into the tub, wherein the user is fully or partially immersed in the treatment water, for cold therapy treatment, when the treatment water is chilled.

2. The ice container assembly of claim 1, further comprising:

at least one fin extends upward from an interior bottom surface of the ice container, the at least one fin configured to accelerate formation of the treatment ice during freezing prior to use of the ice container in cold water immersion therapy.

3. The ice container assembly of claim 1, further comprising:

one or more internal structures having a plurality of protrusions extending inward from an interior wall of the ice container.

4. The ice container assembly of claim 1, further comprising:

one or more conductive inserts that are removably positioned within the interior volume and configured to enhance heat transfer and reduce freeze time of water into the treatment ice.

5. The ice container assembly of claim 4, wherein the one or more conductive inserts comprise at least one of a metal rod, a metal fin, or a thermally optimized polymer element.

6. The ice container assembly of claim 1, wherein during melting of the treatment ice, the treatment ice separates from the ice container and float upward within the ice container, thereby increasing a surface area of the treatment ice in contact with the circulating treatment water and promoting faster chilling of the treatment water in the tub.

7. A method of using the ice container assembly of claim 1, the method comprising:

circulating the treatment water from the tub through the pump and the connecting enclosure;

delivering the treatment water through the one or more internal fluid channels to the one or more impingement ports;

directing the treatment water toward the treatment ice, chilling the treatment water as the treatment ice melts;

recirculating the treatment water back into the tub; and fully or partially immersing the user, for cold therapy treatment, in the treatment water when the treatment water is chilled.

8. An ice container assembly configured for use in cold water immersion therapy, the ice container assembly comprising:

an ice container configured to be positioned within a tub containing a treatment water, the ice container defining an interior volume and being configured to hold treatment ice;

a lid coupled to the ice container;

one or more internal fluid channels formed in the lid;

one or more impingement ports fluidly coupled to the one or more internal fluid channels;

wherein the treatment water contained in the tub is configured to contact a user, who is fully or partially immersed in the treatment water;

wherein the treatment water is drawn from the tub, delivered to the one or more internal fluid channels, and then discharged through the one or more impingement ports toward the treatment ice; and wherein the discharged treatment water contacts the treatment ice to chill the treatment water and returns the treatment water to the tub, forming a recirculating treatment water loop.

9. The ice container assembly of claim 8, wherein the one or more internal fluid channels are formed as recessed flow passages in the lid.

10. The ice container assembly of claim 8, wherein the one or more internal fluid channels distribute the treatment water to a plurality of impingement ports spaced apart from one another such that the treatment water is directed toward the treatment ice across multiple spaced locations to promote more uniform chilling of the treatment water.

11. The ice container assembly of claim 8, wherein the one or more impingement ports are spaced about the ice container.

12. The ice container assembly of claim 8, further comprising:

one or more conductive inserts positioned within the interior volume, wherein the one or more conductive inserts comprise at least one of a metal rod, a metal fin, or a thermally optimized polymer element.

13. A method of using the ice container assembly of claim 8, the method comprising:

circulating the treatment water through the one or more internal fluid channels;

discharging the treatment water from the one or more impingement ports toward the treatment ice; and allowing the treatment ice to release from the ice container to increase heat transfer.

14. An ice container assembly configured for use in cold water immersion therapy, the ice container assembly comprising:

an ice container configured to be positioned within a tub containing treatment water, the ice container defining an interior volume and being configured to hold treatment ice;

a lid coupled to the ice container;

one or more internal fluid channels formed in the lid;

one or more impingement ports fluidly coupled to the one or more internal fluid channels;

one or more conductive inserts positioned within the interior volume of the ice container, the one or more conductive inserts being configured to accelerate formation of the treatment ice during freezing prior to use of the ice container in cold water immersion therapy;

wherein, during use, treatment water drawn from the tub is delivered through the one or more internal fluid channels and discharged through the one or more impingement ports toward the treatment ice; and wherein the discharged treatment water contacts the treatment ice to chill the treatment water and returns to the tub to form a recirculating treatment water loop.

15. The ice container assembly of claim 14, wherein the one or more conductive inserts are permanently bonded to the ice container.

16. The ice container assembly of claim 14, wherein the one or more conductive inserts are removably received within mounts formed in the ice container.

17. The ice container assembly of claim 14, wherein the one or more conductive inserts extend inward from a wall of the ice container.

18. The ice container assembly of claim 14, wherein upward movement of the treatment ice increases a melt rate of the treatment ice during immersion therapy.

19. A method of using the ice container assembly of claim 14, the method comprising:

freezing treatment water within the ice container around the one or more conductive inserts to form the treatment ice;

submerging the ice container in the treatment water contained in the tub; and circulating the treatment water through the lid and the one or more impingement ports to cause detachment and upward movement of the treatment ice.

20. The method of claim 19, further comprising controlling circulation of the treatment water to execute a therapy treatment cycle defined by at least one time parameter and at least one temperature parameter.

* * * * *